United States Patent
Shalitin et al.

(10) Patent No.: US 12,416,099 B2
(45) Date of Patent: Sep. 16, 2025

(54) METHODS OF OPTIMIZING GENE EXPRESSION IN PLANT

(71) Applicant: PLANTARC BIO LTD., Raanana (IL)

(72) Inventors: Dror Shalitin, Raanana (IL); Noam Grimberg, Kibutz Lehavot Haviva (IL); Daniel Bechar, Kibbutz Givat Haim Meuhad (IL); Tal Cohen, Herzelyia (IL)

(73) Assignee: PLANTARC BIO LTD., Raanana (IL)

( * ) Notice: Subject to any disclaimer, the term of this patent is extended or adjusted under 35 U.S.C. 154(b) by 0 days.

(21) Appl. No.: 18/892,893

(22) Filed: Sep. 23, 2024

(65) Prior Publication Data

US 2025/0059531 A1    Feb. 20, 2025

Related U.S. Application Data

(63) Continuation of application No. PCT/IL2023/050380, filed on Apr. 9, 2023.

(30) Foreign Application Priority Data

Apr. 12, 2022  (IL) .......................................... 292199

(51) Int. Cl.
    C40B 30/06    (2006.01)
(52) U.S. Cl.
    CPC .................... C40B 30/06 (2013.01)
(58) Field of Classification Search
    None
    See application file for complete search history.

(56) References Cited

U.S. PATENT DOCUMENTS

| 2011/0185444 A1 | 7/2011 | Li et al. |
| 2021/0403901 A1 | 12/2021 | Mei et al. |

FOREIGN PATENT DOCUMENTS

| EP | 2652139 | 10/2021 |
| JP | H1118775 A | 1/1999 |
| JP | 2000-506724 A | 6/2000 |
| JP | 2009-521936 A | 6/2009 |
| KR | 20190072433 A | 6/2019 |
| WO | 2020089489 | 5/2020 |

OTHER PUBLICATIONS

Jores et al. (May 14, 2000) The Plant Cell vol. 32 pp. 2120 to 2031 (Year: 2000).*

(Continued)

*Primary Examiner* — Christian C Boesen
(74) *Attorney, Agent, or Firm* — The Roy Gross Law Firm, LLC; Roy Gross

(57) ABSTRACT

A method for in-planta high throughput evaluation of endogenous genetic regulatory elements of a crop plant, obtaining a nucleic acid encoding a native regulatory element of a trait-related gene, introducing one or more genetic changes in each of a plurality of copies of the native regulatory element, introducing the genetic library into model plants, utilizing high throughput transformation, screening the transformed model plants, and identifying the one or more genetic changes in the altered regulatory element of the selected model plant.

12 Claims, 9 Drawing Sheets
(4 of 9 Drawing Sheet(s) Filed in Color)
Specification includes a Sequence Listing.

(56) References Cited

OTHER PUBLICATIONS

Lu et al. A donor-DNA-free CRISPR/Cas-based approach to gene knock-up in rice. Nature plants. Nov. 2021;7(11):1445-52. https://doi.org/10.1038/s41477-021-01019-4.
Li et al. Development of PPO inhibitor-resistant cultures and crops. Pest Management Science: formerly Pesticide Science. Mar. 2005;61(3):277-85. doi: 10.1002/ps.1011. PMID: 15660355.
Gaj et al. ZFN, TALEN, and CRISPR/Cas-based methods for genome engineering. Trends in biotechnology. Jul. 2013;31(7):397-405. doi: 10.1016/j.tibtech.2013.04.004. Epub May 9, 2013. PMID: 23664777; PMCID: PMC3694601.
Rodríguez-Leal et al. Engineering quantitative trait variation for crop improvement by genome editing. Cell. Oct. 5, 2017;171(2):470-80. doi: 10.1016/j.cell.2017.08.030. Epub Sep. 14, 2017. PMID: 28919077.
Jain et al. Enhancers as potential targets for engineering salinity stress tolerance in crop plants. Physiologia Plantarum. Dec. 2021;173(4):1382-91. doi: 10.1111/ppl.13421. Epub Apr. 21, 2021. PMID: 33837536.
S. Rama Devi et al (2006). A novel high-throughput genetic screen for stress-responsive mutants of *Arabidopsis thaliana* reveals new loci involving stress responses. The Plant Journal, 47(4), 652-663. doi: 10.1111/j.1365-313X.2006.02814.x. Epub Jul. 11, 2006. PMID: 16856987.
Li, C., Li, W., Zhou, Z., Chen, H., Xie, C., & Lin, Y. (2019). A new rice breeding method: CRISPR/Cas9 system editing of the Xa13 promoter to cultivate transgene-free bacterial blight-resistant rice. Plant Biotechnology Journal, 18(2), 313-315. doi: 10.1111/pbi. 13217. Epub Aug. 14, 2019. PMID: 31344313; PMCID: PMC6953186.
De Paepe, A., De Buck, S., Hoorelbeke, K., Nolf, J., Peck, I., & Depicker, A. (2009). High frequency of single-copy T-DNA transformants produced by floral dip in CRE-expressing *Arabidopsis* plants. The Plant Journal, 59(4), 517-527. doi: 10.1111/j.1365-313X. 2009.03889.x. Epub Apr. 6, 2009.
Acharya, S., Ranjan, R., Pattanaik, S., Maiti, I. B., & Dey, N. (2014). Efficient chimeric plant promoters derived from plant infecting viral promoter sequences. Planta, 239(2), 381-396. DOI 10.1007/s00425-013-1973-2.
Ranjan, R., & Dey, N. (2012). Development of vascular tissue and stress inducible hybrid-synthetic promoters through DOF-1 motifs rearrangement. Cell biochemistry and biophysics, 63(3), 235-245. DOI 10.1007/s12013-012-9359-9.
Pandiarajan, R., & Grover, A. (2018). In vivo promoter engineering in plants: are we ready?. Plant Science, 277, 132-138. https://doi.org/10.1016/j.plantsci.2018.10.011.
Zhao, M., Yuan, Z., Wu, L., Zhou, S., & Deng, Y. (2021). Precise prediction of promoter strength based on a de novo synthetic promoter library coupled with machine learning. ACS Synthetic Biology, 11(1), 92-102. https://doi.org/10.1021/acssynbio.1c00117.

* cited by examiner

METHODS OF OPTIMIZING GENE EXPRESSION IN PLANT

CROSS REFERENCE TO RELATED APPLICATIONS

This application is a Bypass Continuation of PCT Patent Application No. PCT/IL2023/050380 having International filing date of Apr. 9, 2023, which claims the benefit of priority of Israeli Patent Application No. 292199, filed Apr. 12, 2022, the contents of which are all incorporated herein by reference in their entirety.

REFERENCE TO AN ELECTRONIC SEQUENCE LISTING

The contents of the electronic sequence listing (PAB_007-WOUS.xml; Size: 136,922 bytes; and Date of Creation: Nov. 7, 2024) is herein incorporated by reference in its entirety.

FIELD OF THE INVENTION

The present invention generally relates to the field of improving traits in plants. More particularly, the present invention relates to optimizing the expression of natural plant traits by screening libraries of genetic elements in plants and identifying desirable expression levels of traits.

BACKGROUND

Crops harboring improved traits have a significant economic impact because of gain in product yield and quality. Enhanced resistance to a variety of biotic or abiotic stress factors such as herbicides, insects, diseases, extreme heat, and drought, is, therefore, a desirable and advantageous feature that is not being addressed comprehensively by current methodologies. Time-consuming methods for identifying and improving traits, for example by conventional plant breeding, and the heavily elaborated regulatory process accompanied to genetic engineering of genetically modified (GMO) crops do not provide a complete, all-inclusive solution.

For example, the most addressed problem is weeds growing together with crops, interfering with crop's uniformity and yield that is accompanied to the use of herbicides. Losses in yield and quality due to undesired weed growth, as well as costs of controlling weeds, have a major economic impact on crop production. It is estimated that yield loss of about 50% would occur when weeds in the field are unattended to, during the growth of a crop. Therefore, there is a great need for use of various herbicides to attend this problem. In addition, the rapid increase in herbicide-resistant weeds creates a huge challenge to global food security because it can reduce crop production, causing considerable losses. Combined with a lack of novel herbicides, cultivating herbicide-resistant crops becomes an effective strategy to control weeds because of reduced crop phytotoxicity, and it expands the herbicidal spectrum.

Herbicide tolerant (HT) crops offer benefits such as reduced usage and the ability to introduce modern and safer agrochemicals.

Some of the most common GMO crops, such as corn, soybeans, cotton, and canola, harbor an HT gene such as bar or pat that share tolerance for Glutamine Synthesis Inhibitors, or for the Glyphosate-based herbicides, such as Roundup, which targets the enzyme 5-enolpyruvylshikimate 3-phosphate synthase (EPSPS). Roundup Ready plants carry the gene coding for a glyphosate-insensitive form of this enzyme, obtained from *Agrobacterium* sp. strain CP4 EPSPS (Roundup), or other resistant genes.

However, state-of-the-art solutions for HT include GMO crops with transformed endogenous genes, an approach that requires prior knowledge of trait-related genes that can be targeted or harnessed for use. In addition, decreased public acceptance of GMO technology over the past years led to a search for new and greener technologies such as natural resistance that is increasingly hard to find.

In several cases, natural resistance mechanisms by the plant's native genes proved the required efficiency to overcome the stress factor. For example, higher than normal expression levels of the plant's native genes, which are targets of the herbicides, result in increased HT, as the high level of the native enzyme overcomes the herbicide thereby conferring resistance.

Such natural resistance is observed for high expression levels of the plant's native 5-enolpyruvylshikimate-3-phosphate synthase (EPSPS), leading formation of weeds resistant to an EPSPS inhibitor type herbicide such as Glyphosate.

There is, therefore, an unmet need for a comprehensive solution for improving and optimizing gene expression level and/or phenotypes of plants.

SUMMARY OF THE INVENTION

According to some aspects, herein provided is a method for high throughput evaluation of endogenous genetic regulatory elements of a crop plant and/or coding regions of a crop plant, in a model plant. Each possibility is a different embodiment.

The evaluation includes screening a plant genetic library containing a large collection of altered genetic elements (i.e., regulatory elements or coding regions), which are functionally associated with a reporter gene providing a phenotypic trait, thereby, advantageously allowing in-planta selection of a desired change in expression of the reporter gene and identification of the associated genetic change that was introduced into the regulatory element or coding sequence.

In some embodiments, the method provides a high throughput evaluation of a large collection of altered endogenous genetic elements derived from a desired trait-related gene of a desired crop plant (e.g., soybean, corn, rice).

In some embodiments, the large collection of altered endogenous genetic elements is generated in-vitro using standard molecular biology tools for mutagenesis, advantageously allowing to (i) fully cover the element with mutations with high precision and (ii) transform the collection into a different type of plant, (i.e., a "model plant" such as *Arabidopsis*) which is easier to manipulate and screen.

Advantageously, performing the step of mutagenesis in-vitro allows dissociating/decoupling the genetic element that is derived from the crop plant from its coding sequence, if desired.

Further advantageous is the functional association/coupling of the altered genetic elements with a reporter gene (e.g., herbicide tolerance, visualizing gene such as GFP or similar) that provides an easily detectable phenotypic trait that can be assessed just by applying an herbicide to the plants according to a predetermined cut-off concentration, and/or visualizing the marker expression.

In some exemplified embodiments, using this approach a chimeric pGmppo1-AtPPOX1 gene can be generated (a soybean (*Glycine max*) ppo1 promoter coupled to the *Arabidopsis* (*A. thaliana*) PPOX1 gene).

Creating transgenic model plants, such *Arabidopsis*, hosting large collections of mutated genetic elements derived from a crop plant side-by-side with an easy-to-screen marker such as HT, facilitates large-scale in-planta screen and selection of the genetic change that improves the expression of the trait.

In some embodiments, the method enables a high throughput screening of a desired change in a trait without screening mutations in individual crop plants.

In some embodiments, following the identification of the genetic change in the genetic element that was originally derived from the desired crop plant and was introduced into the model plant, a genetically modified crop plant can be generated using gene editing method, addressing the relevant mutation that was identified.

Therefore, advantageously, the disclosed invention bypasses the inefficient step of screening crop plants for mutations that improves traits.

In some embodiments, the *Arabidopsis* plant of the present disclosure is transgenic with respect to the altered genetic elements that originate from other crop important plants, In some embodiments, the reporter of the present disclosure (e.g., herbicide tolerance) allows assessment of the level of the optimization in live/viable plants. (i.e., no need in staining assay or any destructive step of the plant).

In some embodiments, genetic changes are introduced into the transgenic genetic elements, which are the subject of the screen and derived from a desired target crop plant.

Introducing changes to a sequence of a regulatory element of a gene (and to some extent to its coding sequence) can result in an altered/improved expression pattern of the gene, however, it is not known which of those alternations will result in a desirable expression pattern and how to discover these alternations, which combinatorically can represent a problem of approximately 10,118,250 different sequences to be constructed and screened for a genetic element of 1500 bp.

To overcome or bypass those limitations, in some embodiments, the present disclosure provides a method that advantageously allows screening tens of thousands to millions of individually mutated genetic elements, derived from a crop plant, in *Arabidopsis*. In some embodiments, the use of *Arabidopsis* to host altered genetic elements from a crop plant allows applying a simple mutation-generating assay performed in-vitro, rather than inside the cellular system of the crop plant.

In some embodiments, method of the present disclosure comprises mutagenesis in-vitro thereby allowing any nucleotide can to be mutated. In some embodiments, the method has no off-target effects. In some embodiments, the method results in a genetic element that is truly fully covered with mutation.

The method of the present disclosure advantageously couples the collection of altered genetic elements to a reporter that offers an easy-to-detect phenotypic trait such as the herbicide tolerance trait (HT-trait). In some embodiments, using the HT-trait as a reporter allows an automatic truly large-scale in-planta screening just by applying/spraying the relevant herbicide according to a pre-determined cut off concentration.

In some embodiments by coupling the HT-trait, or similar, to a collection of altered genetic elements of interest, automatic large-scale screening can be applied to any trait-related gene of interest.

For example, in some embodiments the HT-trait, or similar, are advantageous, where an assessment of a trait requires an assessment of the effect on each single individual plant, such as for traits affecting the yield of the plant.

In some embodiments, the reporter gene is the Herbicide Tolerance (HT) related Protoporphyrinogen Oxidase (PPOX1) gene of *Arabidopsis* (AtPPOX1) which leads to the manifestation of a desirable/beneficial phenotypic trait of having enhanced resistance to the PPO-inhibitors, such as, but not limited to: Oxadiazon, Flumioxazin, or Carfentrazone Ethyl, thereby allowing high-throughput screening of model plants manifesting a desired change in expression from an altered regulatory element of any native gene of any desired crop plant that is functionally coupled to the trait.

Therefore, the herein disclosed screen provides a method for in-planta selection and identification of novel genetic elements having optimized activity, which advantageously provide a desired improvement in in-planta level of expression, activity, and/or pattern of expression of any endogenous gene.

Advantageously, the herein disclosed screen utilized the expression of a reporter gene (e.g., an HT gene) for high-throughput screening of regulatory elements (the regulatory element preferably originating from a crop-plant, e.g., the promoter of a drought-related gene) for identification of optimized regulatory elements. The screen may thus be conducted in model plants by monitoring the change in expression of the reporter gene and/or phenotype of the model plant (e.g., increased herbicide tolerance, fluorescence level, etc.), as a result of it being functionally coupled to a specific altered version of the regulatory element.

According to some embodiments, the identified genetic element is optimized for expressing a trait-related gene, e.g., a gene providing Herbicide Tolerance (HT), at a level that provides an advantageous enhancement of the trait, e.g., resistance of a crop plant to an herbicide.

Also, herein disclosed is a crop plant with improved natural Herbicide Tolerance (HT). The gene-edited plant comprises the genetic change to the regulatory element, previously identified by the method, to confer enhanced natural resistance.

According to some embodiments, there is provided a method for in-planta high throughput evaluation of endogenous genetic regulatory elements, the method comprising the steps of: obtaining a nucleic acid encoding a native regulatory element of a trait-related gene, coupling it to a coding sequence of a reporter gene; and wherein the regulatory element is of the crop plant; introducing one or more genetic changes in each of a plurality of copies of the native regulatory element, thereby obtaining a genetic library comprising a large collection of altered regulatory elements; introducing the genetic library into model plants, utilizing high throughput transformation, such that on average each model plant receives a single altered regulatory element; screening the transformed model plants, wherein the screening comprises selecting a model plant having a desired change in the expression level/phenotype of the reporter gene; identifying the one or more genetic changes in the altered regulatory element of the selected model plant. Each possibility is a separate embodiment.

According to some embodiments, the method further comprises modifying the native regulatory element of the trait-related gene of the crop plant, based on the one or more identified genetic changes in the altered regulatory element of the selected model plant.

According to some embodiments, the native regulatory element is located upstream, downstream, or within a coding sequence of the reporter or any combination thereof.

According to some embodiments, the native regulatory element is derived from the crop plant.

According to some embodiments, the reporter gene coding sequence is of the same or different gene as the regulatory element of the trait-related gene.

According to some embodiments, the native regulatory element is a promoter or a fragment thereof.

According to some embodiments, the method further comprises applying an algorithm to predict putative hotspots in the native regulatory element, and wherein introducing one or more genetic changes comprises targeting the one or more genetic changes to the hot-spots.

According to some embodiments, the genetic changes comprise alterations directed to random regions of the regulatory element, to the predicted hot-spots, and/or a combination thereof.

According to some embodiments, the one or more genetic changes are selected from one, or more point mutations, domain swapping, rearrangement of cis-elements, enhancers addition and/or deletion of silencers.

According to some embodiments, introducing the genetic library into model plants comprises cloning into *Agrobacterium* binary vectors.

According to some embodiments, the screening of a model plant having the desired change in the expression level of the reporter gene comprises meeting a pre-determined cut-off.

According to some embodiments, the desired change in the expression level/phenotype of the trait-related gene/reporter gene comprises a change in transcription activity of the altered regulatory element.

According to some embodiments, the desired change in the expression level/phenotype of the trait-related gene/reporter gene comprises change/s in time, development stage, cellular localization, tissue specific and/or strength of expression of the reporter gene.

According to some embodiments, the desired change in the expression level of the trait-related gene/reporter gene comprises an increased expression associated with increased gene function and/or activity.

According to some embodiments, the increased function and/or activity of the trait-related gene/reporter gene confers enhanced plant resistance or enhanced plant yield.

According to some embodiments, the enhanced resistance comprises tolerance to herbicides, insects, diseases, heat, drought, biotic or abiotic stress.

According to some embodiments, the enhanced resistance comprises herbicide tolerance (HT).

According to some embodiments, the herbicide tolerance (HT) comprises increased expression of a native enzyme that overcomes the herbicide's active ingredient concentration in the plant thereby increasing natural resistance.

According to some embodiments, the native enzyme is Protoporphyrinogen Oxidase (PPO1), or p-hydroxyphenylpyruvate dioxygenase (HPPD), or 5-enolpyruvylshikimate 3-phosphate synthase (EPSPS), or Glutamine synthase, or acetolactate synthase (ALS enzyme), or 7,8-dihydropteroate synthase, acetyl-CoA carboxylase (ACCase) or any combination thereof. Each possibility is a separate embodiment.

According to some embodiments, the desired crop plants are generated using gene-editing tools.

According to some embodiments, there is provided a gene edited crop plant or crop plant cell comprising a modified regulatory element of a trait-related gene, wherein the modification of the regulatory element trait-related gene of the crop plant is based on the one or more genetic changes identified in the altered regulatory element of the selected model plant associated with the desired change in the expression level of the reporter gene, as identified in the method disclosed herein.

According to some embodiments, there is provided a gene edited crop plant or crop plant cell comprising a modified genetic element comprising a coding sequence of a trait-related gene, wherein the modification of the genetic element comprising the coding sequence of the trait-related gene of the crop plant is based on the one or more genetic changes identified in the altered genetic element comprising coding sequence of the selected model plant associated with the desired change in the expression level of the reporter gene, as identified in the method disclosed herein.

According to some embodiments, the gene-editing results in an increased expression of a native enzyme that increases a natural resistance of the plant to the herbicide.

According to some embodiments, the native enzyme is Protoporphyrinogen Oxidase (PPO1), or p-hydroxyphenylpyruvate dioxygenase (HPPD), or 5-enolpyruvylshikimate 3-phosphate synthase (EPSPS), or Glutamine synthase, or acetolactate synthase (ALS enzyme), or 7,8-dihydropteroate synthase, acetyl-CoA carboxylase (ACCase) or any combination thereof. Each possibility is a separate embodiment.

According to some aspects, there is provided a construct comprising a genetically modified promoter of a trait-related gene of a plant coupled to and functionally associated with an Herbicide Tolerance (HT) gene.

According to some embodiments, the genetically modified promoter is derived from an endogenous promoter of a trait-related gene of a plant.

According to some embodiments, the genetically modified promoter is derived from an endogenous promoter of a crop plant.

According to some embodiments, the Herbicide Tolerance (HT) gene is exogenous to the crop plant.

According to some aspects, there is provided a gene edited crop plant or crop plant cell comprising a ppo1 promoter genetically modified to include one or more mutations in one or more positions corresponding to any one or more of positions: −1229 A, −1105 T, −668 A, −481 T, −189 A, −70 T, and −61 T of the soybean promoter as set forth in SEQ ID NO: 2.

In some embodiments, there is provided a gene edited crop plant or crop plant cell, wherein the crop plant is soybean.

In some embodiments, the gene edited crop plant or crop plant cell, wherein the one or more mutations include substitution, addition and/or deletion.

In some embodiments, the gene edited crop plant or crop plant cell, wherein the one or more mutations comprising one or more of: −1229 A>C, −1105 T>C, −668 A del, −668 A>G, −481 T>G, −189 ins A, −189 A>C, −189 A del, −70 T>C, and −61 T>G.

In some embodiments, the gene edited crop plant or crop plant cell, wherein the one or more mutations comprise at least two mutated positions.

In some embodiments, the gene edited crop plant or crop plant cell, wherein the ppo1 promoter having at least 90% sequence identity to SEQ ID NO: 2, In some embodiments, the gene edited crop plant or crop plant cell, wherein the ppo1 promoter comprises the sequence set forth in any one of SEQ ID NOs: 4-13.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

The invention will now be described in relation to certain examples and embodiments with reference to the following illustrative figures so that it may be more fully understood.

FIG. 1A illustrates the cloning of Arabidopsis (A. thaliana) Protoporphyrinogen Oxidase coding sequence (AtPPOX1) downstream to the soybean (Glycine max) Protoporphyrinogen Oxidase promoter sequence (pGmppo1), thereby creating a chimeric pGmppo1-AtPPOX1 sequence. FIG. 1B illustrates the cloning of soybean Protoporphyrinogen Oxidase coding sequence (GmPPO1) together with its promoter pGmppo1, creating the native sequence of soybean PPO1 gene pGmppo1-GmPPO1.

FIG. 31D Analysis of mutation distribution revealed by functional herbicide selection assay. Each line represents the genetic changes (mutations) found in the sequence of the pGmppo1 promoter region in an individual selected event. Each dot denotes the position of a mutation. A full dot denotes a mutation that was detected in more than one event. Empty dot denotes a substitution mutation, X denotes deletion mutation. V denotes insertion mutation.

DETAILED DESCRIPTION

Figure 1A:
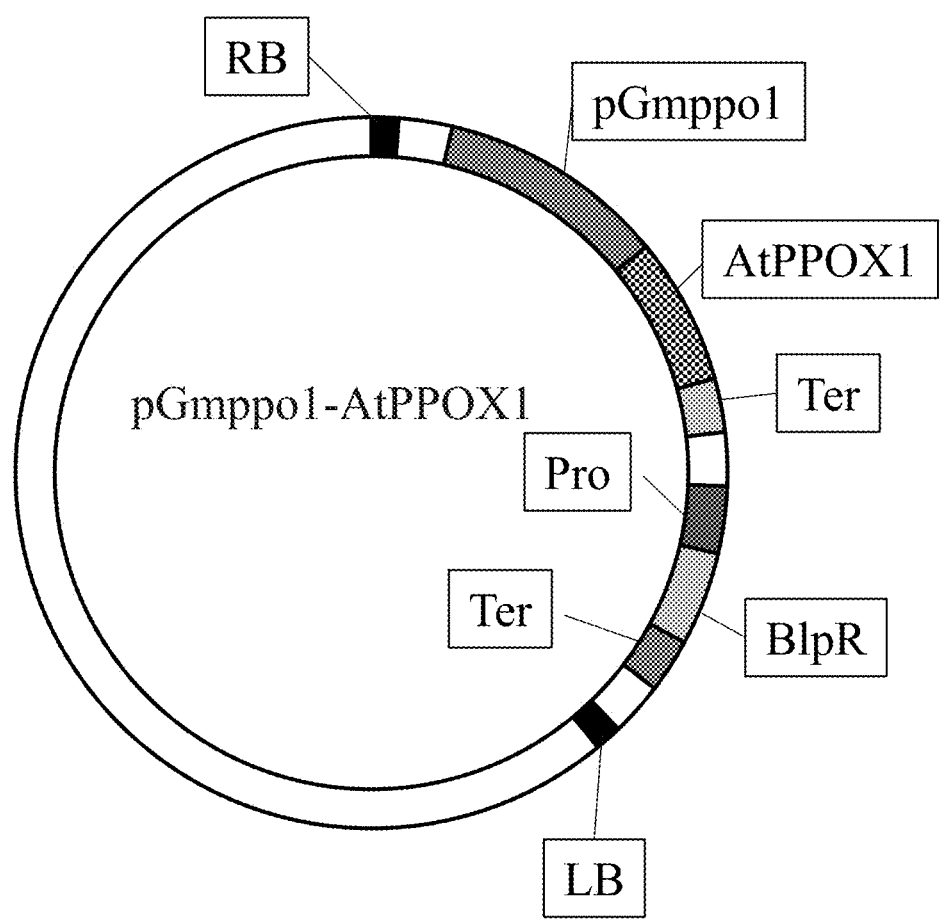
FIG. 1A-FIG. 1B present illustrations of the different components of the binary vector backbone (pPA35H) that is used for cloning of the regulatory element and/or coding sequences of the Protoporphyrinogen Oxidase (PPO1) gene. RB and LB are right and left border recombination sites, respectively. BlpR is the Bialaphos resistance gene used as a positive selection marker for plant transformation. Pro is the promoter site. Ter is the terminator site.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

For convenience, certain terms used in the specification, examples, and appended claims are collected here. Unless otherwise defined, all technical and scientific terms used herein have the same meaning as commonly understood by one of ordinary skill in the art to which it pertains.

Definitions

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As used herein, a "plant" refers to any plant at any stage of development, including a plant seed. the term "plant" includes the whole plant or any parts or derivatives thereof, such as plant cells, plant protoplasts, plant cell tissue culture from which plants can be regenerated, plant callus or calli, meristematic cells, microspores, embryos, immature embryos, pollen, ovules, anthers, fruit, flowers, leaves, branches, stems, cuttings, cotyledons, pistil, seeds, seed coat, roots, root tips and the like.

As used herein, the term "crop plant" and "crop" may be used interchangeably and refer to any plant that can be grown and harvested extensively for profit or subsistence. Crops may refer either to the harvested parts or to the harvest in a more refined state. Most crops are cultivated in agriculture or aquaculture. A crop may include macroscopic fungus (e.g. mushrooms), or macroscopic marine algae (e.g. seaweed). Most crops are harvested as food for humans or fodder for livestock. Some crops are gathered from the wild (including intensive gathering, e.g. ginseng, yohimbe, eucommia). Important non-food crops include horticulture, floriculture, ornamentals, forest trees and plants, and industrial crops. Horticulture crops include plants used for other crops (e.g. fruit trees). Floriculture crops include bedding plants, houseplants, flowering garden, and pot plants, cut cultivated greens, and cut flowers. Industrial crops are produced for clothing (fiber crops e.g. cotton), biofuel (energy crops, algae fuel), or medicine (medicinal plants).

As used herein, the term "model plant" may refer to any plant that typically is from an extensively studied plant species chosen for the ease of investigating particular biological phenomena. The model plants provide biological insights relevant to other plants such as crop plants. According to some embodiments, the crop plant may be a model plant.

As used herein, the term "native" refers to endogenous sequences naturally found in plants. The terms "native", "naturally", and "endogenously" may be interchangeably used.

For example, as used herein, in some embodiments, the native sequence is any endogenous gene or segment of a DNA naturally found in plants. In some embodiments, the native sequence is an endogenous regulatory element naturally found in a plant. In some embodiments, the native sequence is an endogenous coding region naturally found in a plant.

As used herein, the terms DNA "regions", DNA "segments", DNA "sequences", and DNA "elements" may be interchangeably used and refer to a part of a DNA.

As used herein, the term "a part of the DNA" refer to any part of the DNA whether it is a non-coding segment of a DNA or a coding segment of a DNA.

As used herein, the term "non-coding sequences" may refer to regulatory elements, such as, but not limited to, a promotor and/or an enhancer. According to some embodiments, the non-coding sequence may be a 5' or 3' UTR of the gene. According to some embodiments, the non-coding sequence may be an intron.

As used herein, the term "coding sequence" may refer to the part of the gene encoding a functional transcript and/or a protein. The coding sequence include the untranslated regions (UTRs) and the protein translated region (reading frame). The term "coding sequences" and "coding region" may be used interchangeably.

As used herein, the term "trait" refers to the phenotype derived from a particular sequence or groups of sequences. A phenotypic trait has detectable characteristics that may be measured. As used herein, the term "trait" or "phenotypic trait" may be interchangeably used. A trait may be derived from a native sequence or not.

As used herein, a trait confers an improved characteristic to the plant, such as an attribute that is desirable/beneficial.

In accordance, as used herein, the term "trait-related sequence" or "trait-related gene" refers to the gene(s)/genotype(s) the trait is derived from or affected by. The terms "trait-related sequence" and "trait-related gene" may be interchangeably used and may refer to the DNA coding sequence of the gene or to the functional product of that gene that is generated (i.e., transcribed and/or translated) based on that coding sequence. A trait-related gene may be native or not.

According to some embodiments, the trait-related gene is of a crop plant.

For example, as used herein in the context of the present invention, in some embodiments, a trait confers an improving characteristic that is an industrially desirable/beneficial attribute includes, but is not limited to, resistance to herbicides, insects, and disease or other biotic stress, tolerance to heat, drought, or other abiotic stress, reduced time to crop maturity, enhanced yield, improved fertilizer uptake, improved industrial processing, such as for the conversion of starch or biomass to fermentable sugars, and improved agronomic quality, such as high oil content and high protein content. Each possibility is a separate embodiment.

As used herein, the term "reporter gene" may refer to a coding sequence to which a regulatory element is functionally coupled and the expression of which may be monitored, thereby enabling evaluation of the effectiveness of the regulatory element in bringing about expression of the reporter gene. According to some embodiments, the reporter gene may be a trait-related gene, e.g. an herbicide tolerance (HT) gene. According to some embodiments, the reporter gene may be a exogenous gene, not normally expressed in plants, such as, but not limited to, GFP.

According to some embodiments, the reporter gene and the trait related gene are of the same or different genes.

Non-limiting examples of a reporter gene include a herbicide tolerance gene, GFP, RUBY (red betalain).

According to some embodiments, the reporter gene enables assessment in a live and/or viable plant.

According to some embodiments, the reporter gene provides color. According to some embodiments the intensity of the color correlates with the level of improvement/optimization/enhancement of the trait or of the natural resistant provided by the trait. each possibility is a separate embodiment.

As used herein, the term "tolerance" and "resistance" may be interchangeably used.

For example, as used herein in the context of the present invention, in some embodiments, high expression levels of the plant's native trait-related gene Protoporphyrinogen Oxidase (PPO1) lead to the manifestation of a desirable/beneficial crop plant trait of herbicide tolerance (HT), as the enzymatic activity of the gene may overcome herbicidal activity thereby conferring resistance to a PPO inhibitor type herbicides (Group 14, which includes the active groups: Diphenylethers, N-phenylphthalimides, Thiadiazoles, Triazolinones, N-phenyloxadiazolones, Phenylpyrazole) such as flumioxazin, oxadiazon, fomesafen, fluthiacet, carfentrazone, sulfentrazone, or others.

Another example, as used herein in the context of the present invention, in some embodiments, the trait evaluated may be that of a reporter such as fluorescence, luminescence, or other state-of-the-art molecular reporters used for screening purposes during research and development. Once a desired expression level of the reporter is achieved, the changes to the regulatory element identified as being attributable to the desired expression level may be implemented with regard to an endogenous gene.

Another example, as used herein in the context of the present invention, in some embodiments, the expression of the non-native trait-related sequence of Green Fluorescent Protein (GFP) leads to the manifestation of a phenotypic trait of having a detectable fluorescent signal.

As referred to herein, affecting or changing the "expression level" of a trait, or of a trait-related gene includes a decrease or increase in the strength of the expression, efficiency of activity/function, as well as a change in the pattern of expression of the trait. As referred to herein affecting or changing the "pattern of expression" of a gene include change(s) in time, development stage, cellular localization, tissue-specific and/or strength of expression As used herein, the terms "a desired change in the expression of a trait" or "a desired change in the expression of a trait-related gene" may be interchangeably used, and refer to the optimization of the level, pattern of expression and/or activity/function of a trait-related gene or a trait, in planta.

As used herein, in some embodiments, the optimized level includes an increase or decrease in the strength of expression of the trait, or the trait-related gene. In some embodiments, the optimized pattern includes a change in the pattern of expression of the trait, or the trait-related gene including change(s) in time, development stage, cellular localization, tissue-specific expression and/or strength of expression. Each possibility is a separate embodiment. In some embodiments, the optimized function/activity includes changes in enzymatic activity, structural activity, signaling, ligand binding functions or reporter activity. Each possibility is a separate embodiment.

According to some embodiments, the term "a desired change in the expression of a trait" or "a desired change in the expression of a trait-related gene/reporter gene" refers to the optimization of the transcription activity of endogenous genetic regulatory elements and includes changes in transcription activity due to altered regulatory elements.

According to some embodiments, the term "a desired change in the expression of a trait" or "a desired change in the expression of a trait-related gene/reporter gene" refer to the optimization of the coding sequence and includes changes in function/activity of the gene product due to altered coding sequence elements.

The desired change in the expression level, pattern and/or activity/function of the trait-related gene includes meeting a pre-determined cut-off for screening and selecting plants introduced with genetic changes in native regulatory elements and/or in coding sequences. The cut-off for the selection of altered genetic elements (regulatory elements or coding sequences) is pre-determined in respect to the element they originated from.

As used herein, the term "pre-determined cut-off" refers to the screening process of individual plants manifesting a desired change in the expression level of a trait. A pre-determined cut-off is determined by exposing plants transformed with a genetic element to selection conditions that include a gradual change in the strength and/or intensity of the "selection condition" and selection based on a "selection criteria". The cut-off may be predetermined, e.g. resistance to a predetermined level of herbicide, or experimentally set (e.g. according to a lethal dose experiment). The cut-off is then set for screening and selection of plants harboring altered genetic elements (altered regulatory elements or altered coding sequences) for manifesting the desired expression level of the trait. Accordingly, the cut-off for the selection of a regulatory element is preferably pre-determined vis-a-vis the element from which it originated. According to some embodiments, meeting the pre-determined cut-off represents a comparison of the expression level obtained between a plant having an altered genetic element to the plant having the native genetic element they originated from.

As used herein, the term "selection conditions" refers to the conditions of inducing stress for the purpose of selection. In some embodiments, the selection is of a desired expression of a trait. Non-limiting examples of selection conditions include plant growth conditions that include: an herbicide for herbicide tolerance, a pesticide for pesticide tolerance, higher than normal concentrations of salt for selection of salinity tolerance, higher than normal osmotic stress for drought resistance, high temperature for tolerance against extreme heat, a source of stimulation or induction of activity for a molecular reporter such as substrate molecule or source of excitation, etc. Each possibility is a separate embodiment.

As used herein, in some embodiments, when screening for a trait of herbicide tolerance (HT), the selection condition may be set by inducing growth conditions of stress using increasing concentrations or with a pre-determined cut-off concentration of PPO inhibitor type herbicides (Group 14, includes the active groups: Diphenylethers, N-phenylphthalimides, Thiadiazoles, Triazolinones, N-phenyloxadiazolones, Phenylpyrazole) such as flumioxazin, oxadiazon, fomesafen, fluthiacet, carfentrazone, sulfentrazone, or others.

As used herein, "selection criteria" refers to the conditions set for detecting and/or measuring the phenotypic trait. Non-limiting examples of selection criteria include: any signal originated from a molecular reporter, turgor pressure, plant death, leaf area, plant shoots fresh weight, leaf number, chlorophyll content, sugar content, protein content, color of organs, branch fresh weight, main branch length, flowers yield, pods or fruits yield, chlorosis, damage to leaves, state or performance of plants and any combination thereof. Each possibility is a separate embodiment.

As used herein, in some embodiments, when screening for a trait of a fluorescent reporter signal the selection criteria is set to detect a gradual change in fluorescence signal or a pre-determined cut-off of fluorescent signal.

As used herein, the term "transcription activity" refers to any event of initiation of transcription which may be modified or regulated by DNA binding proteins, such as RNA polymerases, transcription factors and other transcription-related proteins or protein complexes.

As used herein, the term "other transcription-related proteins or protein complexes" refers to any protein or protein complex having an activity or function that affects the transcription activity of a gene and involves direct or indirect binding or interaction with a DNA regulatory element. Non-limiting examples of transcription-related proteins or protein complexes include RNA polymerases, general and specific transcription factors and transcription co-factors, cis-acting factors, trans-acting factors, transcription activators, transcription suppressors, mediators, modulators, transcription preinitiation complex (PIC). Each possibility is a separate embodiment.

As used herein, the term "hot-spot" refers to specific sites within a regulatory element that are of particular importance in regulating the binding of DNA-binding proteins that takes part in the process of transcription. These include transcription factors and other transcription-related proteins that interact with the DNA in a sequence-specific manner. According to some embodiments, the hot-spots may be identified by applying dedicated hot-spot identification algorithms. In some embodiments, hot-spots may be identified by in-planta functional screening of randomly mutated genetic elements and identification of, for example, resistant event showing improved HT tolerance, as exemplified in Example 5.

As used herein, the term "genetic elements" refers to segments of a polynucleotide DNA molecule and includes both non-coding (i.e., regulatory) and coding sequences.

As used herein, the term "genetic regulatory elements" refers to segments of a polynucleotide DNA molecule capable of changing the expression level and/or expression pattern of specific genes, thereby controlling gene expression. As referred to herein, regulatory elements are sequences of non-coding DNA that bind proteins such as transcription factors and other transcription-related proteins and protein complexes that regulate the signal transmitted to the promoters associated with genes, thereby affecting the transcription activity of the gene and changing the associated expression of the product of the gene.

According to some embodiments, the native regulatory element is of a trait-related gene of a crop plant. According to some embodiments, the native coding sequence is of a trait-related gene of a crop plant.

As used herein, in some embodiments a regulatory element is up to approximately 5 base pairs (bp) long, up to approximately 10 base pairs (bp) long, up to approximately 50 base pairs (bp) long, up to approximately 100 base pairs long (bp), or up to approximately 500 base pairs (bp) long, or up to approximately 1000 base pairs (bp) long, or up to approximately 5000 base pairs (bp) long. Each possibility is a separate embodiment.

In some embodiments, the regulatory element is located within the promoter region of a gene, upstream to the transcribed region of the affected gene. In some embodiments, the regulatory element is located downstream of the transcribed region of the affected gene. In some embodiments, the regulatory element is located within the transcribed region of the affected gene. In some embodiments, the regulatory element is located within the 5' or 3' UTR of a gene. In some embodiments, the regulatory element is located within the intron of a gene.

As used herein, in some embodiments a regulatory element is located up to approximately 10 base pairs (bp) away from the transcription start site (TSS), up to approximately 100 base pairs (bp) away from the TSS, up to approximately 500 base pairs (bp) away from the TSS, up to approximately 1,000 base pairs (bp) away from the TSS, up to approximately 5000 base pairs (bp) away from the TSS, or up to approximately 10,000 base pairs (bp) away from the TSS, or up to approximately 50,000 base pairs (bp) long. In some embodiments, a regulatory element is located on a different molecule than the TSS. Each possibility is a separate embodiment.

A regulatory element acts in cis or in trans to regulate the signal transmitted to the promoters associated with genes.

As used herein, the term "trans-regulatory elements" (TREs) refers to regulatory elements that modify or regulate the expression of un-adjacent genes. In some embodiments, trans-regulatory elements are located on a different molecule than the gene whose transcription they regulate.

As used herein, the term "cis-regulatory elements" (CREs) refers to regulatory elements that modify or regulate the expression of genes in their close vicinity. In some embodiments, cis-regulatory elements are located within the core, proximal or distal promoter. In some embodiments, cis-regulatory elements are located within the transcribed region of the gene they regulate, in some embodiments, cis-regulatory elements are located downstream to the gene they regulate.

As used herein, the term "promoter" refers to a non-coding sequence of DNA to which proteins bind in order to initiate transcription and further regulate the level and/or pattern of expression of an RNA transcript from the DNA downstream of the promoter. Promoters are located upstream to the transcription start site (TSS) of genes on the DNA towards the 5' region of the transcribed strand.

As used herein, the terms "promoter" and "regulatory elements" may be used interchangeably in relation to DNA sequences or fragments that control the transcription process and the expression level and/or pattern of a gene in a sequence-dependent manner by binding proteins engaged in transcription, such as transcription factors and other transcription related-proteins. According to some embodiments the regulatory element may be a naturally occurring regulatory element e.g. of a plant or other organism. According to some embodiments, the regulatory element may be a synthetic regulatory element, not naturally found.

In accordance, as used herein, in some embodiments, the typical architecture of a plant gene includes regulatory elements comprising promoters. In some embodiments, the typical architecture of a plant gene includes promoters comprising regulatory elements.

In some embodiments, the promoters consist of a proximal promoter (including a core promoter) and a distal promoter.

As used herein, the term "proximal promoters" refers to regulatory elements located near the transcription start site of a gene. In some embodiments, proximal promoters are up to approximately 100 base pairs (bp) long, up to approximately 250 base pairs (bp) long, up to approximately 500 base pairs (bp) long, up to approximately 1000 base pairs long (bp), or up to approximately 1500 base pairs (bp) long, or up to approximately 2000 base pairs (bp) long. Each possibility is a separate embodiment.

Proximal promoters include the "core promoter" of a gene, a term used herein to describe the minimal portion of the proximal promoter required to properly initiate transcription. In some embodiments, core promoters are located around the TSS and may extend into the transcribed region. In some embodiments, core promoters may include a regulatory element that extends up to approximately several dozen bp into the transcribed region, a non-limiting example of such a regulatory element that extends into the transcribed region is a downstream promoter element (DPE).

In accordance, as used herein, the terms "core promoter" and "proximal promoter" may be used interchangeably in relation to regulatory elements located near the TSS.

Non-limiting examples of regulatory elements of proximal and core promoters include cis-regulatory elements, TATA box, initiator sequences (INRs), downstream promoter elements (DPEs), E-box, upstream activator sequence (UAS), and Response Elements (RE). Each possibility is a separate embodiment.

As used herein, the term "distal promoters" refers to regulatory elements located up to approximately several kilobases or up to approximately several dozens of kilobases away from the transcriptional start site. In some embodiments, the distal promoter contains cis regulatory elements (CREs) that can function as transcription enhancers and also perform an accessory role in increasing the transcriptional activity of enhancers. In some embodiments, domain swapping, rearrangement of cis-elements, and combining cis-regulatory elements from different promoters have a considerable effect on transcription levels. Non-limiting examples of regulatory elements of distal promoters include cis-regulatory elements, enhancers, silencers, and insulators.

In some embodiments, the regulatory element is an enhancer. As used herein, the term "enhancer" refers to a regulatory element that upregulates the overall expression of the gene by binding transcription activators that facilitate the formation of the transcription pre-initiation complex at the core promoter region. In some embodiments, enhancers can also bind transcription repressors that reduce the overall expression of the gene by competing with the binding of activators to the enhancer thereby preventing the formation of the pre-initiation complex. In some embodiments, enhancers regulate the expression level and/or expression pattern.

In some embodiments, the regulatory element is a silencer. As used herein, the term "silencer" refers to a regulatory element, such as but not limited to insulators, that downregulates the overall transcription of the gene by preventing enhancers from acting on the promoter of a gene. In some embodiments, silencers regulate the expression level and/or expression pattern.

As used herein, the term "native regulatory element" refers to endogenous regulatory sequences naturally found in the plant. The terms, "native regulatory elements", "natural regulatory elements", and "endogenous regulatory elements" may be interchangeably used.

As used herein, the term "native genetic element" refers to endogenous regulatory sequences naturally found in the plant or to coding sequence thereof.

Figure 2A:
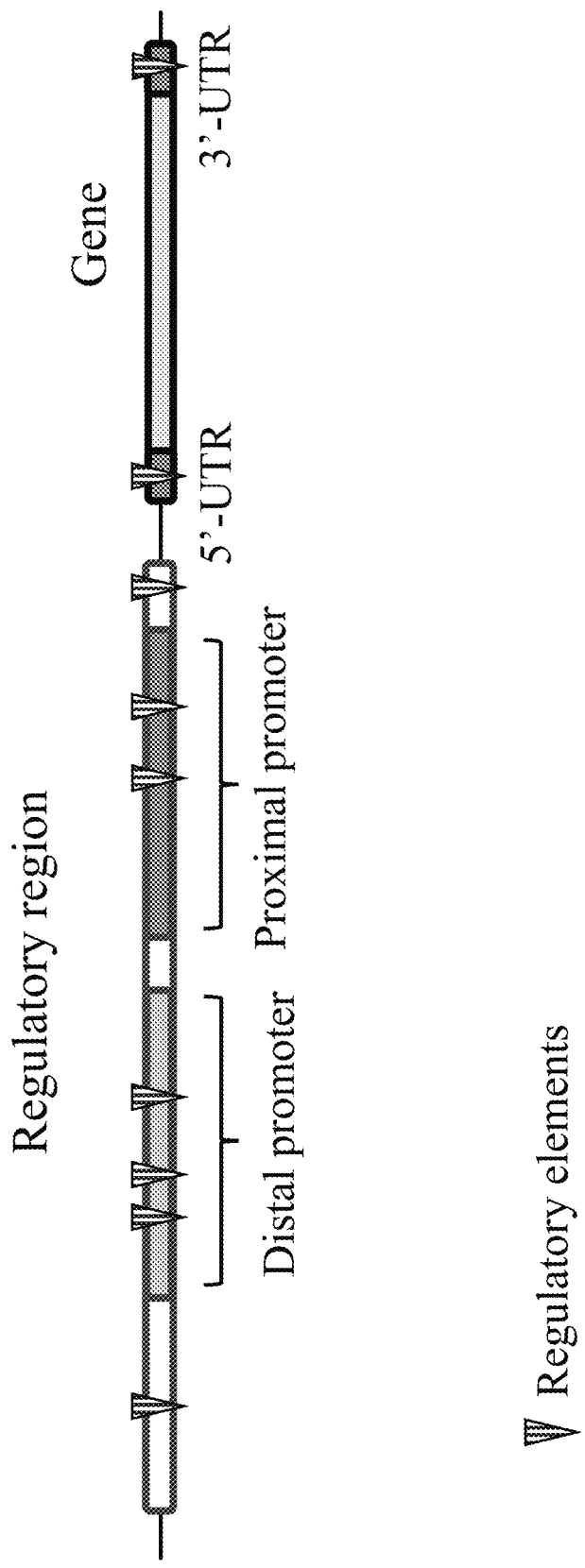
FIG. 2A illustrates the general architecture of a plant gene having regulatory region/element and coding regions/sequence. Regulatory elements may be located upstream in proximal and distal promoter regions and may act in cis or trans to influence the level of expression of the gene. Regulatory elements may also be located within the coding region/sequence of the gene in its untranslated regions (5'-UTR and 3'-UTR). Genetic alteration may be introduced to the regulatory region/element and/or to the coding regions/sequence.

Reference is now made to FIG. 2A showing a plant gene structure.

According to some embodiments, a native genetic regulatory element from one kind of plant may be coupled upstream to a trait-related gene and/or reporter gene of a different kind of plant. In some embodiments, a native genetic regulatory element, e.g., from soybean (*Glycine max*), may be coupled to a trait-related sequence/reporter sequence from *Arabidopsis* (*A. thaliana*). In some embodiments, a native promoter of for example soybean (pGmX) may be cloned upstream to a native herbicide tolerance (HT)-related gene such as Protoporphyrinogen Oxidase (PPOX1) of *Arabidopsis* (AtPPOX1), producing a soybean-*Arabidopsis* chimera (pGmX-AtPPOX1) clone. Differently, in some embodiments, a native promoter of soybean (pGmX) may be cloned upstream to a sequence encoding a coding sequence of a reporter gene, for example, GFP, producing a non-native (pGmX-GFP).

As used herein, the term "altered genetic element(s)" refers to a polynucleotides sequence that was manipulated by any method known in the art commonly used to introduce genetic changes into a nucleic acid sequence, thereby producing new sequences comprising alteration with respect to the native genetic element it was originated from. As used herein, an altered nucleic acid comprises at least one or more genetic changes to the polynucleotide in respect to the copy of the native genetic element it was originated from.

As used herein, in some embodiments the altered genetic regulatory element(s) refers to genetic changes introduced to regulatory elements, thereby producing new sequences comprising alteration with respect to the original copy of the native regulatory element it was originated from.

As used herein, in some embodiments the altered genetic element(s) refers to a genetic element that includes changes that were introduced to the coding sequences regions, thereby producing new coding sequences/region comprising alteration with respect to the original copy of the native coding element it was originated from.

In some embodiments, a desired change in gene expression of the trait-related gene/reporter gene comprise genetic alteration introduced to the regulatory region/element and/or to the coding regions/sequence. Each possibility is a separate embodiment.

In some embodiments, introducing one or more genetic changes in each of a plurality of copies of the native coding sequence, thereby obtaining a genetic library comprising a large collection of altered coding regions.

In some embodiments, genetic changes comprise alterations directed to random regions of the coding sequence. In some embodiments, genetic changes comprise alterations directed to random regions of the protein translated sequence/protein reading frame.

Figures 2B, 2C:
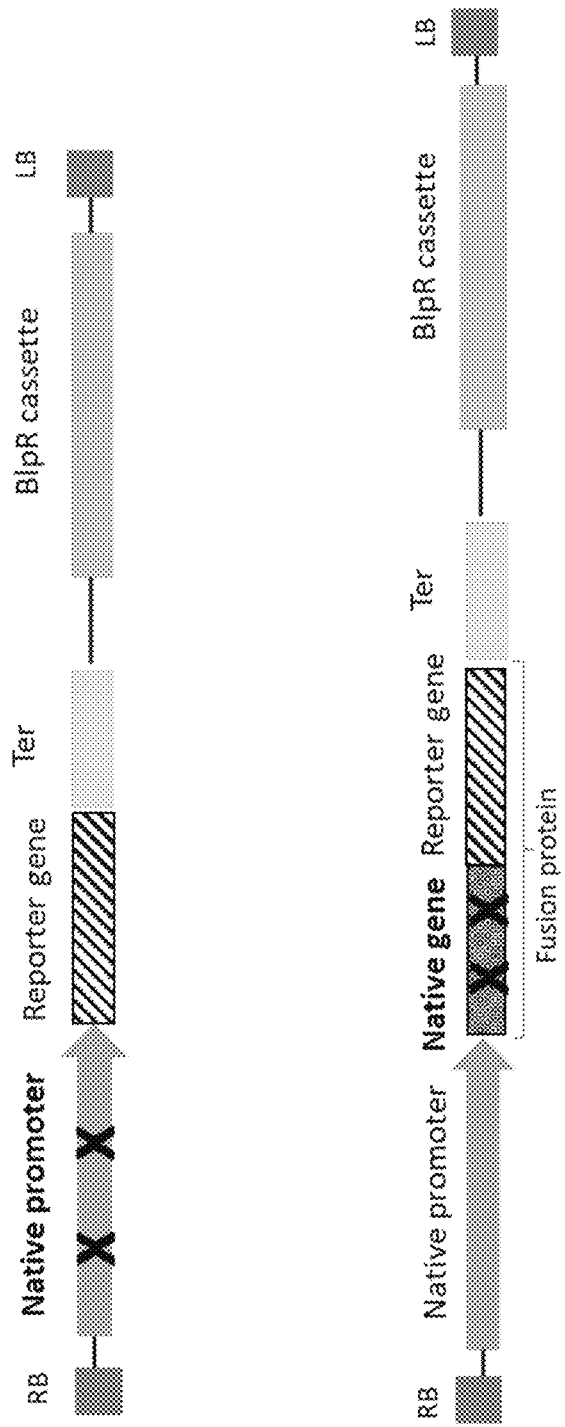
FIGS. 2B-2C illustrates genetic elements of a trait-related gene cloned into the binary vector and carrying mutated sequences (marked as X) in the promoter regulatory element (FIG. 2B) or in the protein translated region within the coding sequence (FIG. 2C). Where optimizing the level of expression of the trait-related gene is performed by targeting the translated product, the mutations are introduced into in the coding region and the translated protein product may be expressed as a fusion protein, fused to a reporter gene as illustrated in FIG. 2C.

Reference is now made to FIGS. 2B-2C showing possible regions for introduction of genetic alterations.

As used herein, the terms "changed", "altered", "manipulated", "edited" may be interchangeably used.

Non-limited examples for genetic changes include one, or more, point mutations (deletion, substitution and/or addition), domain swapping, rearrangement of cis-elements, enhancers addition and/or deletion of silencers, changes that can affect elements in cis or trans. Each possibility is a separate embodiment.

Non-limited examples of methods of introducing genetic changes to a nucleic acid sequence include site-specific mutagenesis (site-directed mutagenesis), chemically or biologically induced random mutagenesis, gene editing methods, recombination, restrictions-ligations, solid phase synthesis. Each possibility is a separate embodiment.

As used herein, the term "editing" or "gene-editing" refers to any method known in the art commonly used to direct and introduce a specific change in a specific locus to nucleic acid sequence, for example, using engineered nucleases such as meganucleases, zinc finger nucleases (ZFNs), transcription activator-like effector-based nucleases (TALEN), or clustered regularly interspaced short palindromic repeats (CRISPR). Each possibility is a separate embodiment.

The terms "genetically modified" (GM), "genetic modification" (GM) or "genetically modified organism" (GMO) may be interchangeably used.

The terms "gene function" and "gene activity" may be interchangeably used and refer to any cellular function and/or activity a functional gene product or a protein may be involved in. Non-limiting examples of cellular functions of proteins includes enzymatic activity, structural functions, cell signaling and ligand binding.

As used herein, the terms "massively parallel", "high throughput" and "large scale" may interchangeably be used and relate to the simultaneous transformation and screening of at least 50, at least 100, at least 500, at least 1000, at least 10,000 or at least 100,000 changed genetic regulatory elements or coding sequences. Each possibility is a separate embodiment.

As used herein, the term "evaluation" refers to the process of screening and identifying regulatory elements for having a desired change in transcription that is associated with a desired change in expression and/or activity of the product of the trait-related gene they are coupled to, by any one of the methods herein described by this invention.

As referred to herein, the terms "polynucleotide molecules", "oligonucleotide", "polynucleotide", "nucleic acid", and "nucleotide" sequences may interchangeably be used. The terms are directed to polymers of deoxyribonucleotides (DNA), ribonucleotides (RNA), and modified forms thereof in the form of a separate fragment or as a component of a larger construct, linear or branched, single stranded (ss), double stranded (ds), triple stranded (ts), or hybrids thereof. Accordingly, as used herein, the terms "polynucleotide molecules", "oligonucleotide", "polynucleotide", "nucleic acid" and "nucleotide" sequences are meant to refer to both DNA and RNA molecules. As used herein, a "nucleotide" includes a nitrogenous base, a sugar molecule, and a phosphate group. A nucleic acid may include naturally occurring nucleosides (e.g., adenosine, thymidine, guanosine, cytidine, uridine, deoxyadenosine, deoxythymidine, deoxyguanosine, and deoxycytidine). The terms further include oligonucleotides composed of naturally occurring bases, sugars, as well as oligonucleotides having non-naturally occurring portions, which function similarly to respective naturally occurring portions. As used herein, nucleotides (A, G, C or T) and nucleotide sequences are marked in lower-case letters (a, g, c or t). As used herein, the term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g. by DNA replication or transcription of DNA or RNA, respectively). DNA and RNA can also be chemically synthesized.

As used herein, the terms "approximately" or "about" in reference to a number are generally taken to include numbers that fall within a range of 5% or in the range of 1% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

As used herein, the singular forms "a," "an" and "the" include plural referents unless the context clearly dictates otherwise.

As used herein, "optional" or "optionally" means that the subsequently described event or circumstance does or does not occur, and that the description includes instances where said event or circumstance occurs and instances where it does not.

As used herein, the term "average" refers to the mean value as obtained by measuring a pre-determined parameter in any group of measured data or each plant of a certain plant population and calculating the mean value according to the number of plants in the said population.

According to some aspects, herein provided is a method for in-planta high throughput evaluation of endogenous genetic regulatory elements.

In some embodiments, the plant is a crop plant and/or a model plant.

In some embodiments, the evaluation of endogenous genetic regulatory elements includes screening and identifying a desired change in expression level and/or activity of a trait-related gene and/or reporter gene that is functionally associated with the regulatory element.

In some embodiments, a desired change in expression level and/or activity of a trait-related gene and/or reporter gene includes identifying a change in transcription activity of the altered regulatory element that is functionally associated with the gene.

According to some aspects, herein provided is a method for in-planta high throughput evaluation of endogenous genetic coding elements.

In some embodiments, a desired change in expression level and/or activity of a trait-related gene includes identifying a change in the activity of the functional product of the altered coding element that is functionally associated with the regulatory element.

In some embodiments, the activity of the functional product of the altered coding element includes but is not limited to: enzymatic activity, structural functions, activity in cell signaling, and/or ligand binding.

In some embodiments, the change in expression level and/or activity include a change in the level of strength of the expression and/or the pattern of the expression.

According to some embodiments, the method comprises a step of obtaining a nucleic acid encoding a native regulatory element coupled to a coding sequence of a trait-related gene/reporter gene.

In some embodiments, coupling includes functional association.

In some embodiments, the regulatory element includes a natural regulatory element.

In some embodiments, the regulatory element includes a core promoter, a proximal promoter, a distal promoter, an enhancer, a silencer, an insulator, a cis-acting element, a trans-acting element, a TATA box, an initiator sequences (INRs), a downstream promoter element (DPEs), an E-box, an upstream activator sequence (UAS), and/or a Response Element (RE), or any combination thereof. Each option is an embodiment by itself. Each possibility is a separate embodiment.

In some embodiments, the native regulatory element is a promoter or a fragment thereof.

In some embodiments, the native regulatory element is derived from a crop plant. In some embodiments, the native regulatory element is of any native gene and the coding sequence is of a trait-related gene/reporter gene; in some embodiments, the native regulatory element is of a trait-related gene and the coding sequence is of a trait-related gene/reporter gene.

In some embodiments, in the reporter gene coding sequence is of the same or different origin as the trait-related gene regulatory element.

In some embodiments, the encoded native or altered regulatory element is located upstream to a coding sequence of a trait-related gene and/or reporter gene; in some embodiments, the encoded native or altered regulatory element is located within the transcribed region of a trait-related gene and/or reporter gene; in some embodiments, the encoded native or altered regulatory element is located downstream to a coding sequence of a trait-related gene and/or reporter gene.

In some embodiments, the nucleic acid encodes a regulatory element upstream of a trait-related gene and/or reporter gene and further encodes a regulatory element within and/or downstream to the coding sequence of the trait-related gene and/or reporter gene.

In some embodiments, a trait confers an improving characteristic to the plant.

In some embodiments, improving a characteristic includes inducing/triggering an attribute that is desirable/beneficial; in some embodiments, the desirable/beneficial attribute is an industrially desirable/beneficial attribute.

In some embodiments, the industrially desirable/beneficial attribute includes but is not limited to improved tolerance or resistance of plants and enhanced plants yield.

In some embodiments, a trait of enhanced tolerance or resistance includes, but is not limited to, resistance to herbicides, insects, and diseases or other biotic stress, tolerance to heat, radiation, drought, salinity, cold, hypoxia, or other abiotic stress; in some embodiments, a trait of enhanced yield includes but is not limited to reduced time to crop maturity, changing the architecture of the plant, reduce size, increased size, improved photosynthetic activity, improved fertilizer uptake, improved fertilizer use efficiency, improved health ingredients, improved industrial processing, such as for the conversion of starch or biomass to fermentable sugars, and improved agronomic quality, such as high oil content and high protein content. Each option is an embodiment by itself. Each possibility is a separate embodiment In some embodiments, the trait-related gene is a reporter gene. In some embodiments, the trait-related gene/reporter gene is a native gene derived from plants.

In some embodiments, the trait-related gene/reporter gene is derived from other sources, including, but not limited to, animals, bacteria, fungi, and viruses.

In some embodiments, the trait-related gene is a reporter gene including, but not limited to, fluorescent proteins, luminescent proteins or any biological or agricultural screenable trait, such as, but not limited to, fertility, color, shape, width of plant organ, size of plant organ or tissue, or number of plant organ or tissue.

In some embodiments, the function and/or activity of the trait-related gene being increased confers enhanced plant resistance or enhanced plant yield.

In some embodiments, the enhanced resistance includes tolerance to herbicides, insects, diseases, heat, drought, biotic or abiotic stress.

In some embodiments, the enhanced resistance comprises herbicide tolerance (HT).

In some embodiments, the herbicide tolerance (HT) comprises increased expression of a native enzyme that overcomes the herbicide's active ingredient concentration in the plant thereby increasing natural resistance.

In some embodiments, the native enzyme that overcomes the herbicide's active ingredient concentration in the plant thereby increasing natural resistance is Protoporphyrinogen Oxidase 1 (PPO1), Protoporphyrinogen Oxidase 2 (PPO2), or p-hydroxyphenylpyruvate dioxygenase (HPPD), or 5-enolpyruvylshikimate 3-phosphate synthase (EPSPS), or Glutamine synthase, or acetolactate synthase (ALS enzyme), or 7,8-dihydropteroate synthase, or acetyl-CoA carboxylase (ACCase). Each possibility is a different embodiment.

According to some embodiments, the method comprises the step of introducing one or more genetic changes in each of a plurality of copies of the native regulatory element, thereby obtaining a genetic library comprising a large collection of altered regulatory elements.

In some embodiments, an altered regulatory element includes one or more genetic changes.

In some embodiments, the genetic change comprises at least one or more alterations to the polynucleotide in respect to the copy of the endogenous regulatory element it was originated from.

In some embodiments, genetic alterations are introduced to an original/native regulatory element utilizing at least one or more methods for changing nucleic acids including but are not limited to: site-specific mutagenesis (site-directed mutagenesis), chemically or biologically induced random mutagenesis, gene editing methods, recombination, restrictions-ligations and/or solid-phase synthesis. Each option is an embodiment by itself.

In some embodiments, the altered regulatory element includes, but is not limited to, core promoter, proximal promoter, distal promoter cis-element, and/or trans-element. Each option is an embodiment by itself.

In some embodiments, the regulatory element includes but is not limited to an enhancer, a silencer, an insulator, a TATA box, an initiator sequences (INRs), a downstream promoter element (DPEs), an E-box, an upstream activator sequence (UAS), and/or a Response Element (RE), or any combination thereof. Each option is an embodiment by itself.

In some embodiments, the genetic changes include but are not limited to at least one, or more, point mutations; in some embodiments, the one, or more point mutations are selected from the group consisting of nucleotide deletion, nucleotide substitution and/or nucleotide addition. In some embodiments, the genetic changes include singular or plural changes. Each possibility is a separate embodiment In some embodiments, genetic changes include but are not limited to enhancers addition and/or deletion of silencers.

In some embodiments, the genetic changes include but are not limited to domain swapping, and/or rearrangement of cis-elements, changes can affect elements in cis or trans.

In some embodiments, the mutations are directed to pre-known hot-spots and/or their vicinity within the regulatory element.

In some embodiments, an algorithm is applied to predict putative hot-spots in the native regulatory elements. In some embodiments, the introduction of one or more genetic changes includes targeting the one or more genetic changes to the predicted hot-spots.

In some embodiments, the genetic changes include random mutagenesis, genetic changes to the predicted hot-spots, and/or a combination thereof.

According to some embodiments, the method comprises the step of introducing the genetic library into model plants, utilizing high throughput transformation, such that on average each model plant receives a single altered regulatory element or altered coding region, that could have been changed in single or multiple locations.

In some embodiments, the model plant includes, but is not limited to *Arabidopsis thaliana, Camelina sativa,* or *Nicotiana tabacum.*

In some embodiments, the introduction of the genetic library into model plants includes cloning into *Agrobacterium* binary vectors. In some embodiments, the introduction of the genetic library into model plants includes the use virus and virus libraries with modified genetic elements to inoculate plants. In some embodiments, the introduction of the genetic library into model plants includes the use of "gene-gun" technologies or other transformation methods known in the art.

According to some embodiments, the method comprises the step of screening the transformed model plants, wherein the screening comprises selecting from the plurality of transformed plants, a model plant having a desired change in the expression level of the trait-related gene.

In some embodiment, the desired change in the expression level of a trait, or in the expression level of a trait-related gene includes optimization of the level of strength and/or pattern of expression in planta.

In some embodiments, the optimized level of strength of expression includes an increase or decrease in the strength of expression of the trait; in some embodiments, the optimized level of strength of expression includes an increase or decrease in the strength of expression of the trait-related gene/reporter gene or its activity.

In some embodiments, the optimized pattern of expression includes a change in the pattern of expression of the trait, or the trait-related gene/reporter gene including change(s) in time, development stage, cellular localization, tissue specific and/or strength of expression. each option is an embodiment for itself.

In some embodiments, the desired change in the expression level of the trait-related gene/reporter gene includes an increased expression associated with increased gene function and/or activity; in some embodiments, the desired change in the expression level of the trait-related gene/reporter gene includes a decreased expression associated with decreased gene function and/or activity.

In some embodiments, the desired change in the expression level of the trait, or in the expression level of the trait-related gene/reporter gene includes optimization of the transcription activity of the endogenous genetic regulatory elements functionally associated with it.

In some embodiments, the desired change in the expression level of the trait-related gene/reporter gene includes a change in the transcription activity of the altered regulatory element functionally associated with the gene.

In some embodiments, the desired change in the expression level of the trait, or of the trait-related gene/reporter gene includes meeting a pre-determined cut-off for screening and selecting plants introduced with genetic changes in native regulatory elements.

In some embodiments, the screening of the model plant having the desired change in the expression level of the trait-related gene/reporter gene includes meeting a pre-determined cut-off.

In some embodiments, the pre-determined cut-off is determined by exposing plants transformed with a native genetic element to selection conditions that include a gradual change in strength or intensity of the selection condition and selecting, based on selection criteria.

In some embodiments, the pre-determined cut-off is utilized for screening and selection of plants harboring altered regulatory elements for manifesting the desired expression level of the trait Accordingly, in some embodiments, the cut-off for the selection of the altered regulatory elements is initially pre-determined in respect to the element they originated from.

Accordingly, in some embodiments, meeting the pre-determined cut-off represents a comparison between altered regulatory elements to the native genetic element they originated from.

In some embodiments, the desired change in the expression level and/or activity of the trait-related gene/reporter gene includes a change in the level of strength of the expression; in some embodiments, the desired change in the level of strength of the expression includes a decrease in expression; in some embodiments, the desired change in the level of strength of the expression includes an increase in expression.

In some embodiments, the desired change in expression level and/or activity of a trait-related gene/reporter gene includes a change in the pattern of expression. In some embodiments, the desired change in the pattern of expression of a trait-related gene includes but is not limited to change(s) in time, development stage, cellular localization, tissue-specific, and/or strength of expression. Each option is an embodiment by itself.

According to some embodiments, the method comprises the step of identifying the one or more genetic changes in the altered regulatory element of the selected model plant.

In some embodiments, the identification of the one or more genetic changes in the altered regulatory element is performed using DNA sequencing.

According to some embodiments, the method comprises the step of modifying a regulatory element of a crop plant, based on the one or more identified genetic changes in the altered regulatory element of the selected model plant.

In some embodiments, the modification of a regulatory element of the crop plant is based on the altered regulatory element it originated from; in some embodiments, the modification of a regulatory element of the crop plant is based on the altered regulatory element of a different plant crop.

In some embodiments, the crop plant includes but is not limited to corn, soybean, cotton and canola. Each option is an embodiment by itself.

The method can be applied on any plant species, including, but not limited to, monocots and dicots. Examples of plant species include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), Sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), palm trees from the Arecaceae (e.g, coconut palm (*Cocos mucifera*), oil palm (*Elaeis guineensis*), date palm (*Phoenix* spp.)), pineapple (*Ananas comosus*), Citrus trees (*Citrus* spp.), *Eucalyptus* sp., *Pinus* spp., cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentals*), Macadamia (*Macadamia integrifolia*), almond (*Prunus amygdalus*), sugar beets (*Beta vulgaris*), sugarcane (*Saccharum* spp.), oats, barley, vegetables, ornamentals, lawn grasses (poaceae family) and conifers. Each possibility is a separate embodiment.

In some embodiments, the desired crop plants are generated using gene-editing tools.

In some embodiments, methods for gene-editing includes, but are not limited to, using engineered nucleases such as meganucleases, zinc finger nucleases (ZFNs), transcription activator-like effector-based nucleases (TALEN), and clustered regularly interspaced short palindromic repeats (CRISPR), or any combination thereof. Each option is an embodiment by itself.

According to some aspects, herein provided is a non-naturally occurring crop plant or crop plant cell comprising a gene-edited regulatory element.

In some embodiments, the gene-editing of the regulatory element of the crop plant is based on the one or more identified genetic changes in the altered regulatory element of the selected model plant associated with the desired change in the expression level of the trait-related gene.

In some embodiments, the gene-edited plant or plant cell includes an increased expression of a native enzyme that increases a natural resistance of the plant to the herbicide.

In some embodiments, the gene-edited plant or plant cell includes an increased expression of an enzyme selected from the group consisting of Protoporphyrinogen Oxidase 1 (PPO1), or Protoporphyrinogen Oxidase 2 (PPO2), or p-hydroxyphenylpyruvate dioxygenase (HPPD), or 5-enolpyruvylshikimate 3-phosphate synthase (EPSPS), or Glutamine synthase, or acetolactate synthase (ALS enzyme), or 7,8-dihydropteroate synthase, or acetyl-CoA carboxylase (ACCase).

According to some aspects, herein provided is a construct that comprises a genetically modified promoter of a trait-related gene of a plant coupled to and functionally associated with an Herbicide Tolerance (HT) gene.

In some embodiments, the genetically modified promoter is derived from an endogenous promoter of a trait-related gene of a plant.

In some embodiments, the genetically modified promoter is derived from an endogenous promoter of a crop plant.

In some embodiments, the Herbicide Tolerance (HT) gene is exogenous of a crop plant.

According to some aspects, herein disclosed is a method for in-planta high throughput optimization of the function/activity of a trait-related gene.

According to some embodiments, the method comprising the steps of obtaining a nucleic acid encoding a coding sequence of a trait-related gene.

According to some embodiments, the method comprises the steps of introducing one or more genetic changes in each of a plurality of copies of the coding sequence of the native trait-related gene, thereby obtaining a genetic library comprising a large collection of altered copies of the trait-related gene coding sequence.

According to some embodiments, the method comprises the steps of introducing the genetic library into model plants, utilizing high throughput transformation, such that on average each model plant receives a single altered trait-related gene.

According to some embodiments, the method comprises the steps of screening the transformed model plants, wherein the screening comprises selecting a model plant having a desired change in function/activity of the trait-related gene.

According to some embodiments, the method comprising the steps of identifying one or more genetic changes in the altered trait-related gene coding sequence in the selected model plant.

According to some embodiments, the method comprising the steps of modifying a trait gene of a crop plant, based on the one or more identified genetic changes in the altered trait-related gene of the selected model plant.

In some embodiments, the desired change in the trait-related gene function/activity includes an optimized enzymatic activity.

In some embodiments, the desired change is an increased enzymatic activity.

According to some exemplified embodiments, the soybean (*Glycine max*) ppo1 promoter is cloned with the *Arabidopsis* (*A. thaliana*) PPOX1 gene.

In some embodiments, optimizing the expression levels of the plant's Protoporphyrinogen Oxidase (PPO1) native gene can result in improved herbicide tolerance (HT).

In some embodiments, the activity of the Protoporphyrinogen Oxidase 1 (PPOX1) overcomes the herbicide's active ingredient concentration in the plant, while similar concentration causes WT *Arabidopsis* plants to severely suffer or die.

In some embodiments, enhanced expression of Protoporphyrinogen Oxidase 1 (PPO1) is desired to lead to improved natural resistance to a PPO inhibitor type herbicide such as Flumioxazin.

According to some embodiments, the promoter may have the sequence set forth in Seq ID NO: 2; however other native promoters (of a same or different trait related gene) may also be envisaged and are as such within the scope of the disclosure. In some embodiments, cloning of the native soybean (*Glycine max*) ppo1 promoter (pGmppo1) (SEQ ID NO: 2) is performed to couple it to the *Arabidopsis* (*A. thaliana*) PPOX1 gene (AtPPOX1) (SEQ ID NO: 1), creating pGmppo1-AtPPOX1.

In some embodiments, the soybean's native ppo1 promoter (pGmppo1) is amplified from the soy gDNA and is cloned upstream to the native AtPPOX1 coding sequence.

In some embodiments, the native AtPPOX1 coding sequence is cloned with specific sequence marker (barcode) distinguishing it from the native copy of the gene.

In some embodiments, stable T1 or T2 pGmppo1-AtPPOX1 transgenic plants are used for_calibration of a PPO inhibitor chemical pre-determined cut-off concentration.

In some embodiments, PPO inhibitor chemical pre-determined cut-off concentration are used for screening and selection of variant plants library.

In some embodiments, the pGmppo1-AtPPOX1 containing binary vector that is commonly used for libraries construction is introduced to *Agrobacterium*.

In some embodiments, the *Agrobacterium* harboring the pGmppo1-AtPPOX1 gene are then used to transform *Arabidopsis* plants to produce seeds having stable T1 or T2 generation events.

In some embodiments, the transformed *Arabidopsis* seeds are germinated and treated with a selection herbicide to detect transformed plants.

In some embodiments, T1 or T2 *Arabidopsis* seeds are germinated and treated with a selection herbicide.

In some embodiments, calibration of the selection cut-off value is used for screening of transformed model plants for increased expression and/or activity of the AtPPOX1 enzyme and related enhancement of the herbicide tolerance (HT) trait.

In some embodiments, stable T1 or T2 *Arabidopsis* plants transformed with the pGmppo1-AtPPOX1 gene are treated with the PPO inhibitor type herbicide Flumioxazin or Carfentrazone Ethyl using a concentration gradient to calibrate the cut-off concentration.

In some embodiments, stable T1 or T2 events exhibiting the best tolerance towards the highest concentration of the PPO inhibitor type herbicide Flumioxazin or Carfentrazone Ethyl are selected based on at least one selection criteria.

In some embodiments, the pre-determined cut-off concentration is determined for use in selecting promoter variant transgenic plant libraries.

In some embodiments, the cut-off concentration is determined based on those stable T1 or T2 *Arabidopsis* plants transformed with the pGmppo1-AtPPOX1 gene and exhibiting the best tolerance towards the highest concentration of the PPO inhibitor type herbicide Flumioxazin or Carfentrazone Ethyl.

According to some embodiments, Algorithm analysis of the native soybean ppo promoter (pGmppo1) is utilized for the detection of putative hot-spots.

In some embodiments, a unique algorithm is utilized, for analyzing non-coding regulatory elements and predicting putative "hot-spots" for DNA binding proteins that take part in the process of transcription; in some embodiments, these include transcription factors and other transcription-related proteins that interact with the DNA in a sequence-specific manner.

In some embodiments, the algorithm utilizes available information on plant regulatory elements sequences derived from, but not limited to, public databases such as PlantCARE (Plant cis-Acting Regulatory Elements), PLACE (Plant cis-Acting Regulatory DNA Elements) and RegSite (Plant-oriented collections of transcription regulatory elements).

In some embodiments, the algorithm is applied for analysis of the native soybean ppo1 gene and predictions of hot-spots that may promote the desired change of enhanced transcription activity from the pGmppo1.

In some embodiments, the algorithm receives SEQ ID NO: 1 as an input sequence (the sequence of pGmppo1) and the typical architecture of the pGmppo1 promoter is analyzed to recognize specific regulatory elements therein; in some embodiments, this includes analysis of the proximal promoter (including core promoter) and the distal promoter.

In some embodiments, the promotor regions are identified by analyzing the several hundred nucleotides around the TSS, considered as the core/proximal promoter, for example for identifying elements regulating transcription start site (TSS) selection, and by analyzing the following thousands and more nucleotides further upstream of the TSS, considered as the distal promoter, for example for the existence of regulatory cis-elements that can function as transcription enhancers and may perform an accessory role in increasing the transcriptional activity In some embodiments, the algorithm identifies hot-spots of putative regulatory elements in pGmppo1, process and integrates data, and then predict sites on the promoter sequence suitable for genetic manipulation/editing thereby predicting potentially new regulatory elements having new attributes in respect to the gene's expression pattern.

In some embodiments, in case of the AtPPOX1, or GmPPO1 gene products, the desired change is increased expression and activity of the enzyme; In some embodiments, this can be achieved, for example, by introducing into hot-spot genetic changes that enforce the binding activity of transcription activators or prevent the binding activity of suppressors.

In some embodiments, targeting the hot-spots on the pGmppo1 promoter sequence may achieve the desired increase in the gene's transcription activity at specific developmental growth phase of the plant.

In some embodiments, targeting the hot-spots on the pGmppo1 promoter sequence may achieve the desired increase in the gene's transcription activity in specific tissues in which expression of the gene may be increased.

In some embodiments, targeting the hot-spots on the pGmppo1 promoter sequence may achieve the desired increase in the gene's transcription activity by enhancing the number of transcription events within the plant cells.

According to some embodiments, an in-planta genetic library of large collection of altered soybean ppo1 promoter (pGmppo1) elements is generated for high-throughput evaluation of enhanced Herbicide Tolerance (HT) in *Arabidopsis*.

In some embodiments, several genetic libraries comprising large collections of altered regulatory elements are generated by introducing genetic changes into the pGmppo1.

In some embodiments, the genetic alterations to pGmppo1 may be directed to specific regions (e.g. hot-spots). In some embodiments, the alterations may be introduced into random regions of the regulatory element.

In some embodiments, alterations in the pGmppo1 regulatory elements may be introduced utilizing site-directed mutagenesis, chemically or biologically induced random mutagenesis, recombination, shuffling, error-prone PCR, restrictions-ligations, solid-phase synthesis, synthesized synthetic libraries, or any combination thereof. Each possibility is a separate embodiment.

In some embodiments, pGmppo1 genetic variant libraries are validated, the quality of the libraries is tested by random sequencing of the library preceding a statistical analysis of nucleotide distribution at the mutation sites.

In some embodiments, the obtained pGmppo1-AtPPOX1 or pGmppo1-GmPPO1 nucleic acid is introduced to *Agrobacterium* and transformed into *Arabidopsis* plants utilizing a high-throughput transformation method creating in-planta promoter libraries.

In some embodiments, each in-planta promoter library contains a collection of approximately $10^3$-$10^6$ transgenic pGmppo1-AtPPOX1 or pGmppo1-GmPPO1 plants.

In some embodiments, each transgenic pGmppo1-AtPPOX1 or pGmppo1-GmPPO1 plant of the in-planta promoter libraries carries on average each a single genetically altered regulatory element.

In some embodiments, each single genetically altered regulatory element has at least one or more genetic changes in the pGmppo1.

According to some embodiments, *Arabidopsis* plants are screened and selected for enhanced Herbicide Tolerance (HT).

In some embodiments, the evaluation of improved Herbicide Tolerance (HT) trait in model plants is performed by a high-throughput screening process using PPO inhibitor.

In some embodiments, transgenic pGmppo1-AtPPOX1, or pGmppo1-GmPPO1 seeds are germinated, and the plants are treated with Flumioxazin, the active ingredient in Strike, or Carfentrazone Ethyl, the active ingredient in Aurora, according to the pre-determined cut-off concentration.

In some embodiments, plants showing high tolerance towards cut-off concentrations of Flumioxazin or Carfentrazone Ethyl, are selected for their possible resistance to the herbicide.

In some embodiments, the level of tolerance is determined based on the same at least one selection criteria used in the preliminary experiments with the native promoter to establish the cut-off concentration.

In some embodiments, the specific genetic variation in the pGmppo1 promoter of the selected pGmppo1-AtPPOX1 or pGmppo1-GmPPO1 harboring plants is identified by DNA sequencing.

In some embodiments, the best putative promoters are used to retransform *Arabidopsis* plants and are tested again for resistance against Flumioxazin or Carfentrazone Ethyl.

According to some embodiments, an enhanced Herbicide Tolerance (HT) gene-edited soybean crop plant is generated.

In some embodiments, the genetic change identified in model plants expressing the desired level of resiliency are introduced into the desired *Glycine max* crop plant.

In some embodiments, the identified genetic changes are introduced into the desired *Glycine max* crop plant utilizing gene-editing methods in order to generate genetically modified, non-transgenic soybeans plants possessing enhanced Herbicide Tolerance HT.

According to some embodiments, the soybean (*Glycine max*) ppo1 promoter is cloned with GFP for evaluation of enhanced expression fluorescence.

In some embodiments, the expression of the non-native trait-related sequence of a reporter protein such as a fluorescent protein leads to the manifestation of a desirable/beneficial phenotypic trait of having a detectable fluorescent signal.

In some embodiments, a native promoter of soybean (pGmX) is cloned upstream to a sequence encoding a coding sequence of GFP, producing a non-native (pGmX-GFP).

In some embodiments, the evaluation of improved fluorescence in model plants is performed by a high-throughput screening process using detection of fluorescence levels according to a pre-determined green fluorescence cut-off.

In some embodiments, plants showing higher fluorescence levels than the green fluorescence cut-off are selected for their possible desired change in expression associated with altered promoter of soybean (pGmX).

In some embodiments, pGmX-GFP is stably expressed in model plants. In some embodiments, pGmX-GFP is transiently expressed in soybean plants.

In some embodiments, the level of fluorescence is determined based on the same or different, at least one selection criteria used in the preliminary experiments with the native pGmX-GFP in order to establish the green fluorescence cut-off concentration.

According to some embodiments, a native regulatory element is cloned with the Herbicide Tolerance (HT) related Protoporphyrinogen Oxidase (PPOX1) gene of *Arabidopsis* (AtPPOX1) for evaluation of a desired change in expression.

According to some embodiments, a native regulatory element is cloned with the Herbicide Tolerance (HT) related Protoporphyrinogen Oxidase (PPO1) gene of soybean (GmPPO1) for evaluation of a desired change in expression.

In some embodiments, the expression of the coding sequence of the Herbicide Tolerance (HT) related Protoporphyrinogen Oxidase (PPOX1) gene of *Arabidopsis* (AtPPOX1) leads to the manifestation of a desirable/beneficial phenotypic trait of having enhanced resistance to the PPO-inhibitor, for example, Oxadiazon, Flumioxazin, or Carfentrazone Ethyl, thereby allowing high-throughput screening of model plants manifesting a desired change in expression from an altered regulatory element of any native gene of any desired crop plant that is functionally coupled to the trait.

In some embodiments, the expression of the coding sequence of the Herbicide Tolerance (HT) related Protoporphyrinogen Oxidase (PPO1) gene of soybean (*Glycine max*) (GmPPO1) leads to the manifestation of a desirable/beneficial phenotypic trait of having enhanced resistance to the PPO-inhibitor, for example, Oxadiazon, Flumioxazin, or Carfentrazone Ethyl, thereby allowing high-throughput screening of model plants manifesting a desired change in expression from an altered regulatory element of any native gene of any desired crop plant that is functionally coupled to the trait.

In some embodiments, the coding sequence of Protoporphyrinogen Oxidase (PPOX1) *Arabidopsis* (AtPPOX1) is cloned downstream to the promoter of a native gene for evaluation of the desired change in expression that is associated with improved activity of Protoporphyrinogen Oxidase (PPOX1).

In some embodiments, the coding sequence of Protoporphyrinogen Oxidase (PPO1) of soybean (Glycin max) (GmPPO1) is cloned downstream to the promoter of a native gene for evaluation of the desired change in expression that is associated with improved enzymatic activity of Protoporphyrinogen Oxidase (PPO1).

In some embodiments, the expression of a reporter gene (e.g. an HT gene) may be utilized for high-throughput screening for identification of optimized regulatory elements (the regulatory element preferably originating from a crop-plant, e.g. the promoter of a salt-tolerance-related gene). The screen may thus be conducted in model plants by monitoring the change in expression of the reporter gene and/or phenotype of the model plant (e.g. increased herbicide tolerance, fluorescence level etc.), as a result of it being functionally coupled to an altered version of the regulatory element.

In some embodiments, the expression of a trait, such as but not limited to HT, is utilized for high-throughput screening of model plants manifesting a desired change in expression of the trait-related gene/reporter gene that is functionally coupled to the altered regulatory element which may be originated from any native gene of any desired crop plant.

In some embodiments, the expression of a trait is utilized for high-throughput screening of model plants harboring a library of altered regulatory elements by applying selection conditions corresponding to that trait and is based on meeting the cut-off that was pre-determined with respect to the corresponding selection criteria.

In some embodiments, a high-throughput screening of model plants is performed utilizing a trait for resistance or enhanced yield, including but not limited to resistance to herbicides, insects, and disease or other biotic stress, tolerance to heat, drought, or other abiotic stress, reduced time to crop maturity, enhanced yield, improved fertilizer uptake, improved industrial processing, such as for the conversion of starch or biomass to fermentable sugars, and improved agronomic quality, such as high oil content and high protein content. Each possibility is a separate embodiment. Each possibility is a different embodiment.

In some embodiments, evaluation and selection of improved Herbicide Tolerance (HT) trait in model plants comprises high-throughput in-planta functional screening assay using PPO inhibitor herbicide spraying in purpose to easily identify low-frequency mutants.

Figure 3A:
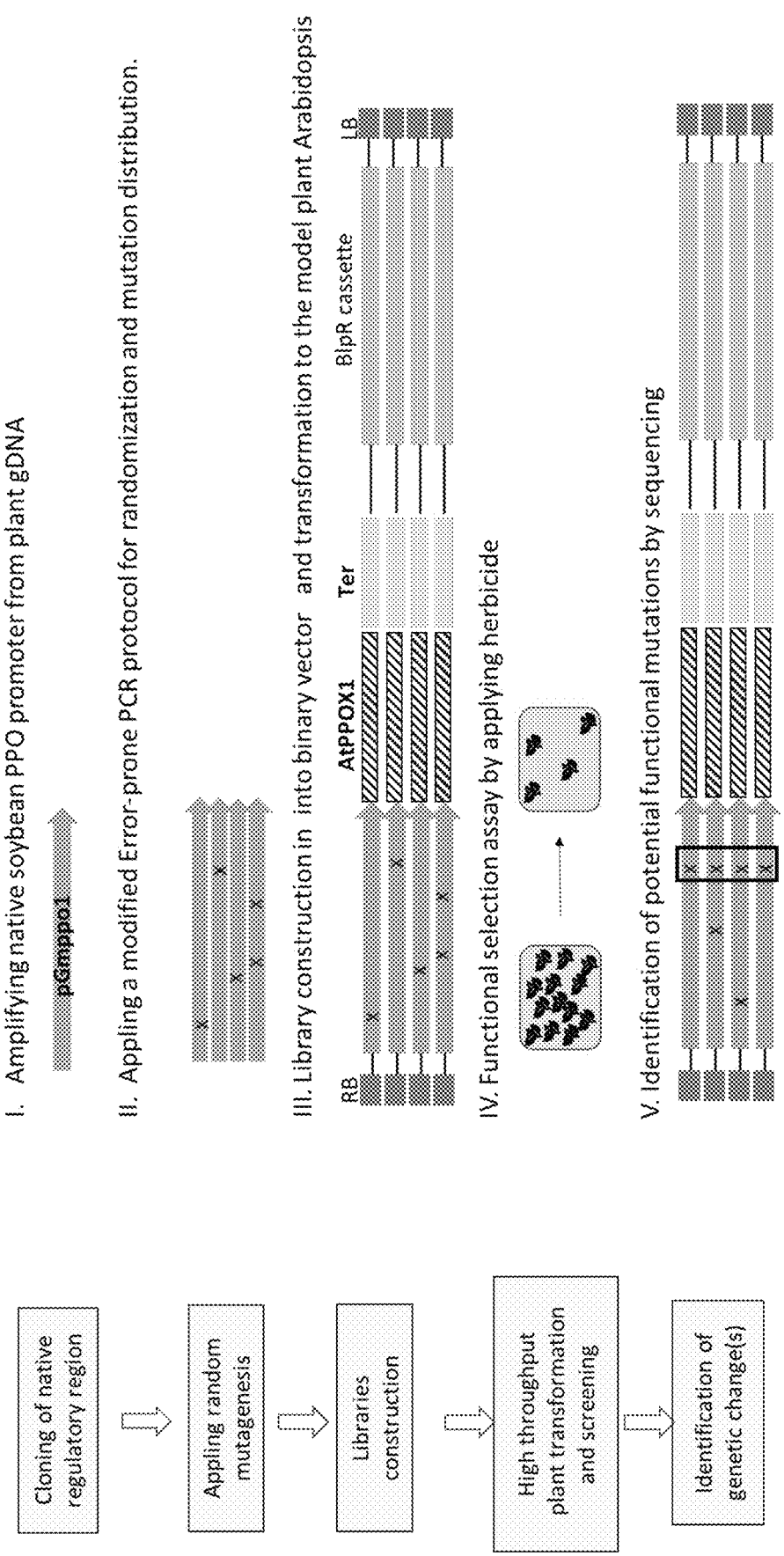
FIG. 3A illustrates the steps I-V of the process of cloning and randomly mutating the native promoter regulatory element of soybean PPO gene (pGmPPO1).
Figure 3B:
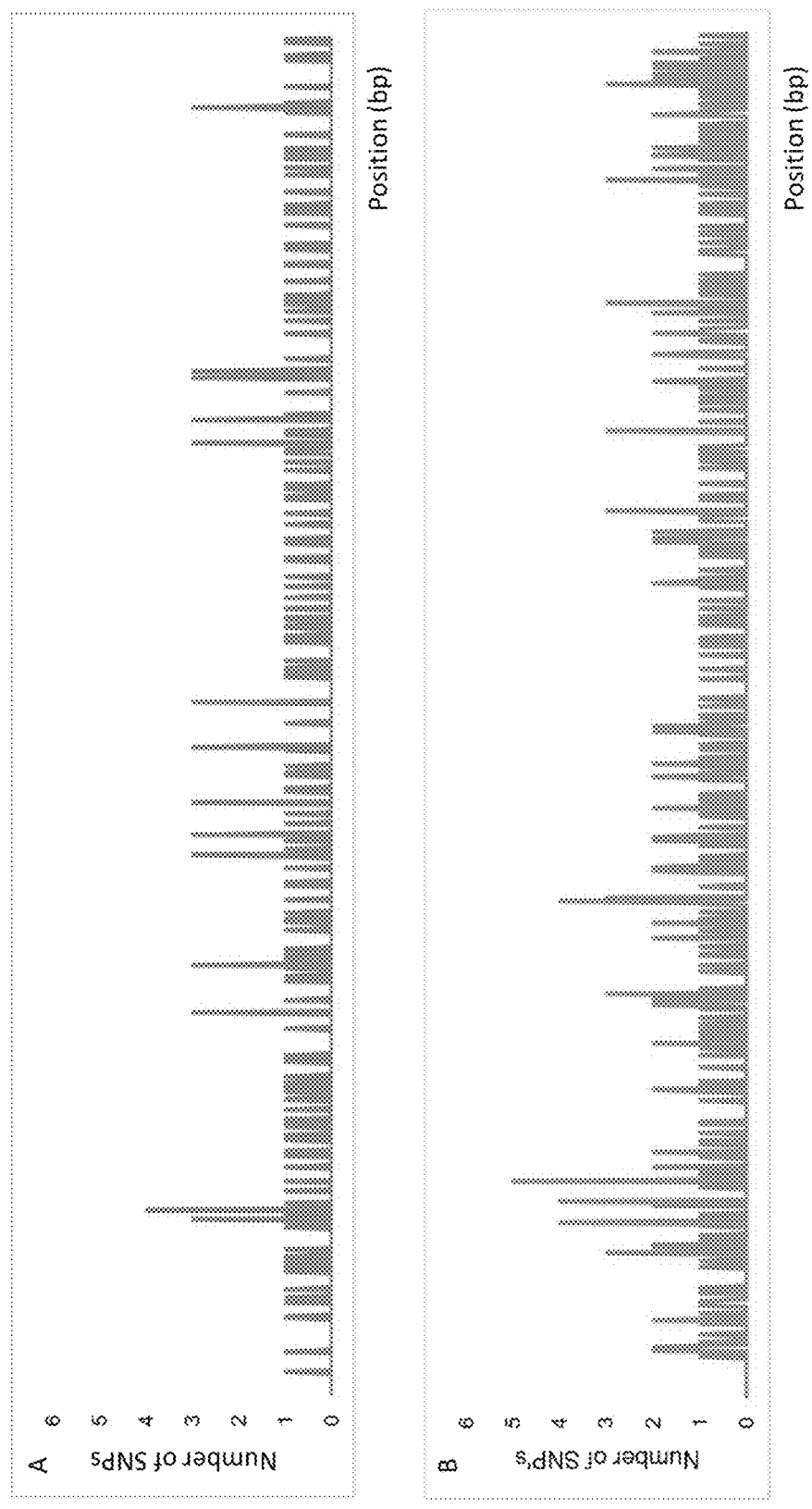
FIG. 3B is a histogram of distribution of the number of mutations per position along the pGmppo1 promoter forming the mutated libraries, as it was amplified from random colonies and sequenced following error prone PCR mutagenesis. chimeric pGmppo1-AtPPOX1 (top panel) or pGmppo1-GmPPO1 (bottom panel).
Figure 3C:
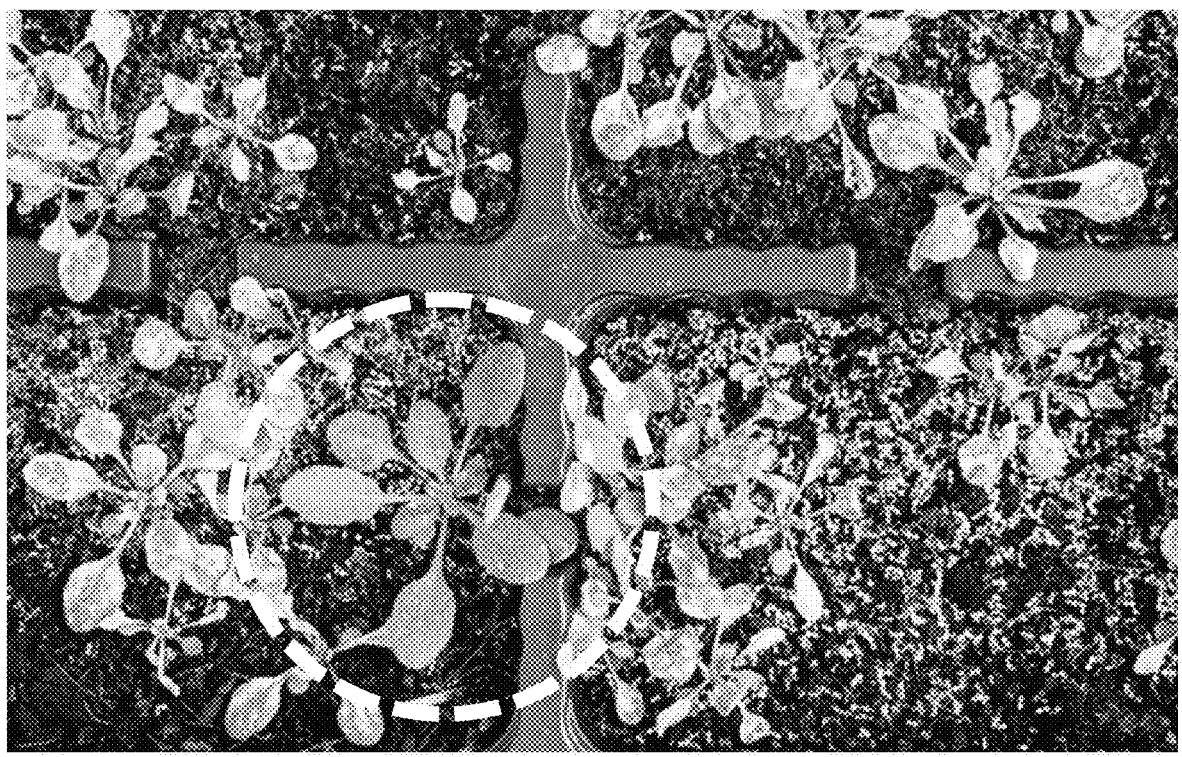
FIG. 3C exhibits a representative picture from in-planta functional screening assay for PPO herbicide tolerant plants. T1 transformed plants were initially selected on glufosinate ammonium to identify transgenic plants containing genetic alterations in the PPO1 promoter (pGmppo1). Functional selection was performed by spraying plants with $5 \times 10^{-3}\%$ Oxadiazon (Star). White circle depicts transgenic PPO tolerant plant, containing a desired genetic change in the PPO1 promoter (pGmppo1) surrounded by multiple susceptible plants, containing other non-tolerant enhancing PPO promoters.

Reference is now made to FIG. 3C In some embodiment, determining enhanced tolerance comprises evaluation of the damage to leaves at least at pre-determined cut-off concentration.

Figure 3D:
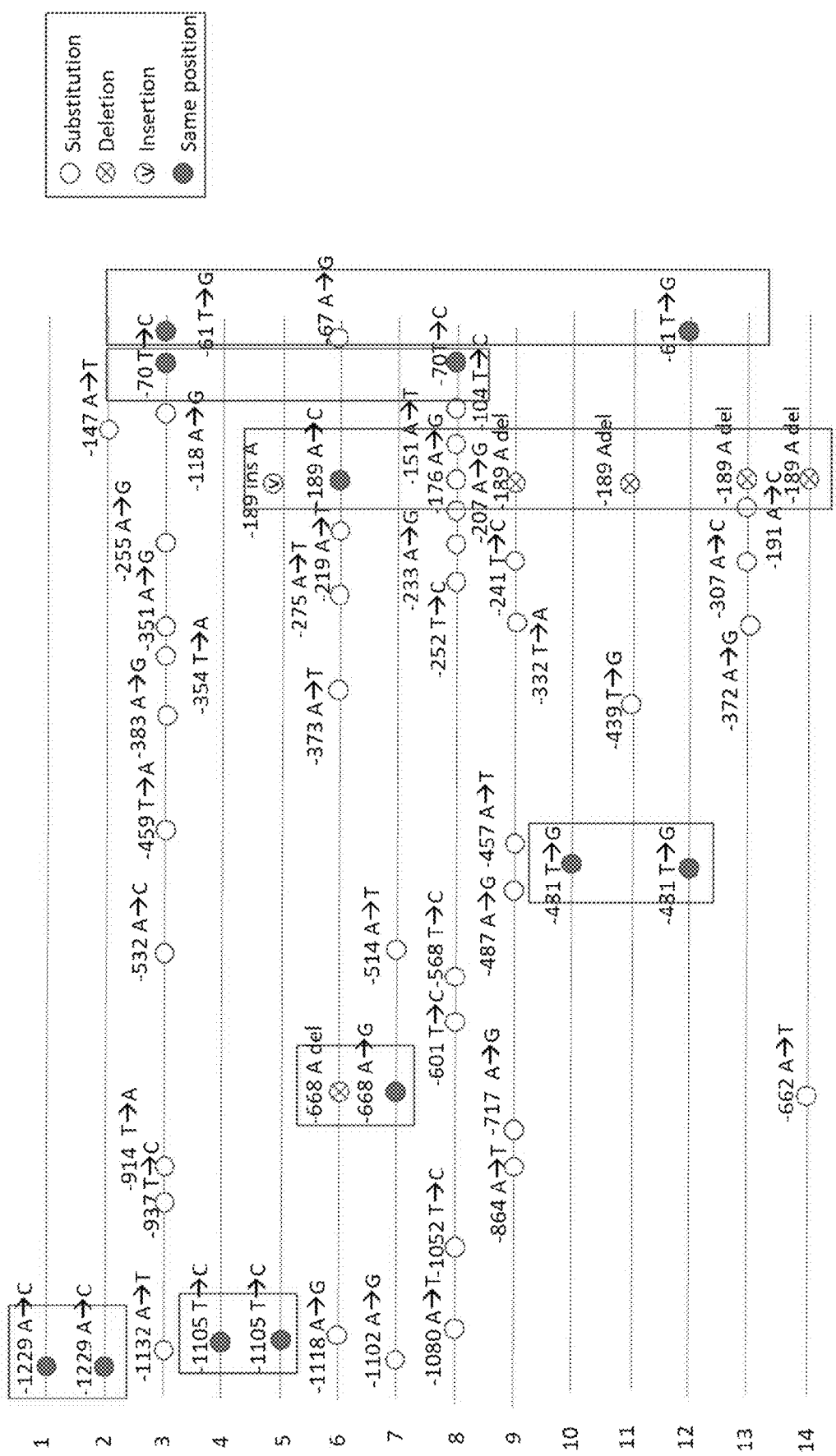

In some embodiment, mutated sequences of pGmppo1 generated by random mutagenesis, screened in planta, and identified by sequencing of the transgenes of selected resistant events are denoted by any one of SEQ ID NOs: 4-63. In some embodiments, the mutations and their positions are summarized in Table 1—describing identified hot spots in the soybean ppo1 promoter (pGmppo1) of different resistant event and set forth in any one of SEQ ID NOs: 4-13), and in Table 2—describing the remaining mutations identified in soybean PPO1 promoter (pGmppo1) of different resistant event and set forth in any one of SEQ ID NOs: 14-63). Each possibility is a separate embodiment. Reference is now made to FIG. 3D

TABLE 1 seven hot spots identified in soybean ppo1 promoter (pGmppo1)

| Hot spot | (event #) | Position/mutation | SEQ ID NO: |
|---|---|---|---|
| 1 | event 1; event 2 | −1229 A > C | SEQ ID NO: 4 |
| 2 | event 4; event 5 | −1105 T > C | SEQ ID NO: 5 |
| 3 | event 6 | −668 A del | SEQ ID NO: 6 |
|   | event 7 | −668 A > G | SEQ ID NO: 7 |
| 4 | event 10; event 12 | −481 T > G | SEQ ID NO: 8 |
| 5 | events 5 | −189 ins A | SEQ ID NO: 9 |
|   | event 6 | −189 A > C | SEQ ID NO: 10 |
|   | event 9; event 11; event 13; event 14 | −189 A del | SEQ ID NO: 11 |
| 6 | event 3; event 8 | −70 T > C | SEQ ID NO: 12 |
| 7 | event 3; event 12 | −61 T > G | SEQ ID NO: 13 |

TABLE 2 mutations identified in soybean PPO1 promoter (pGmppo1)

| Event# | Position/mutation | SEQ ID NO: |
|---|---|---|
| 2 | −147 A > T | SEQ ID NO: 14 |
| 2 | All mutations: −1229 A > C; −147 A > T | SEQ ID NO: 15 |
| 3 | −1132 A > T | SEQ ID NO: 16 |
| 3 | −937 T > C | SEQ ID NO: 17 |
| 3 | −914 T > A | SEQ ID NO: 18 |
| 3 | −532 A > C | SEQ ID NO: 19 |
| 3 | −459 T > A | SEQ ID NO: 20 |
| 3 | −383 A > G | SEQ ID NO: 21 |
| 3 | −354 T > A | SEQ ID NO: 22 |
| 3 | −351 A > G | SEQ ID NO: 23 |
| 3 | −255 A > G | SEQ ID NO: 24 |
| 3 | −118 A > G | SEQ ID NO: 25 |
| 3 | All mutations: −1132 A > T; −937 T > C; −914 T > A; −532 A > C; −459 T > A; −383 A > G; −354 T > A; −351 A > G; −255 A > G; −118 A > G; −70 T > C; −61 T > G | SEQ ID NO: 26 |
| 5 | All mutations: −1105 T > C; −189 ins A | SEQ ID NO: 27 |
| 6 | −1118 A > G | SEQ ID NO: 28 |
| 6 | −373 A > T | SEQ ID NO: 29 |
| 6 | −275 A > T | SEQ ID NO: 30 |
| 6 | −219 A > T | SEQ ID NO: 31 |
| 6 | −67 A > G | SEQ ID NO: 32 |
| 6 | All mutations: −1118 A > G; −668 A del; −373 A > T; −275 A > T; −219 A > T −189 A > C; −67 A > G | SEQ ID NO: 33 |
| 7 | −1102 A > G | SEQ ID NO: 34 |
| 7 | −514 A > T | SEQ ID NO: 35 |
| 7 | All mutations: −1102 A > G; −668 A > G; −514 A > T | SEQ ID NO: 36 |
| 8 | −1080 A > T | SEQ ID NO: 37 |
| 8 | −1052 T > C | SEQ ID NO: 38 |
| 8 | −601 T > C | SEQ ID NO: 39 |
| 8 | −568 T > C | SEQ ID NO: 40 |
| 8 | −252 T > C | SEQ ID NO: 41 |
| 8 | −233 A > G | SEQ ID NO: 42 |
| 8 | −207 A > G | SEQ ID NO: 43 |
| 8 | −176 A > G | SEQ ID NO: 44 |
| 8 | −151 A > T | SEQ ID NO: 45 |
| 8 | −104 T > C | SEQ ID NO: 46 |
| 8 | All mutations: −601 T > C; −568 T > C; −252 T > C; −233 A > G; −207 A > G −176 A > G; −151 A > T; −104 T > C; −70 T > C | SEQ ID NO: 47 |
| 9 | −864 A > T | SEQ ID NO: 48 |
| 9 | −717 A > G | SEQ ID NO: 49 |
| 9 | −487 A > G | SEQ ID NO: 50 |
| 9 | −457 A > T | SEQ ID NO: 51 |
| 9 | −332 T > A | SEQ ID NO: 52 |
| 9 | −241 T > C | SEQ ID NO: 53 |
| 9 | All mutations: −864 A > T; −717 A > G; −487 A > G; −457 A > T; −332 T > A −241 T > C; −189 A del | SEQ ID NO: 54 |
| 11 | −439 T > G | SEQ ID NO: 55 |
| 11 | All mutations: −439 T > G; −189 A del | SEQ ID NO: 56 |
| 12 | All mutations: −481 T > G; −61 T > G | SEQ ID NO: 57 |
| 13 | −372 A > G | SEQ ID NO: 58 |
| 13 | −307 A > C | SEQ ID NO: 59 |
| 13 | −191 A > C | SEQ ID NO: 60 |
| 13 | All mutations: −372 A > G; −307 A > C; −191 A > C; −189 A del | SEQ ID NO: 61 |
| 14 | −662 A > T | SEQ ID NO: 62 |
| 14 | All mutations: −662 A > T; −189 A del | SEQ ID NO: 63 |

In some embodiments, the soybean ppo1 promoter (pGmppo1) comprises 7 'hot' positions that when mutated confer enhanced/improved herbicide tolerance (HT) trait.

In some embodiments, the disclosed ppo1 promoter (ppo1) of the invention comprises a genetic change in one or more of any of the 7 'hot' positions that when mutated confer enhanced/improved herbicide tolerance (HT) trait to a plant.

In some embodiments, the disclosed ppo1 promoter (ppo1) of the invention comprises one or more mutations in one or more positions corresponding to any one or more of the mutated positions in the soybean ppo1 promoter set forth in SEQ ID NO: 4-63. (i.e., as detailed in table 1 and table 2)

In some embodiments, the disclosed ppo1 promoter (ppo1) of the invention comprises one or more mutations in one or more positions corresponding to any one or more of the mutated positions in the soybean ppo1 promoter set forth in SEQ ID NO: 4-13. (i.e., as detailed in table 1)

In some embodiments, the disclosed ppo1 promoter (ppo1) of the invention comprises one or more mutations in one or more positions corresponding to any one or more of the mutated positions in the soybean ppo1 promoter set forth in SEQ ID NO: 14-63. (i.e., as detailed in table 2)

In some embodiments, the disclosed ppo1 promoter ppo1) of the invention comprises the sequence set forth in any one of SEQ ID NOs: 4-63, or any combination thereof. In some embodiments, the disclosed ppo1 promoter (ppo1) of the invention comprises the sequence set forth in any one of SEQ ID NOs: 4-13, or any combination thereof. In some embodiments, the disclosed ppo1 promoter (ppo1) of the invention comprises the sequence set forth in any one of SEQ ID NOs: 14-63, or any combination thereof.

In some embodiments, the seven 'hot' positions in the native soybean ppo1 promoter that when mutated confer enhanced/improved herbicide tolerance (HT) trait include the following positions with respect to SEQ ID NO: 2: [−1229A], [−1105T], [−668A], [−481T], [−189A], [−70T] and [−61T], wherein (-) denotes an upstream position relative to the Transcription Start Site (TSS). Reference is now made to Table 1 and FIG. 3D (hot positions marked within rectangles).

In some embodiments, the identified hot spots in pGmppo1 comprise the mutations as denoted by any one of SEQ ID NO. 4-13.

According to some aspects, there is provided a gene edited crop plant or crop plant cell comprising a ppo1 promoter genetically modified to include one or more mutations in one or more positions corresponding to any one or more of positions: −1229 A, −1105 T, −668 A, −481 T, −189 A, −70 T, and −61 T of the soybean promoter as set forth in SEQ ID NO: 2.

As used herein, the term "corresponding to" refers to positions in ppo1 promoters of any other crop plant with respect to homologous positions in the soybean ppo1 promoter (pGmppo1), as determined by aligning the sequences together by a sequence alignment tool.

In some embodiments, the gene edited crop plant or crop plant cell, wherein the one or more mutations in the genetically modified ppo1 promoter include substitution, addition and/or deletion.

In some embodiments, the gene edited crop plant or crop plant cell, wherein the one or more mutations in the genetically modified ppo1 promoter comprising one or more of: −1229 A>C, −1105 T>C, −668 A del, −668 A>G, −481 T>G, −189 ins A, −189 A>C, −189 A del, −70 T>C, and −61 T>G; and wherein the positions correspond to the positions of the soybean promoter as set forth in SEQ ID NO: 2.

In some embodiments, the gene edited crop plant or crop plant cell, wherein the one or more mutations in the genetically modified ppo1 promoter comprise at least 2, at least 3, at least 4, at least 5, at least 6, at least 7, at least 8, at least 9, at least 10, or more, mutated positions. Each possibility is separate embodiment.

In some embodiments, the gene edited crop plant or crop plant cell, wherein the ppo1 promoter comprises at least 90% sequence identity to SEQ ID NO: 2.

In some embodiments, the ppo1 promoter comprises at least 80%, at least 85%, at least 90%, at least 95%, at least 96%, at least 97%, at least 98%, or at least 99% sequence identity to SEQ ID NO: 2. Each possibility is a separate embodiment.

In some embodiments, the gene edited crop plant or crop plant cell, wherein the ppo1 promoter comprises the sequence set forth in any one of SEQ ID Nos: 4-13.

In some embodiments, the gene edited crop plant or crop plant cell, wherein the ppo1 promoter comprises the sequence set forth in any one of SEQ ID Nos: 4-13, or any combination thereof.

In some embodiments, the gene edited crop plant or crop plant cell, wherein the ppo1 promoter comprises the sequence set forth in any one of SEQ ID Nos: 14-63.

In some embodiments, the gene edited crop plant or crop plant cell, wherein the ppo1 promoter comprises the sequence set forth in any one of SEQ ID Nos: 14-63, or any combination thereof.

In some embodiments, there is provided a gene edited crop plant or crop plant cell, wherein the crop plant is soybean.

According to some aspects there is provided a nucleic acid construct comprising a genetically modified promoter of a trait-related gene of a plant coupled to and functionally associated with an Herbicide Tolerance (HT) gene.

According to some aspects, there is provided a nucleic acid construct comprising a ppo1 promoter genetically modified to include one or more mutations in one or more positions corresponding to any one or more of positions: −1229 A, −1105 T, −668 A, −481 T, −189 A, −70 T, and −61 T of the soybean promoter as set forth in SEQ ID NO: 2.

In some embodiments, the provided nucleic acid construct, wherein the genetically modified ppo1 promoter is coupled to and functionally associated with an Herbicide Tolerance (HT) gene.

In some embodiments, the provided nucleic acid construct, wherein the one or more mutations in the genetically modified ppo1 promoter comprising one or more of: −1229 A>C, −1105 T>C, −668 A del, −668 A>G, −481 T>G, −189 ins A, −189 A>C, −189 A del, −70 T>C, and −61 T>G.

In some embodiments, the provided nucleic acid construct, wherein the one or more mutations in the genetically modified ppo1 promoter include substitution, addition and/ or deletion.

In some embodiments, the provided nucleic acid construct, wherein the one or more mutations in the genetically modified ppo1 promoter comprise at least 2, at least 3, at least 4, at least 5, at least 6, at least 7, at least 8, at least 9, at least 10, or more, mutated positions. Each possibility is separate embodiment.

In some embodiments, the provided nucleic acid construct, wherein the genetically modified ppo1 promoter comprising at least 90% sequence identity to SEQ ID NO: 2.

In some embodiments, the ppo1 promoter comprises at least 80%, at least 85%, at least 90%, at least 95%, at least 96%, at least 97%, at least 98%, or at least 99%, or at least 99.9% sequence identity to SEQ ID NO: 2. Each possibility is a separate embodiment.

In some embodiments, the provided nucleic acid construct, wherein the genetically modified ppo1 promoter comprises the sequence set forth in any one of SEQ ID Nos: 4-13, or any combination thereof.

In some embodiments, the provided nucleic acid construct, wherein the genetically modified ppo1 promoter comprises the sequence set forth in any one of SEQ ID Nos: 14-63, or any combination thereof.

In some embodiments, the reporter gene is cloned downstream to the promoter of a native trait-related gene for evaluation of the desired change in expression of the reporter gene that is associated with a genetic change introduced to the promoter of the native gene. Reference is made to FIG. 2B.

In some embodiments, the reporter gene is cloned as a fusion protein downstream to the coding sequence of a native trait-related gene for evaluation of the desired change in expression of the reporter that is associated with a genetic change introduced to the coding sequence of the native gene. Reference is made to FIG. 2C.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

The following examples exemplifies the use of the herein disclosed method for enhancing gene function/activity related to a plant improving trait, in-planta. It is however understood by one of ordinary skill in the art that Herbicide Tolerance (HT) serves as an example only, and that the platform may be used for optimizing the expression of any endogenous trait.

Example 1: Cloning of the Soybean (*Glycine max*) Ppo1 Promoter with the *Arabidopsis* (*A. thaliana*) PPOX1 Gene, for Transformation and Determination of Selection Cut-Off of Enhanced Natural Herbicide Tolerance (HT)

Optimizing expression levels of plant's Protoporphyrinogen Oxidase (PPOX1) native gene can result in improved herbicide tolerance (HT) when the activity of the enzyme overcomes the concentration of the herbicide's active ingredient in the plant. In accordance, enhanced expression of Protoporphyrinogen Oxidase (PPOX1) is desired to lead to improved natural resistance to a PPO inhibitor type herbicide such as Oxadiazon, Flumioxazin, or Carfentrazone Ethyl, the active ingredient in Strike and Aurora respectively.

Therefore, initially, the *Arabidopsis* (*A. thaliana*) PPOX1 Mrna sequence (SEQ ID NO: 1) (coding for AtPPOX1) was cloned into the backbone of the Ppa35H binary vector commonly used for libraries construction, downstream to the soybean (*Glycine max*) ppo1 promoter (pGmppo1) (SEQ ID NO: 2), creating a chimeric pGmppo1-AtPPOX1 (FIG. 1A). The Soybean's native ppo1 promoter (pGmppo1) was amplified from the soy Gdna by standard PCR methods and was cloned upstream to the native AtPPOX1 Mrna coding sequence with specific sequence marker distinguishing it from the native copy of the *Arabidopsis* promoter for later molecular distinguishing Qpcr work.

```
Arabidopsis (A. thaliana) PPOX1 Mrna (AtPPOX1) SEQ ID NO: 1:
GAAGAAGATTACCCAATCTGAAAAAAACCAAGAAGCTGACAAAATTCCGAATTCTCTGCGATTTCCATGG
AGTTATCTCTTCTCCGTCCGACGACTCAATCGCTTCTTCCGTCGTTTTCGAAGCCCAATCTCCGATTAAA
TGTTTATAAGCCTCTTAGACTCCGTTGTTCAGTGGCCGGTGGACCAACCGTCGGATCTTCAAAAATCGAA
GGCGGAGGAGGCACCACCATCACGACGGATTGTGTGATTGTCGGCGGAGGTATTAGTGGTCTTTGCATCG
CTCAGGCGCTTGCTACTAAGCATCCTGATGCTGCTCCGAATTTAATTGTGACCGAGGCTAAGGATCGTGT
TGGAGGCAACATTATCACTCGTGAAGAGAATGGTTTTCTCTGGGAAGAAGGTCCCAATAGTTTTCAACCG
TCTGATCCTATGCTCACTATGGTGGTAGATAGTGGTTTGAAGGATGATTTGGTGTTGGGAGATCCTACTG
CGCCAAGGTTTGTGTTGTGGAATGGGAAATTGAGGCCGGTTCCATCGAAGCTAACAGACTTACCGTTCTT
TGATTTGATGAGTATTGGTGGGAAGATTAGAGCTGGTTTTGGTGCACTTGGCATTCGACCGTCACCTCCA
GGTCGTGAAGAATCTGTGGAGGAGTTTGTACGGCGTAACCTCGGTGATGAGGTTTTTGAGCGCCTGATTG
AACCGTTTTGTTCAGGTGTTTATGCTGGTGATCCTTCAAAACTGAGCATGAAAGCAGCGTTTGGGAAGGT
TTGGAAACTAGAGCAAAATGGTGGAAGCATAATAGGTGGTACTTTTAAGGCAATTCAGGAGAGGAAAAAC
GCTCCCAAGGCAGAACGAGACCCGCGCCTGCCAAAACCACAGGGCCAAACAGTTGGTTCTTTCAGGAAGG
GACTTCGAATGTTGCCAGAAGCAATATCTGCAAGATTAGGTAGCAAAGTTAAGTTGTCTTGGAAGCTCTC
AGGTATCACTAAGCTGGAGAGCGGAGGATACAACTTAACATATGAGACTCCAGATGGTTTAGTTTCCGTG
CAGAGCAAAAGTGTTGTAATGACGGTGCCATCTCATGTTGCAAGTGGTCTCTTGCGCCCTCTTTCTGAAT
CTGCTGCAAATGCACTCTCAAAACTATATTACCCACCAGTTGCAGCAGTATCTATCTCGTACCCGAAAGA
AGCAATCCGAACAGAATGTTTGATAGATGGTGAACTAAAGGGTTTTGGGCAATTGCATCCACGCACGCAA
GGAGTTGAAACATTAGGAACTATCTACAGCTCCTCACTCTTTCCAAATCGCGCACCGCCCGGAAGAATTT
TGCTGTTGAACTACATTGGCGGGTCTACAAACACCGGAATTCTGTCCAAGTCTGAAGGTGAGTTAGTGGA
AGCAGTTGACAGAGATTTGAGGAAAATGCTAATTAAGCCTAATTCGACCGATCCACTTAAATTAGGAGTT
AGGGTATGGCCTCAAGCCATTCCTCAGTTTCTAGTTGGTCACTTTGATATCCTTGACACGGCTAAATCAT
CTCTAACGTCTTCGGGCTACGAAGGGCTATTTTTGGGTGGCAATTACGTCGCTGGTGTAGCCTTAGGCCG
GTGTGTAGAAGGCGCATATGAAACCGCGATTGAGGTCAACAACTTCATGTCACGGTACGCTTACAAGTAA
ATGTAAAACATTAAATCTCCCAGCTTGCGTGAGTTTTATTAAATATTTTGAGATATCAAACTTCAATTTC
ATTTTGATACATAGATTTGAGTTATAGTTATATTTAGGAGAAGGGTCTTTGGTT the native soybean (Glycine max) ppo1 promoter (pGmppo1) SEQ ID NO: 2
(-) denotes upstream position relative to the Transcription Start Site (TSS)
-1272  ATTAAGAAGC  TTACAAAGAG  ATTGGGAACT  AAAACTACTT  AAAAAAAAAG  GAATTAAAAT-1213
-1212  CAATTTCAAC  CAAATTATAA  GAGACTTAAG  ATACATTTTA  TTCTAGGAAA  CAATATTACT-1153
-1152  TCTGGACTTT  TAAACAAGAA  ACAAAAAATA  AATTAATTAA  GATCAATTGA  ATAGTTAATT-1093
-1092  TAATTATTTT  TAATCAATAA  TATTATAAAT  TTATATTTTA  TTCTAAAAAT  GTTTATCAAA-1033
-1032  CTAAGTAACA  TCTGGTTTTA  TATTTGTTCA  GAGAAAATGC  GTAGCTAACT  CTATGCATTA-973
-972   AACAAAAAAA  AGAAAATTTT  CTTTCAATTT  TTCGATTTTT  CCATTTGATT  TTATTGTTTG-913
-912   GGAATTATTT  TTCCTTAATT  CTTTCCATTC  TATCAATGAA  GAATCTATAA  GAATTCTCAA-853
-852   TTCCATATCA  TTTCATTTTT  AAAAATTTAA  TCGTAATGGA  AATAAGAAAG  ACTAATATTC-793
-792   CTTTGGAAAT  ATTACCCGAA  TGATATTTCT  TCTCTTATAG  GTAATAAGTA  TATTATTTGT-733
-732   AATTCAATAG  AACAAATTTC  TTATATTGTT  ATTAGTTCAA  TAAATATATT  TATTTACATA-673
-672   AAAAATAATA  AAAGGAGATC  TATCTTAAAT  TCTTGTATAT  GAAATTTGAT  TCTCGTGAAT-613
-612   GAAACAAAAC  ATAAAAAAAG  ATCATGAGTA  ACTTGATGAT  GCTATTGCCA  TTATTAATAG-553
-552   TTTAATAATT  ATTCCTTAAA  ATAAATAGTT  CAATAACTAT  ATCTACTTAC  AAAGAAAATA-493
-492   AAATGAGCGA  CTTATATTTT  TTATTAGCTT  TAATGATTAA  TCTTTATAAA  AAATTACTAA-433
-432   AAATATTTAA  TGATACGTCA  TTTTTCAATT  ATGTTTCTTT  CCTTTACTAA  ACTCGAATCA-373
-372   AATACAAAAA  TAAATTGTTT  GAGTGCCGAA  AGTCCGAAAC  TTATTATTTG  ACTTCAAAAT-313
-312   AAGTTATTGT  TTTTATCTTA  TAATAATCGT  CCTATAAAAA  AAATTATTCT  AAATATTAGC-253
-252   TTTTATTTGA  CTTCAAAATA  AGTTATTGCT  TTTATAATAA  TAATGATATG  ATAAAAAAAA-193
-192   AAAACTAATA  GATAAAAAAA  GTACTTAGAA  AACATTTTTT  CAAGAACGTT  AAAGGTAAAG-133
-132   TTTAGATGGA  GGCAATTGTG  TATTTTACTG  TAACCAACCA  AGGCCGAGTA  CTATCAGCGT-73
-72    GTTGCACATT  TTGGTTATCT  TTAGCACAGT  GTTGAAGATA  ACGAACGAAT  AGTGCCATTA-13
-12    CTGTAACCAA  CC                                                      -1
```

The pGmppo1-AtPPOX1 vector was used to transform *Arabidopsis* model plants in order to generate stable T2 events that were then used for calibration of a PPO pre-determined cut-off concentration that was used in the later step of plant library screening and selection.

Production of *Arabidopsis* seeds having stable T2 generation events began by first introducing the binary vector to *Agrobacterium*. The *Agrobacterium* harboring the pGmppo1-AtPPOX1 gene were then used to transform *Arabidopsis* plants. The transformed *Arabidopsis* seeds were germinated and treated with a selection herbicide to detect transformed plants. Seeds were collected, and T2 *Arabidopsis* seeds were again germinated and treated with a selection herbicide to detect stable T2 events.

Calibration of the selection cut-off value was performed for later use in screening of transformed model plants for increased expression and/or activity of the AtPPOX1 enzyme and related enhancement of the herbicide tolerance (HT) trait. Stable T2 *Arabidopsis* plants transformed with the chimeric pGmppo1-AtPPOX1 gene were treated with the PPO inhibitor type herbicide Flumioxazin using a concentration gradient to calibrate the cut-off concentration. Stable T2 events exhibiting the best tolerance towards the highest concentration of the PPO inhibitor type herbicide Flumioxazin were selected. The selection was based on at least one selection criteria. The pre-determined cut-off concentration was then determined for later use in the selection of promoter variant transgenic plant libraries. The cut-off concentration was determined based on those stable T2 *Arabidopsis* plants transformed with the chimeric pGmppo1-AtPPOX1 gene and exhibiting the best tolerance towards the highest concentration of the PPO inhibitor type herbicide Flumioxazin.

Example 2: Cloning of the Complete Native Soybean (*Glycine max*) PPO1 Gene, for Transformation and Determination of Selection Cut-Off of Enhanced Natural Herbicide Tolerance (HT)

Figure 1B:
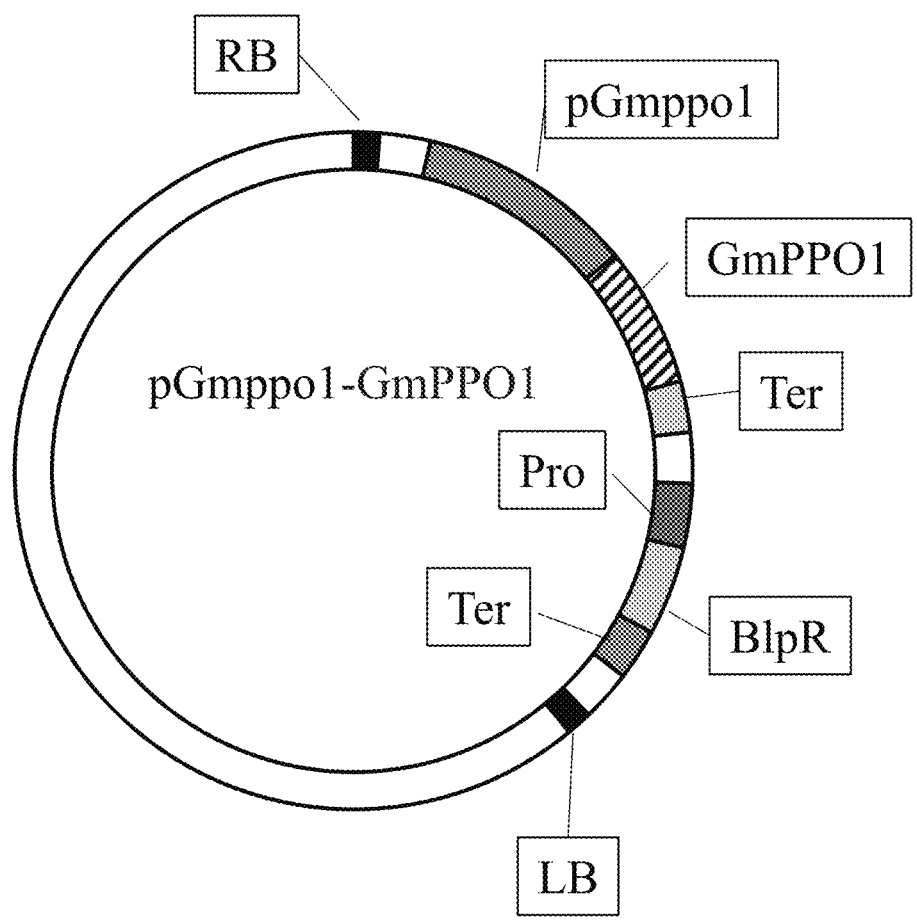

Cloning of the soybean (*Glycine max*) PPO1 Mrna sequence (coding for GmPPO1) (SEQ ID NO: 3) into the binary vector downstream to the promoter pGmppo1, creating pGmppo-GmPPO1 (FIG. 1B).

soybean (Glycine max) PPO1 Mrna sequence (GmPPO1)
SEQ ID NO: 3:
TGTGTATTTTACTGTAACCAACCAAGGCCGAGTACTATCAGCGTGTTGCA

CATTTTGGTTATCTTTAGCACAGTGTTGAAGATAACGAACGAATAGTGCC

ATTACTGTAACCAACCATGGTTTCCGTCTTCAACGAGATCCTATTCCCGC

CGAACCAAACCCTTCTTCGCCCCTCCCTCCATTCCCCAACCTCTTTCTTC

ACCTCTCCCACTCGAAAATTCCCTCGCTCTCGCCCTAACCCTATTCTACG

CTGCTCCATTGCGGAGGAATCCACCGCGTCTCCGCCCAAAACCAGAGACT

CCGCCCCGTGGACTGCGTCGTCGTCGGCGGAGGCGTCAGCGGCCTCTGC

ATCGCCCAGGCCCTCGCCACCAAACACGCCAATGCCAACGTCGTCGTCAC

GGAGGCCCGAGACCGCGTCGGCGGCAACATCACCACGATGGAGAGGGACG

GATACCTCTGGGAAGAAGGCCCCAACAGCTTCCAGCCTTCTGATCCAATG

CTCACCATGGTGGTGGACAGTGGTTTAAAGGATGAGCTTGTTTTGGGGGA

TCCTGATGCACCTCGGTTTGTGTTGTGGAACAGGAAGTTGAGGCCGGTGC

CCGGGAAGCTGACTGATTTGCCTTTCTTTGACTTGATGAGCATTGGTGGC

AAAATCAGGGCTGGCTTTGGTGCGCTTGGAATTCGGCCTCCTCCTCCAGG

TCATGAGGAATCGGTTGAAGAGTTTGTTCGTCGGAACCTTGGTGATGAGG

TTTTTGAACGGTTGATAGAGCCTTTTTGTTCAGGGGTCTATGCAGGCGAT

CCTTCAAAATTAAGTATGAAAGCAGCATTCGGGAAAGTTTGGAAGCTGGA

AAAAAATGGTGGTAGCATTATTGGTGGAACTTTCAAAGCAATACAAGAGA

GAAATGGAGCTTCAAAACCACCTCGAGATCCGCGTCTGCCAAAACCAAAA

GGTCAGACTGTTGGATCTTTCCGGAAGGGACTTACCATGTTGCCTGATGC

AATTTCTGCCAGACTAGGCAACAAAGTAAAGTTATCTTGGAAGCTTTCAA

GTATTAGTAAACTGGATAGTGGAGAGTACAGTTTGACATATGAAACACCA

GAAGGAGTGGTTTCTTTGCAGTGCAAAACTGTTGTCCTGACCATTCCTTC

CTATGTTGCTAGTACATTGCTGCGTCCTCTGTCTGCTGCTGCTGCAGATG

CACTTTCAAAGTTTTATTACCCTCCAGTTGCTGCAGTTTCCATATCCTAT

CCAAAAGAAGCTATTAGATCAGAATGCTTGATAGATGGTGAGTTGAAGGG

GTTTGGTCAATTGCATCCACGTAGCCAAGGAGTGGAAACATTAGGAACTA

TATACAGCTCATCACTATTCCCCAACCGAGCACCACCTGGAAGGGTTCTA

CTCTTGAATTACATTGGAGGAGCAACTAATACTGGAATTTTATCGAAGAC

GGACAGTGAACTTGTGGAAACAGTTGATCGAGATTTGAGGAAAATCCTTA

TAAACCCAAATGCCCAGGATCCATTTGTAGTGGGGGTGAGACTGTGGCCT

CAAGCTATTCCACAGTTCTTAGTTGGCCATCTTGATCTTCTAGATGTTGC

TAAAGCTTCTATCAGAAATACTGGGTTTGAAGGGCTCTTCCTTGGGGGTA

ATTATGTGTCTGGTGTTGCCTTGGGACGATGCGTTGAGGGAGCCTATGAG

GTAGCAGCTGAAGTAAACGATTTTCTCACAAATAGAGTGTACAAATAGTA

GCAGTTTTGTTTTGTGGTGGAATGGGTGATGGGACTCTCGTGTTCCAT

TGAATTATAATAATGTGAAAGTTTCTCAAATTCGTTCGATAGGTTTTTGG

CGGCTTCTATTGCTGATAATGTAAAATCCTCTTTAAGTTTGATTCATTAT

CTACTTCATCCGTATTTAGCAAGGTAGCTATCAGTCTGCCTCTCCATTAT

TCCCCTCTATTCTTGGAGAGTTGGTAGATTTTAACTTGTTACTATATATG

TAAGTCCAGGCAATGCTCTGTAACAATGCATGAGTTACATGATTATAATA

TGTCTTTTTATTTGAATC

The pGmppo-GmPPO1 vector was used to transform *Arabidopsis* model plants in order to generate stable T2 events that were then used for calibration of a PPO predetermined cut-off concentration that was used in the later step of plant library screening and selection.

The production of *Arabidopsis* seeds having stable T2 generation events, and the calibration of the selection cut-off value (for later use in screening of transformed model plants for increased expression and/or activity of the GmPPO1 enzyme), were performed according to the same guidelines as described hereinabove in Example 1.

Example 3: Algorithm Analysis of the Native Soybean Ppo1 Promoter (pGmppo1) for Detection of Putative Hot-Spots A unique algorithm is utilized, for analyzing non-coding regulatory elements in pGmppo1 and predicting putative "hot-spots" for DNA binding proteins that take part in the process of transcription. These include transcription factors and other transcription-related proteins that interact with the DNA in a sequence-specific manner. FIG. 2 illustrates the general architecture of a plant gene, including regulatory regions and downstream coding sequence.

The algorithm utilizes available information on plant regulatory elements sequences derived from public databases such as PlantCARE (Plant cis-Acting Regulatory Elements), PLACE (Plant cis-Acting Regulatory DNA Elements) and RegSite (Plant-oriented collections of transcription regulatory elements). The algorithm is then applied for analysis of the native soybean PPO1 gene and predictions of hot-spots that may promote the desired change of enhanced transcription activity from the pGmppo1.

The algorithm receives SEQ ID NO: 2 as an input sequence (the sequence of pGmppo1). The typical architecture of the pGmppo1 promoter is analyzed to recognize specific regulatory elements therein. This includes analysis of the proximal promoter (including core promoter) and the distal promoter. The promotor regions are identified by analyzing the several hundred nucleotides around the TSS, considered as the core/proximal promoter, for example for identifying elements regulating transcription start site (TSS) selection, and by analyzing the following thousands and more nucleotides further upstream of the TSS, considered as the distal promoter, for example for the existence of regulatory cis-elements that can function as transcription enhancers and may perform an accessory role in increasing the transcriptional activity The algorithm identifies hot-spots of putative regulatory elements in pGmppo1, process and integrates data, and then predict sites on the promoter sequence suitable for genetic manipulation/editing thereby predicting potentially new regulatory elements having new attributes in respect to the gene's expression pattern. In case of the PPO1 gene product the desired change is increased expression and activity of the enzyme. This can be achieved, for example, by introducing into hot-spot genetic changes that enforce the binding activity of transcription activators or prevent the binding activity of suppressors. Targeting the hot-spots on the pGmppo1 promoter sequence may achieve the desired increase in the gene's transcription activity at a specific developmental growth phase of the plant and in specific tissues in which expression of the gene is usually low, in addition to enhancing the number of transcription events and strength of already active promoters within the plant cells.

Example 4: Generation of an In-Planta Genetic Library of a Large Collection of Altered Soybean Ppo1 Promoter (pGmppo1) Elements for High-Throughput Evaluation of Enhanced Herbicide Tolerance (HT) in *Arabidopsis*

Construction of mutagenized genetic libraries comprising large collections of altered regulatory elements was performed by randomly directing genetic changes into the soybean ppo1 promoter pGmppo1 thereby altering random regions of the regulatory elements.

The regulatory region (between −1 bp to −1273 bp) upstream to GmPPO1 gene transcription start site (TSS) was amplified from soybean genomic DNA as set forth in SEQ ID NO: 2. The PCR fragments were then subjected to random mutagenesis using Error Prone PCR methodology according to manufacture instructions. The mutation rate was increased by the changes in the $Mn^{2+}$ and $Mg^{2+}$ ion concentrations along with unbalancing the available nucleotide pools. The manipulation of mutagenesis was monitored by adjusting the number of amplification cycles allowing choice of mutation degree.

The resulting population of molecules carrying random point mutations was cloned into the binary vector (Ppa35H) upstream to AtPPOx1 coding region as set forth in SEQ ID NO: 1 generating large pools of $10^5$ clones.

Next, pGmppo1 genetic variant libraries were validated, and the quality of the libraries was tested by random sequencing of the library preceding a statistical analysis of nucleotide distribution at the mutation sites. The results of the analysis are presented in FIG. 3B showing even distribution and randomization of the mutagenesis with no bias toward a specific location. These two libraries were cloned upstream to the GmPPO1 or the AtPPOX1 coding sequence, creating a chimeric pGmppo1-AtPPOX1 or pGmppo1-GmPPO1, mixed and used for the high throughput transformation into *Arabidopsis* plants.

Following preparation and quality validation of a pGmppo1 variant library, the obtained chimeric pGmppo1-AtPPOX1 (or pGmppo1-GmPPO1) nucleic acid was introduced to *Agrobacterium* and transformed into *Arabidopsis* plants utilizing a high-throughput transformation method (floral dip), creating in-planta promoter libraries each containing a collection of approximately $10^3$-$10^5$ transgenic pGmppo1-AtPPOX1 (or pGmppo1-GmPPO1) plants, in which, on average each plant carries a single genetically altered regulatory element having at least one or more genetic changes in the pGmppo1. The above-described process is illustrated in steps I, II and III of FIG. 3A Example 5—Screening and Selection of *Arabidopsis* Plants for Enhanced Herbicide Tolerance (HT) and Identification of the Underlying Genetic Changes The evaluation and selection of improved Herbicide Tolerance (HT) trait in model plants was performed by a high-throughput in-planta functional screening assay using PPO inhibitor herbicide spraying to easily identify low-frequency mutants. First, transgenic pGmppo1-AtPPOX1 (or pGmppo1-GmPPO1) T1 seedlings were subjected to Glufosinate ammonium to select the transformed T1 events. Thereafter, 14 days old seedlings were subjected to $1 \times 10^{-3}\%$ Oxadiazon (Star) or Flumioxazin (Strike) treatment, in accordance with their previously determined cut-off concentration. Plants showing high tolerance towards the cut-off concentrations of Oxadiazon (Star) or Flumioxazin (Strike), were selected for their possible resistance to the herbicide. The level of tolerance was determined based on the damage to leaves which is the same selection criteria used in the preliminary experiments with the native promoter in order to establish the cut-off concentration. The above-described process is illustrated in step IV of FIG. 3A Advantageously, FIG. 3C demonstrate a representative result of the functional screen showing a non-damaged PPO tolerant plant (i.e., "healthy" plant, white dashed circle), containing 'positive mutation' (i.e., that enhance-HT) in the PPO promoter, surrounded by multiple susceptible plants (having damaged leaves), containing other non-tolerant enhancing mutations in the PPO promoters.

Next, the transgenes of selected plants were PCR amplified and sequenced to identify the positions and positive mutations in pGmppo1 that enhanced HT. The described process is illustrated in step V of FIG. 3A The mutated sequences of pGmppo1 that were identified by sequencing of the transgenes are denoted by any one of SEQ ID NOs: 4-63. The mutations and their positions are summarized in Table 1—describing hot spots in the soybean ppo1 promoter (pGmppo1), and in Table 2—describing mutations identified in soybean PPO1 promoter (pGmppo1).

The results of the sequencing analysis are illustrated in FIG. 3D by showing the distribution of the mutations as they occurred along the nucleic acid sequence of the soybean PPO1 promoter (pGmppo1), in 14 different resistant events discovered by the functional herbicide selection assay. Advantageously, the analysis revealed that out of 14 independent resistant events each independent resistant event shares at least one identical mutation with another resistant event at the same position, suggesting that these seven positions may be major hot spots positions that when mutated confer enhanced/improved herbicide tolerance (HT) trait.

These seven major hot spots in the soybean PPO1 promoter are illustrated in FIG. 3D (marked in rectangles) as identified in the 14 events, and include the following positions with respect to SEQ ID NO: 2, wherein (-) denotes an upstream position relative to the Transcription Start Site (TSS): [−1229A], [−1105T], [−668A], [−481T], [−189A], [−70T] and [−61T]. The mutations identified at these 7 hot spot positions in pGmppo1, and their occurrence as in the resistant events selected in the functional in-plant screen, were summarized in Table 1 in the detailed description of this instant application.

Example 6—Differential Resistance Assay

To evaluate the tolerance of the selected mutation bearing promoters to other, additional PPO herbicides, the selected putative promoters, are used to re-transform *Arabidopsis* plants and are tested again for resistance against different PPO herbicides, as described below.

T2 plants showing good tolerance to Oxadiazon (Star) or Flumioxazin (Strike) PPO herbicides and harboring a desired genetic change as demonstrated in any one of the transgenes that were sequenced from the resistant events previously identified, are grown under glufosinate ammonium to assure the transgene presence. These plants are then being subjected to different herbicides including Oxadiazon (Star), Flumioxazin (Strike), and other PPO herbicides at concentrations of $10^{-3}$, $5 \times 10^{-3}$, $10^{-2}$, $5 \times 10^{-2}$, $10^{-1}$, $5 \times 10^{-1}$ of the active ingredient, in order to assess their differential resistance. Best performing plants are then re-evaluated for their pGmppo1 promoter region genetic changes.

Figure 4:
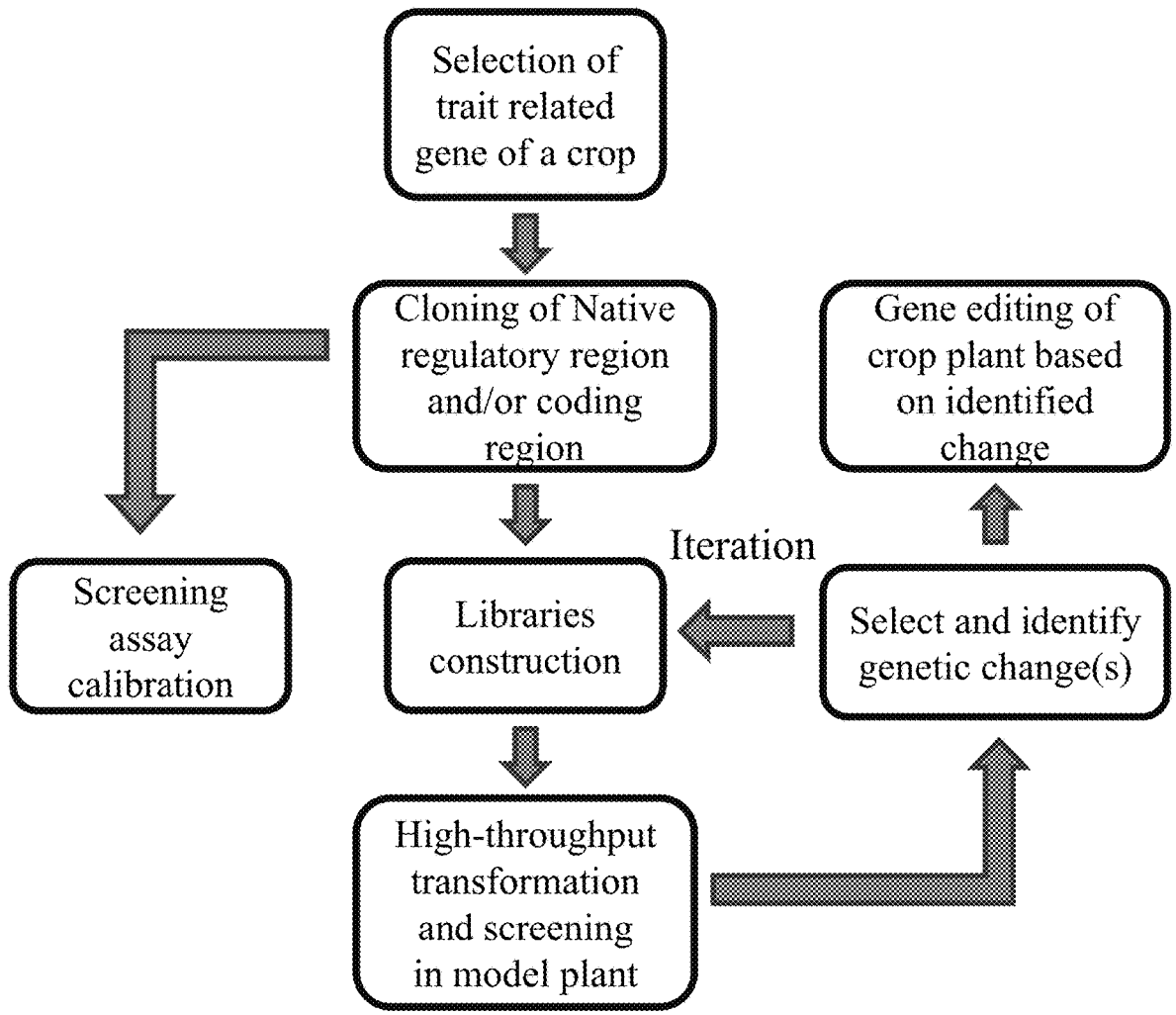
FIG. 4 schematically illustrates the process of optimizing trait-related gene expression in plants. Following the selection and cloning of a native trait-related gene's regulatory elements and/or coding sequence elements, the screening assay is calibrated to pre-determine selection conditions. In parallel, genetic libraries comprising a large collection of $10^3$-$10^6$ altered genetic regulatory elements and/or altered coding sequence elements are constructed, transformed, and screened in a high-throughput manner in a model plant. Selected genetic alterations that underly the desired change in gene expression of the trait-related gene/reporter are identified and re-transformed and subsequently, an endogenous promoter/coding sequence of a crop plant may be gene-edited to replica the changes identified as leading to optimized expression.

A schematic overview of the process, presenting the general workflow utilized for improving a trait, such as Herbicide Tolerance (HT), in plants, is illustrated in FIG. 4.

Example 7—Generation of an Enhanced Herbicide Tolerance (HT) Gene-Edited Soybean Crop Plant The genetic change identified in model plants expressing the desired level of resiliency are introduced into the desired *Glycine max* crop plant utilizing gene-editing methods in order to generate genetically edited or modified, soybeans plants possessing enhanced Herbicide Tolerance HT.

Example 8—Cloning of the Soybean (*Glycine max*) Ppo1 Promoter (pGmppo1) with GFP for Evaluation of Enhanced Fluorescence in Stably Transformed *Arabidopsis* Plants The expression of the non-native trait-related sequence of a reporter protein such as a fluorescent protein leads to the manifestation of a phenotypic trait of having a detectable fluorescent signal. A native promoter of soybean ppo1 promoter (pGmppo1) is cloned upstream to a sequence encoding a coding sequence of GFP, producing pGmppo1-GFP.

The evaluation of improved fluorescence in model plants is performed by a high-throughput screening process using detection of fluorescence levels according to a pre-determined green fluorescence cut-off. Plants showing higher fluorescence levels than the green fluorescence cut-off are selected for their possible desired change in expression associated with an altered promoter of soybean (pGmX). The level of fluorescence is determined based on the same at least one selection criteria used in the preliminary experiments with the native promoter in order to establish the green fluorescence cut-off concentration.

Example 9—Cloning of the Soybean (*Glycine max*) Promoter (pGmX) with GFP for Evaluation of Enhanced Fluorescence in Transient Expression in Soybean Plants The evaluation of improved fluorescence in target crop plants is performed by a screening process using detection of fluorescence levels according to a pre-determined green fluorescence cut-off. A native promoter of soybean (pGmX) is cloned into a binary vector upstream to a sequence coding for GFP, producing a pGmX-GFP. Transient expression of the GFP in soybean leaves is achieved by infiltration of *Agrobacterium tumefaciens* harboring the binary vector into the leaves. Leaves showing higher fluorescence levels than the green fluorescence cut-off are selected for their possible desired change in expression associated with altered regulatory elements in the promoter of soybean (pGmX). The level of fluorescence is determined based on the same at least one selection criteria used in the preliminary cut-off experiments with the native promoter.

Example 10—Cloning of a Native Regulatory Element with the Herbicide Tolerance (HT) Related Protoporphyrinogen Oxidase (PPOX1) Gene of *Arabidopsis* (AtPPOX1) for Evaluation of a Desired Change in Expression The expression of the coding sequence of the Herbicide Tolerance (HT) related Protoporphyrinogen Oxidase (PPOX1) gene of *Arabidopsis* (AtPPOX1) or soybean PPO1 (GmPPO1) leads to the manifestation of a desirable/beneficial phenotypic trait of having enhanced resistance to the PPO-inhibitor Oxadiazon, Flumioxazin, or Carfentrazone Ethyl, or other inhibitor, thereby allowing utilizing it as a reporter gene for the high-throughput screening of model plants manifesting a desired change in expression from an altered regulatory element and/or coding sequence of any native gene of any desired crop plant that is functionally coupled to the trait.

The *Arabidopsis* PPOX1 (AtPPOX1) or soybean PPO1 (GmPPO1) is used as a reporter gene that is cloned downstream to the promoter of a native trait-related gene for evaluation of the desired change in expression of Protoporphyrinogen Oxidase that is associated with a genetic change introduced to the promoter of the native gene. Reference is made to FIG. 2B.

In addition, The *Arabidopsis* PPOX1 (AtPPOX1) or soybean PPO1 (GmPPO1) reporter gene is cloned as a fusion protein downstream to the coding sequence of a native trait-related gene for evaluation of the desired change in expression of Protoporphyrinogen Oxidase that is associated with a genetic change introduced to the coding sequence of the native gene.

Reference is made to FIG. 2C.

The invention claimed is:

1. A method for in-planta high throughput evaluation of endogenous genetic regulatory elements of a crop plant, the method comprising the steps of:
  a. obtaining a nucleic acid of a native promoter regulatory element of a trait-related gene, coupling it to a coding sequence of a reporter gene having a native function in the crop plant; wherein the regulatory element is of the crop plant;
  b. introducing one or more random genetic changes in each of a plurality of copies of the native regulatory element, thereby obtaining a genetic library comprising a large collection of altered regulatory elements;
  c. introducing the genetic library into model plants, utilizing high throughput stable transformation, such that on average each model plant receives a single altered regulatory element;
  d. screening the transformed model plants, wherein the screening comprises selecting a model plant having a desired change in phenotype thereof, said change is correlated to expression level of the reporter gene; and
  e. identifying the one or more genetic changes in the altered regulatory element of the selected model plant.

2. The method according to claim 1, further comprising modifying the native regulatory element of the trait-related gene of the crop plant, based on the one or more identified genetic changes in the altered regulatory element of the selected model plant and/or wherein the crop plant is generated using gene-editing tools, to generate a modified crop plant.

3. The method according to claim 1, wherein the native regulatory element is located upstream, downstream, or within a coding sequence of the reporter gene.

4. The method according to claim 1, wherein the reporter gene coding sequence is of the same or different origin as the regulatory element of the trait-related gene.

5. The method according to claim 1, wherein the one or more genetic changes are selected from one or more: point mutations, domain swapping, rearrangement of cis-elements, enhancers addition and/or deletion of silencers.

6. The method according to claim 1, wherein said introducing the genetic library into model plants comprises cloning into Agrobacterium binary vectors, and/or wherein said screening of a model plant having the desired change in the expression level of the reporter gene comprises meeting a pre-determined cut-off.

7. The method according to claim 1, wherein the desired change in the expression level/phenotype of the trait-related gene/reporter gene comprises a change in transcription activity of the altered regulatory element.

8. The method according to claim 1, wherein the desired change in the expression level/phenotype of the trait-related gene/reporter gene comprises change in time, development stage, cellular localization, tissue specific and/or strength of expression.

9. The method according to claim 1, wherein the desired change in the expression level of the trait-related gene/reporter gene comprises an increased expression associated with increased gene function and/or activity, and wherein the increased function and/or activity of the trait-related gene/reporter gene confers enhanced plant resistance or enhanced plant yield.

10. The method according to claim 9, wherein the enhanced resistance comprises tolerance to herbicides, insects, diseases, heat, cold, drought, biotic or abiotic stress.

11. The method according to claim 9, wherein the enhanced resistance comprises herbicide tolerance (HT).

12. The method according to claim 11, wherein the herbicide tolerance (HT) comprises increased expression of a native enzyme that overcomes the herbicide's active ingredient concentration in the plant thereby increasing natural resistance, and wherein the native enzyme is Protoporphyrinogen Oxidase (PPO1), or p-hydroxyphenylpyruvate dioxygenase (HPPD), or 5-enolpyruvylshikimate 3-phosphate synthase (EPSPS), or Glutamine synthase, or acetolactate synthase (ALS enzyme), or 7,8-dihydropteroate synthase, or acetyl-CoA carboxylase (ACCase).

* * * * *

SEQUENCE LISTING

```
Sequence total quantity: 63
SEQ ID NO: 1            moltype = RNA   length = 1804
FEATURE                 Location/Qualifiers
source                  1..1804
                        mol_type = mRNA
                        organism = Arabidopsis thaliana
SEQUENCE: 1
gaagaagatt acccaatctg aaaaaaacca agaagctgac aaaattccga attctctgcg  60
atttccatgg agttatctct tctccgtccg acgactcaat cgcttcttcc gtcgttttcg 120
aagcccaatc tccgattaaa tgtttataag cctcttagac tccgttgttc agtggccggt 180
ggaccaaccg tcggatcttc aaaaatcgaa ggcggaggag gcaccaccat cacgacggat 240
tgtgtgattg tcggcggagg tattagtggt ctttgcatcg ctcaggcgct tgctactaag 300
catcctgatg ctgctccgaa tttaattgtg accgaggcta aggatcgtgt tggaggcaac 360
attatcactc gtgaagagaa tggttttctc tgggaagaag gtcccaatag ttttcaaccg 420
tctgatccta tgctcactat ggtggtagat agtggtttga aggatgattt ggtgttggga 480
gatcctactg cgccaaggtt tgtgttgtgg aatgggaaat tgaggccggt tccatcgaag 540
ctaacagact taccgttctt tgatttgatg agtattggtg ggaagattag agctggtttt 600
ggtgcacttg gcattcgacc gtcacctcca ggtcgtgaag aatctgtgga ggagtttgta 660
cggcgtaacc tcggtgatga ggttttttgag cgcctgattg aaccgttttg ttcaggtgtt 720
tatgctggtg atccttcaaa actgagcatg aaagcagcgt ttgggaaggt ttggaaacta 780
```

```
gagcaaaatg gtggaagcat aataggtggt acttttaagg caattcagga gaggaaaaac  840
gctcccaagg cagaacgaga cccgcgcctg ccaaaaccac agggccaaac agttggttct  900
ttcaggaagg gacttcgaat gttgccagaa gcaatatctg caagattagg tagcaaagtt  960
aagttgtctt ggaagctctc aggtatcact aagctggaga gcggaggata caacttaaca 1020
tatgacgactc cagatggttt agtttccgtg cagagcaaaa gtgttgtaat gacggtgcca 1080
tctcatgttg caagtggtct cttgcgcccc ctttctgaat ctgctgcaaa tgcactctca 1140
aaactatatt acccaccagt tgcagcagta tctatctcgt acccgaaaga agcaatccga 1200
acagaatgtt tgatagatgg tgaactaaag gttttgggc aattgcatcc acgcacgcaa 1260
ggagttgaaa cattaggaac tatctacagc tcctcactct ttccaaatcg cgcaccgaca 1320
ggaagaattt tgctgttgaa ctacattggc gggtctacaa acaccggaat tctgtccaag 1380
tctgaaggtg agttagtgga agcagttgac agagatttga ggaaaatgct aattaagcct 1440
aattcgaccg atccacttaa attaggagtt agggtatggc ctcaagccat tcctcagttt 1500
ctagttggtc acttttgatat ccttgacacg gctaaatatc ctctaacgtc ttcgggctac 1560
gaagggctat ttttggggtgg caattacgtc gctggtgtag ccttaggccg gtgtgtagaa 1620
ggcgcatatg aaaccgcgat tgaggtcaac aacttcatgt cacggtacgc ttacaagtaa 1680
atgtaaaaca ttaaatctcc cagcttgcgt gagtttatt aaatattttg agatatcaaa 1740
cttcaatttc attttgatac atagatttga gttatagtta tatttaggag aagggtcttt 1800
ggtt                                                              1804

SEQ ID NO: 2          moltype = DNA  length = 1272
FEATURE               Location/Qualifiers
source                1..1272
                      mol_type = genomic DNA
                      organism = Glycine max
SEQUENCE: 2
attaagaagc ttacaaagag attgggaact aaaactactt aaaaaaaaag gaattaaaat   60
caatttcaac caaattataa gagacttaag atacattta ttctaggaaa caatattact   120
tctggacttt taaacaagaa acaaaaaata aattaattaa gatcaattga atagttaatt   180
taattatttt taatcaataa tattataaat ttatattta ttctaaaaat gtttatcaaa   240
ctaagtaaca tctggttta tatttgttca gagaaaatgc gtagctaact ctatgcatta   300
aacaaaaaaa agaaattttt cttcaattt ttcgattttt ccatttgatt ttattgtttg   360
ggaattattt tcttaatt cttccattc tatcaatgaa gaatctataa gaattctcaa    420
ttccatatca tttcattttt aaaattaa tcgtaatgga aataagaaag actaatattc   480
ctttggaaat attacccgaa tgatatttct tctcttatag ataatagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactaa atctacttac aaagaaaata   780
aaatgagcga cttatatttt ttattagctt taatgattaa tctttataaa aaattactaa   840
aaatatttaa tgatacgtca tttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt ccctataaaa aaattattct aaatattagc  1020
ttttatttga cttcaaaata agttattgct tttataataa taatgatatg ataaaaaaaa  1080
aaaactaata gataaaaaaa gtacttagaa aacattttt caagaacgtt aaaggtaaag  1140
tttagatgga ggcaattgtg tatttactg taaccaacca aggccgagta ctatcagcgt  1200
gttgcacatt ttggttatct ttagcacagt gttgaagata cgaacgaat agtgccatta  1260
ctgtaaccaa cc                                                     1272

SEQ ID NO: 3          moltype = RNA  length = 2068
FEATURE               Location/Qualifiers
source                1..2068
                      mol_type = mRNA
                      organism = Glycine max
SEQUENCE: 3
tgtgtatttt actgtaacca accaaggccg agtactatca gcgtgttgca cattttggtt   60
atctttagca cagtgttgaa gataacgaac gaatagtgcc attactgtaa ccaaccatgg  120
tttccgtctt caacgagatc ctattcccgc cgaaccaaac cctcttcgc cctccctcc   180
attccccaac ctcttctcc acctctccca ctcgaaaatt ccctcgctct cgccctaacc   240
ctattctacg ctgctccatt gcggaggaat ccaccgcgtc tccgcccaaa accagagact   300
ccgccccgt ggactgcgtc gtcgtcggcg gaggcgtcag cggcctctgc atcgcccagg   360
ccctcgccac caaacacgcc aatgccaacg tcgtcgtcac ggaggcccga gaccgcgtcg   420
gcggcaacat caccacgatg gagagggacg gatacctctg ggaagaaggc cccaacagct   480
tccagccttc tgatccaatg ctcaccatgg tggtggacag tggtttaaag gatgagcttg   540
ttttgggga tcctgatgca cctcggtttg tgttgtgaa caggaagttg aggccggtgc   600
ccggaagct gactgatttg ccttttcttg acttgatgag cattggtggc aaaatcaggg   660
ctggcttttg tgcgcttgga attcggcctc tcctccagg tcatgaggaa tcggttgaag   720
agtttgttcg tcggaacctt ggtgatgagg ttttttgaacg gtttgataga gccttttgtt   780
cagggggtcta tgcaggcgat ccttcaaaat taagtatgaa agcagcattc gggaaagttt   840
ggaagctgaa aaaaatggt ggtagcatta ttggtgataa tttcaaaagca atacaagaga   900
gaaatggagc ttcaaaacca cctcgagatc cgcgtctgcc aaaaccaaaa ggtcagactg   960
ttggatcttt ccgaaggga cttaccatgt tgcctgatgc aatttctgcc agactaggca  1020
acaaagtaaa gttatctgg aagctttcaa gtattagtaa actggatagt ggagagtaca  1080
gtttgacata tgaaacacca gaaggagtgg tttcttgca gtgcaaaact gttgtcctga  1140
ccatccttc ctatgttgct agtacattgc tgcgtcttgct gctgcagatg  1200
cactttcaaa gtttattac cctccagttg ctgcagttc catatcctat ccaaaagaag  1260
ctattagatc agaatgcttg atagatggtg agttgaaggg gtttggtcaa ttgcatccac  1320
gtagccaagg agtggaaaca ttaggaacta tacagctcc atcactattc cccaaccgag  1380
cacccacctg aagggttcta ctcttgaatt acattggagg agcaactaat actggaattt  1440
tatcgaagac ggacagtgaa cttgtggaaa cagttgatcg agatttgagg aaatccctta  1500
```

```
taaacccaaa tgcccaggat ccatttgtag tgggggtgag actgtggcct caagctattc  1560
cacagttctt agttggccat cttgatcttc tagatgttgc taaagcttct atcagaaata  1620
ctgggtttga agggctcttc cttggggta attatgtgtc tggtgttgcc ttgggacgat   1680
gcgttgaggg agcctatgag gtagcagctg aagtaaacga ttttctcaca aatagagtgt  1740
acaaatagta gcagttttg tttttgtggt ggaatggatg atgggactct cgtgttccat   1800
tgaattataa taatgtgaaa gtttctcaaa ttcgttcgat aggttttttgg cggcttctat  1860
tgctgataat gtaaaatcct cttaagttt gattcattat ctacttcatc cgtatttagc   1920
aaggtagcta tcagtctgcc tctccattat tcccctctat tcttggagag ttggtagatt   1980
ttaacttgtt actatatatg taagtccagg caatgctctg taacaatgca tgagttacat   2040
gattataata tgtctttta tttgaatc                                      2068

SEQ ID NO: 4          moltype = DNA   length = 1272
FEATURE               Location/Qualifiers
source                1..1272
                      mol_type = other DNA
                      organism = synthetic construct
SEQUENCE: 4
attaagaagc ttacaaagag attgggaact aaaactactt aaacaaaaag gaattaaaat   60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagcaact ctatgcatta    300
aacaaaaaaa agaaaatttt cttcaattt ttcgattttt ccatttgatt ttattgtttg    360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactac atctacttac aaagaaaata   780
aaatgagcga cttatatttt ttattagctt taatgattaa tctttataaa aaattactaa   840
aaatatttaa tgatacgtca ttttccaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaa aaattattcc aaatattagc   1020
tttatttga cttcaaaata agttattgct tttataataa taatgatatg ataaaaaaaa   1080
aaaactaata gataaaaaaa gtacttagaa aacatttttt caagaacgtt aaaggtaaag   1140
tttagatgga ggcaattgtg tattttactg taaccaacca aggccgagta ctatcagcgt   1200
gttgcacatt ttggttatct ttagcacagt gttgaagata acgaacgaat agtgccatta   1260
ctgtaaccaa cc                                                      1272

SEQ ID NO: 5          moltype = DNA   length = 1272
FEATURE               Location/Qualifiers
source                1..1272
                      mol_type = other DNA
                      organism = synthetic construct
SEQUENCE: 5
attaagaagc ttacaaagag attgggaact aaaactactt aaaaaaaaag gaattaaaat   60
caatttcaac caaattataa gagacttaag atacatttta ttctaggaaa caatattact   120
tctggacttt taaacaagaa acaaaaaata aattaattaa gatcaatcga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttcaattt ttcgattttt ccatttgatt ttattgtttg    360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactac atctacttac aaagaaaata   780
aaatgagcga cttatatttt ttattagctt taatgattaa tctttataaa aaattactaa   840
aaatatttaa tgatacgtca ttttccaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc   1020
tttatttga cttcaaaata agttattgct tttataataa taatgatatg ataaaaaaaa   1080
aaaactaata gataaaaaaa gtacttagaa aacatttttt caagaacgtt aaaggtaaag   1140
tttagatgga ggcaattgtg tattttactg taaccaacca aggccgagta ctatcagcgt   1200
gttgcacatt ttggttatct ttagcacagt gttgaagata acgaacgaat agtgccatta   1260
ctgtaaccaa cc                                                      1272

SEQ ID NO: 6          moltype = DNA   length = 1271
FEATURE               Location/Qualifiers
source                1..1271
                      mol_type = other DNA
                      organism = synthetic construct
SEQUENCE: 6
attaagaagc ttacaaagag attgggaact aaaactactt aaaaaaaaag gaattaaaat   60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
```

```
ctaagtaaca tctggtttta tatttgttca gagaaaatgc gtagctaact ctatgcatta    300
aacaaaaaaa agaaaatttt ctttcaattt ttcgattttt ccatttgatt ttattgtttg    360
ggaattattt ttccttaatt cttccattc tatcaatgaa gaatctataa gaattctcaa     420
ttccatatca tttcattttt aaaaatttaa tcgtaatgga aataagaaag actaatattc    480
ctttggaaat attcccgaa  tgatatttct tctcttatag gtaataagta tattatttgt    540
aattcaatag aacaaatttc ttatattgtt attagttcaa taaatatatt tatttacata    600
aaaataataa aaggagatct atcttaaatt cttgtatatg aaatttgatt ctcgtgaatg    660
aaacaaaaca taaaaaaaga tcatgagtaa cttgatgatg ctattgccat tattaatagt    720
ttaataatta ttccttaaaa taaatagttc aataactata tctacttaca aagaaaataa    780
aatgagcgac ttatattttt tattagcttt aatgattaat ctttataaaa aattactaaa    840
aatatttaat gatacgtcat tttcaatta  tgtttctttc ctttactaaa ctcgaatcaa    900
atacaaaaat aaattgtttg agtgccgaaa gtccgaaact tattatttga cttcaaaata    960
agttattgtt tttatcttat aataatcgtc ctataaaaa  aattattcta aatattagct    1020
tttatttgac ttcaaaataa gttattgctt ttataataa  aatgatatga taaaaaaaaa    1080
aaactaatag ataaaaaaag tacttagaaa acatttttc  aagaacgtta aaggtaaagt    1140
ttagatggag gcaattgtgt attttactgt aaccaaccaa ggccgagtac tatcagcgtt    1200
gttgcacatt tggttatctt tagcacagtg ttgaagataa cgaacgaata gtgccattac    1260
tgtaaccaac c                                                        1271

SEQ ID NO: 7              moltype = DNA   length = 1272
FEATURE                   Location/Qualifiers
source                    1..1272
                          mol_type = other DNA
                          organism = synthetic construct
SEQUENCE: 7
attaagaagc ttacaaagag attgggaact aaaactactt aaaaaaaaag gaattaaaat    60
caatttcaac caaattataa gagacttaag atacattta  ttctaggaaa caatattact    120
tctggactttt aaacaagaa acaaaaaata aattaattaa gatcaattga atagttaatt    180
taattatttt taatcaataa tattataaat ttatatttta ttctaaaat  gtttatcaaa    240
ctaagtaaca tctggtttta tatttgttca gagaaaatgc gtagctaact ctatgcatta    300
aacaaaaaaa agaaaatttt ctttcaattt ttcgattttt ccatttgatt ttattgtttg    360
ggaattattt ttccttaatt cttccattc tatcaatgaa gaatctataa gaattctcaa     420
ttccatatca tttcattttt aaaaatttaa tcgtaatgga aataagaaag actaatattc    480
ctttggaaat attcccgaa  tgatatttct tctcttatag gtaataagta tattatttgt    540
aattcaatag aacaaatttc ttatattgtt attagttcaa taaatatatt tatttacata    600
aaaagtaata aaggagatc  tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactat atctacttac aagaaaata    780
aatgagcga  cttatatttt ttattagctt taatgattaa tctttataaa aattactaaa    840
aatatttaa  tgatacgtca ttttcaatt  atgtttcttt cctttactaa actcgaatca    900
aatacaaaa  taaattgttt gagtgccgaa agtccgaaac ttattatttg acttcaaaat    960
aagttattgt tttatctta  taataatcgt cctataaaaa aattattct  aatattagc    1020
ttttatttga cttcaaaata agttattgct tttataataa taatgatatg ataaaaaaaa    1080
aaaactaata gataaaaaaa gtacttagaa acattttttt caagaacgtt aaaggtaaag    1140
tttagatgga ggcaattgtg tattttactg taaccaacca aggccgagta ctatcagcgt    1200
gttgcacatt tggttatct  ttagcacagt gttgaagata acgaacgaat agtgccatta    1260
ctgtaaccaa cc                                                        1272

SEQ ID NO: 8              moltype = DNA   length = 1272
FEATURE                   Location/Qualifiers
source                    1..1272
                          mol_type = other DNA
                          organism = synthetic construct
SEQUENCE: 8
attaagaagc ttacaaagag attgggaact aaaactactt aaaaaaaaag gaattaaaat    60
caatttcaac caaattataa gagacttaag atacattta  ttctaggaaa caatattact    120
tctggactttt aaacaagaa acaaaaaata aattaattaa gatcaattga atagttaatt    180
taattatttt taatcaataa tattataaat ttatatttta ttctaaaat  gtttatcaaa    240
ctaagtaaca tctggtttta tatttgttca gagaaaatgc gtagctaact ctatgcatta    300
aacaaaaaaa agaaaatttt ctttcaattt ttcgattttt ccatttgatt ttattgtttg    360
ggaattattt ttccttaatt cttccattc tatcaatgaa gaatctataa gaattctcaa     420
ttccatatca tttcattttt aaaaatttaa tcgtaatgga aataagaaag actaatattc    480
ctttggaaat attcccgaa  tgatatttct tctcttatag gtaataagta tattatttgt    540
aattcaatag aacaaatttc ttatattgtt attagttcaa taaatatatt tatttacata    600
aaaataataa aaggagatc  tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactat atctacttac aagaaaata    780
aatgagcga  cgtatatttt ttattagctt taatgattaa tctttataaa aattactaaa    840
aatatttaa  tgatacgtca ttttcaatt  atgtttcttt cctttactaa actcgaatca    900
aatacaaaa  taaattgttt gagtgccgaa agtccgaaac ttattatttg acttcaaaat    960
aagttattgt tttatctta  taataatcgt cctataaaaa aattattct  aatattagc    1020
ttttatttga cttcaaaata agttattgct tttataataa taatgatatg ataaaaaaaa    1080
aaaactaata gataaaaaaa gtacttagaa acattttttt caagaacgtt aaaggtaaag    1140
tttagatgga ggcaattgtg tattttactg taaccaacca aggccgagta ctatcagcgt    1200
gttgcacatt tggttatctt tagcacagt  gttgaagata acgaacgaat agtgccatta    1260
ctgtaaccaa cc                                                        1272

SEQ ID NO: 9              moltype = DNA   length = 1273
FEATURE                   Location/Qualifiers
```

|   |   |   |
|---|---|---|
| source | 1..1273 | |
| | mol_type = other DNA | |
| | organism = synthetic construct | |

SEQUENCE: 9

```
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt ctttcaattt ttcgattttt ccatttgatt ttattgtttg   360
ggaattattt ttccttaatt cttccattc tatcaatgaa gaatctataa gaattctcaa   420
ttccatatca tttcatttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca tttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc  1020
ttttatttga cttcaaaata agttattgct tttataataa taatgatatg ataaaaaaaa  1080
aaaaactaat agataaaaaa agtacttaga aaacatttttt tcaagaacgt taaaggtaaa  1140
gtttagatgg aggcaattgt gtatttact gtaaccaacc aaggccgagt actatcagcg  1200
tgttgcacat tttggttatc tttagcacag tgttgaagat aacgaacgaa tagtgccatt  1260
actgtaacca acc                                                    1273
```

| SEQ ID NO: 10 | moltype = DNA  length = 1272 | |
| FEATURE | Location/Qualifiers | |
| source | 1..1272 | |
| | mol_type = other DNA | |
| | organism = synthetic construct | |

SEQUENCE: 10

```
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt ctttcaattt ttcgattttt ccatttgatt ttattgtttg   360
ggaattattt ttccttaatt cttccattc tatcaatgaa gaatctataa gaattctcaa   420
ttccatatca tttcatttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca tttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc  1020
ttttatttga cttcaaaata agttattgct tttaataa taatgatatg ataaaaaaaa  1080
aaacctaata gataaaaaaa gtacttagaa aacatttttt caagaacgtt aaaggtaaag  1140
tttagatgga ggcaattgtg tatttactg taaccaacca aggccgagta ctatcagcgt  1200
gttgcacatt ttggttatct ttagcacagt gttgaagata acgaacgaat agtgccatta  1260
ctgtaaccaa cc                                                     1272
```

| SEQ ID NO: 11 | moltype = DNA  length = 1271 | |
| FEATURE | Location/Qualifiers | |
| source | 1..1271 | |
| | mol_type = other DNA | |
| | organism = synthetic construct | |

SEQUENCE: 11

```
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt ctttcaattt ttcgattttt ccatttgatt ttattgtttg   360
ggaattattt ttccttaatt cttccattc tatcaatgaa gaatctataa gaattctcaa   420
ttccatatca tttcatttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca tttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc  1020
```

```
ttttatttga cttcaaaata agttattgct tttataataa taatgatatg ataaaaaaaa   1080
aaactaatag ataaaaaaag tacttagaaa acattttttc aagaacgtta aaggtaaagt   1140
ttagatggag gcaattgtgt attttactgt aaccaaccaa ggccgagtac tatcagcgtg   1200
ttgcacattt tggttatctt tagcacagtg ttgaagataa cgaacgaata gtgccattac   1260
tgtaaccaac c                                                       1271

SEQ ID NO: 12           moltype = DNA   length = 1272
FEATURE                 Location/Qualifiers
source                  1..1272
                        mol_type = other DNA
                        organism = synthetic construct
SEQUENCE: 12
attaagaagc ttacaaagag attgggaact aaaactactt aaaaaaaaag gaattaaaat   60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttttcaattt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattca tctttataaa aaattactaa   840
aaatatttaa tgatacgtca tttttcaatt atgtttcttt cctttactaa actcgaatca   900
aatacaaaaa taaattgttt gagtgccgaa agtccgaaac ttattatttg acttcaaaat   960
aagttattgt tttatctta taatatcgt cctataaaaa aaattattct aaatattagc   1020
ttttatttga cttcaaaata agttattgct tttataataa taatgatatg ataaaaaaaa   1080
aaactaatag gataaaaaaa gtacttagaa aacatttttt caagaacgtt aaaggtaaag   1140
tttagatgga ggcaattgtg tattttactg taaccaacca aggccgagta ctatcagcgt   1200
gtcgcacatt tggttatctt ttagcacagt gttgaagata acgaacgaat agtgccatta   1260
ctgtaaccaa cc                                                      1272

SEQ ID NO: 13           moltype = DNA   length = 1272
FEATURE                 Location/Qualifiers
source                  1..1272
                        mol_type = other DNA
                        organism = synthetic construct
SEQUENCE: 13
attaagaagc ttacaaagag attgggaact aaaactactt aaaaaaaaag gaattaaaat   60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttttcaattt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattca tctttataaa aaattactaa   840
aaatatttaa tgatacgtca tttttcaatt atgtttcttt cctttactaa actcgaatca   900
aatacaaaaa taaattgttt gagtgccgaa agtccgaaac ttattatttg acttcaaaat   960
aagttattgt tttatctta taatatcgt cctataaaaa aaattattct aaatattagc   1020
ttttatttga cttcaaaata agttattgct tttataataa taatgatatg ataaaaaaaa   1080
aaactaatag gataaaaaaa gtacttagaa aacatttttt caagaacgtt aaaggtaaag   1140
tttagatgga ggcaattgtg tattttactg taaccaacca aggccgagta ctatcagcgt   1200
gttgcacatt tgggttatct tttagcacagt gttgaagata acgaacgaat agtgccatta   1260
ctgtaaccaa cc                                                      1272

SEQ ID NO: 14           moltype = DNA   length = 1272
FEATURE                 Location/Qualifiers
source                  1..1272
                        mol_type = other DNA
                        organism = synthetic construct
SEQUENCE: 14
attaagaagc ttacaaagag attgggaact aaaactactt aaaaaaaaag gaattaaaat   60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttttcaattt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
```

```
aattcaatag aacaaatttc ttatattgtt attagttcaa taaatatatt tatttacata      600
aaaaataata aaaggagatc tatcttaaat tcttgtatat gaaatttgat tctcgtgaat      660
gaaacaaaac ataaaaaaag atcatgagta acttgatgat gctattgcca ttattaatag      720
tttaataatt attccttaaa ataaatagtt caataactat atctacttac aaagaaaata      780
aaatgagcga cttatatttt ttattagctt taatgattaa tctttataaa aaattactaa      840
aaatatttaa tgatacgtca ttttttcaatt atgtttcttt cctttactaa actcgaatca     900
aatacaaaaa taaattgttt gagtgccgaa agtccgaaac ttattattg acttcaaaat       960
aagttattgt ttttatctta taataatcgt cctataaaaa aaattattct aaatattagc     1020
ttttatttga cttcaaaata agttattgct tttataataa taatgatatg ataaaaaaaa     1080
aaaactaata gataaaaaaa gtacttagaa aacattttt caagatcgtt aaaggtaaag      1140
tttagatgga ggcaattgtg tattttactg taaccaacca aggccgagta ctatcagcgt     1200
gttgcacatt ttggttatct ttagcacagt gttgaagata acgaacgaat agtgccatta     1260
ctgtaaccaa cc                                                         1272

SEQ ID NO: 15          moltype = DNA  length = 1272
FEATURE                Location/Qualifiers
source                 1..1272
                       mol_type = other DNA
                       organism = synthetic construct SEQUENCE: 15
attaagaagc ttacaaagag attgggaact aaaactactt aaacaaaaag gaattaaaat       60
caatttcaac caaattataa gagacttaag atacatttta ttctaggaaa caatattact      120
tctggactt taaacaagaa acaaaaaata aattaattaa gatcaattga atagttaatt      180
taattatttt taatcaataa tattataaat ttatatttta ttctaaaaat gtttatcaaa      240
ctaagtaaca tctggttta tatttgttca gagaaaatgc gtagctaact ctatgcatta       300
aacaaaaaaa agaaaatttt cttttcaatt ttcgatttt ccatttgatt ttattgtttg      360
ggaattattt ttccttaatt cttccattc tatcaatgaa gaatctataa gaattctcaa      420
ttccatatca tttcattttt aaaaatttaa tcgtaatgga aataagaaag actaatattc      480
ctttggaaat attacccgaa tgatatttct tctcttatag gtaataagta tattatttgt      540
aattcaatag aacaaatttc ttatattgtt attagttcaa taaatatatt tatttacata      600
aaaaataata aaaggagatc tatcttaaat tcttgtatat gaaatttgat tctcgtgaat      660
gaaacaaaac ataaaaaaag atcatgagta acttgatgat gctattgcca ttattaatag      720
tttaataatt attccttaaa ataaatagtt caataactat atctacttac aaagaaaata      780
aaatgagcga cttatatttt ttattagctt taatgattaa tctttataaa aaattactaa      840
aaatatttaa tgatacgtca ttttttcaatt atgtttcttt cctttactaa actcgaatca     900
aatacaaaaa taaattgttt gagtgccgaa agtccgaaac ttattattg acttcaaaat       960
aagttattgt ttttatctta taataatcgt cctataaaaa aaattattct aaatattagc     1020
ttttatttga cttcaaaata agttattgct tttataataa taatgatatg ataaaaaaaa     1080
aaaactaata gataaaaaaa gtacttagaa aacattttt caagatcgtt aaaggtaaag      1140
tttagatgga ggcaattgtg tattttactg taaccaacca aggccgagta ctatcagcgt     1200
gttgcacatt ttggttatct ttagcacagt gttgaagata acgaacgaat agtgccatta     1260
ctgtaaccaa cc                                                         1272

SEQ ID NO: 16          moltype = DNA  length = 1272
FEATURE                Location/Qualifiers
source                 1..1272
                       mol_type = other DNA
                       organism = synthetic construct SEQUENCE: 16
attaagaagc ttacaaagag attgggaact aaaactactt aaaaaaaaag gaattaaaat       60
caatttcaac caaattataa gagacttaag atacatttta ttctaggaaa caatattact      120
tctggactt taaacaagaa tcaaaaaata aattaattaa gatcaattga atagttaatt      180
taattatttt taatcaataa tattataaat ttatatttta ttctaaaaat gtttatcaaa      240
ctaagtaaca tctggttta tatttgttca gagaaaatgc gtagctaact ctatgcatta       300
aacaaaaaaa agaaaatttt cttttcaatt ttcgatttt ccatttgatt ttattgtttg      360
ggaattattt ttccttaatt cttccattc tatcaatgaa gaatctataa gaattctcaa      420
ttccatatca tttcattttt aaaaatttaa tcgtaatgga aataagaaag actaatattc      480
ctttggaaat attacccgaa tgatatttct tctcttatag gtaataagta tattatttgt      540
aattcaatag aacaaatttc ttatattgtt attagttcaa taaatatatt tatttacata      600
aaaaataata aaaggagatc tatcttaaat tcttgtatat gaaatttgat tctcgtgaat      660
gaaacaaaac ataaaaaaag atcatgagta acttgatgat gctattgcca ttattaatag      720
tttaataatt attccttaaa ataaatagtt caataactat atctacttac aaagaaaata      780
aaatgagcga cttatatttt ttattagctt taatgattaa tctttataaa aaattactaa      840
aaatatttaa tgatacgtca ttttttcaatt atgtttcttt cctttactaa actcgaatca     900
aatacaaaaa taaattgttt gagtgccgaa agtccgaaac ttattattg acttcaaaat       960
aagttattgt ttttatctta taataatcgt cctataaaaa aaattattct aaatattagc     1020
ttttatttga cttcaaaata agttattgct tttataataa taatgatatg ataaaaaaaa     1080
aaaactaata gataaaaaaa gtacttagaa aacattttt caagaacgtt aaaggtaaag      1140
tttagatgga ggcaattgtg tattttactg taaccaacca aggccgagta ctatcagcgt     1200
gttgcacatt ttggttatct ttagcacagt gttgaagata acgaacgaat agtgccatta     1260
ctgtaaccaa cc                                                         1272

SEQ ID NO: 17          moltype = DNA  length = 1272
FEATURE                Location/Qualifiers
source                 1..1272
                       mol_type = other DNA
                       organism = synthetic construct SEQUENCE: 17
attaagaagc ttacaaagag attgggaact aaaactactt aaaaaaaaag gaattaaaat       60
```

```
caatttcaac caaattataa gagacttaag atacatttta ttctaggaaa caatattact    120
tctggacttt taaacaagaa acaaaaaata aattaattaa gatcaattga atagttaatt    180
taattatttt taatcaataa tattataaat ttatattta ttctaaaaat gtttatcaaa     240
ctaagtaaca tctggtttta tatttgttca gagaaaatgc gtagctaact ctatgcatta    300
aacaaaaaaa agaaaatttt cttccaattt ttcgactttt ccatttgatt ttattgtttg    360
ggaattattt ttccttaatt cttttccattc tatcaatgaa gaatctataa gaattctcaa   420
ttccatatca tttcattttt aaaaattaa tcgtaatgga aataagaaag actaatattc     480
ctttggaaat attcccgaa tgatatttct tctcttatag gtaataagta tattatttgt     540
aattcaatag aacaaatttc ttatattgtt attagttcaa taaatatatt tatttacata    600
aaaaataata aaaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactat atctacttac aaagaaaata    780
aaatgagcga cttatatttt ttattagctt taatgattaa tctttataaa aaattactaa    840
aaatatttaa tgatacgtca ttttttcaatt atgtttcttt cctttactaa actcgaatca   900
aatacaaaaa taaattgttt gagtgccgaa agtccgaaac ttattattg acttcaaaat     960
aagttattgt ttttatctta taataatcgt cctataaaaa aaattattct aaatattagc   1020
ttttatttga cttcaaaata agttattgct tttaataa taatgatatg ataaaaaaa     1080
aaaactaata gataaaaaaa gtacttagaa aacatttttt caagaacgtt aaaggtaaag   1140
tttagatgga ggcaattgtg tatttttactg taaccaacca aggccgagta ctatcagcgt  1200
gttgcacatt ttggttatct ttagcacagt gttgaagata acgaacgaat agtgccatta   1260
ctgtaaccaa cc                                                       1272

SEQ ID NO: 18        moltype = DNA   length = 1272
FEATURE              Location/Qualifiers
source               1..1272
                     mol_type = other DNA
                     organism = synthetic construct
SEQUENCE: 18
attaagaagc ttacaaagag attgggaact aaaactactt aaaaaaaaag gaattaaaat     60
caatttcaac caaattataa gagacttaag atacatttta ttctaggaaa caatattact    120
tctggacttt taaacaagaa acaaaaaata aattaattaa gatcaattga atagttaatt    180
taattatttt taatcaataa tattataaat ttatattta ttctaaaaat gtttatcaaa    240
ctaagtaaca tctggtttta tatttgttca gagaaaatgc gtagctaact ctatgcatta    300
aacaaaaaaa agaaaatttt cttccaattt ttcgattttt ccatttgatt ttattgttag    360
ggaattattt ttccttaatt cttttccattc tatcaatgaa gaatctataa gaattctcaa   420
ttccatatca tttcattttt aaaaattaa tcgtaatgga aataagaaag actaatattc     480
ctttggaaat attcccgaa tgatatttct tctcttatag gtaataagta tattatttgt     540
aattcaatag aacaaatttc ttatattgtt attagttcaa taaatatatt tatttacata    600
aaaaataata aaaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactat atctacttac aaagaaaata    780
aaatgagcga cttatatttt ttattagctt taatgattaa tctttataaa aaattactaa    840
aaatatttaa tgatacgtca ttttttcaatt atgtttcttt cctttactaa actcgaatca   900
aatacaaaaa taaattgttt gagtgccgaa agtccgaaac ttattattg acttcaaaat     960
aagttattgt ttttatctta taataatcgt cctataaaaa aaattattct aaatattagc   1020
ttttatttga cttcaaaata agttattgct tttaataa taatgatatg ataaaaaaa     1080
aaaactaata gataaaaaaa gtacttagaa aacatttttt caagaacgtt aaaggtaaag   1140
tttagatgga ggcaattgtg tatttttactg taaccaacca aggccgagta ctatcagcgt  1200
gttgcacatt ttggttatct ttagcacagt gttgaagata acgaacgaat agtgccatta   1260
ctgtaaccaa cc                                                       1272

SEQ ID NO: 19        moltype = DNA   length = 1272
FEATURE              Location/Qualifiers
source               1..1272
                     mol_type = other DNA
                     organism = synthetic construct
SEQUENCE: 19
attaagaagc ttacaaagag attgggaact aaaactactt aaaaaaaaag gaattaaaat     60
caatttcaac caaattataa gagacttaag atacatttta ttctaggaaa caatattact    120
tctggacttt taaacaagaa acaaaaaata aattaattaa gatcaattga atagttaatt    180
taattatttt taatcaataa tattataaat ttatattta ttctaaaaat gtttatcaaa    240
ctaagtaaca tctggtttta tatttgttca gagaaaatgc gtagctaact ctatgcatta    300
aacaaaaaaa agaaaatttt cttccaattt ttcgattttt ccatttgatt ttattgtttg    360
ggaattattt ttccttaatt cttttccattc tatcaatgaa gaatctataa gaattctcaa   420
ttccatatca tttcattttt aaaaattaa tcgtaatgga aataagaaag actaatattc     480
ctttggaaat attcccgaa tgatatttct tctcttatag gtaataagta tattatttgt     540
aattcaatag aacaaatttc ttatattgtt attagttcaa taaatatatt tatttacata    600
aaaaataata aaaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ctaaatagtt caataactat atctacttac aaagaaaata    780
aaatgagcga cttatatttt ttattagctt taatgattaa tctttataaa aaattactaa    840
aaatatttaa tgatacgtca ttttttcaatt atgtttcttt cctttactaa actcgaatca   900
aatacaaaaa taaattgttt gagtgccgaa agtccgaaac ttattattg acttcaaaat     960
aagttattgt ttttatctta taataatcgt cctataaaaa aaattattct aaatattagc   1020
ttttatttga cttcaaaata agttattgct tttaataa taatgatatg ataaaaaaa     1080
aaaactaata gataaaaaaa gtacttagaa aacatttttt caagaacgtt aaaggtaaag   1140
tttagatgga ggcaattgtg tatttttactg taaccaacca aggccgagta ctatcagcgt  1200
gttgcacatt ttggttatct ttagcacagt gttgaagata acgaacgaat agtgccatta   1260
ctgtaaccaa cc                                                       1272
```

```
SEQ ID NO: 20           moltype = DNA  length = 1272
FEATURE                 Location/Qualifiers
source                  1..1272
                        mol_type = other DNA
                        organism = synthetic construct
SEQUENCE: 20
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttttcaattt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taaagattaa tctttataaa aaattactaa   840
aaatatttaa tgatacgtca tttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc  1020
ttttatttga cttcaaaata agtattgct tttataataa taatgatatg ataaaaaaaa  1080
aaaactaata gataaaaaaa gtacttagaa aacattttt caagaacgtt aaaggtaaag  1140
tttagatgga ggcaattgtg tattttactg taaccaacca aggccgagta ctatcagcgt  1200
gttgcacatt ttggttatct ttagcacagt gttgaagata acgaacgaat agtgccatta  1260
ctgtaaccaa cc                                                     1272

SEQ ID NO: 21           moltype = DNA  length = 1272
FEATURE                 Location/Qualifiers
source                  1..1272
                        mol_type = other DNA
                        organism = synthetic construct
SEQUENCE: 21
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttttcaattt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca tttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc  1020
ttttatttga cttcaaaata agtattgct tttataataa taatgatatg ataaaaaaaa  1080
aaaactaata gataaaaaaa gtacttagaa aacattttt caagaacgtt aaaggtaaag  1140
tttagatgga ggcaattgtg tattttactg taaccaacca aggccgagta ctatcagcgt  1200
gttgcacatt ttggttatct ttagcacagt gttgaagata acgaacgaat agtgccatta  1260
ctgtaaccaa cc                                                     1272

SEQ ID NO: 22           moltype = DNA  length = 1272
FEATURE                 Location/Qualifiers
source                  1..1272
                        mol_type = other DNA
                        organism = synthetic construct
SEQUENCE: 22
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttttcaattt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
```

```
aaatatttaa tgatacgtca tttttcaatt atgtttcttt cctttactaa actcgaatca    900
aatacaaaaa taaattgtat gagtgccgaa agtccgaaac ttattatttg acttcaaaat    960
aagttattgt ttttatctta taataatcgt cctataaaaa aaattattct aaatattagc   1020
ttttatttga cttcaaaata agttattgct tttataataa taatgatatg ataaaaaaaa   1080
aaaactaata gataaaaaaa gtacttagaa aacattttt caagaacgtt aaaggtaaag    1140
tttagatgga ggcaattgtg tattttactg taaccaacca aggccgagta ctatcagcgt   1200
gttgcacatt ttggttatct ttagcacagt gttgaagata acgaacgaat agtgccatta   1260
ctgtaaccaa cc                                                      1272

SEQ ID NO: 23          moltype = DNA   length = 1272
FEATURE                Location/Qualifiers
source                 1..1272
                       mol_type = other DNA
                       organism = synthetic construct
SEQUENCE: 23
attaagaagc ttacaaagag attgggaact aaaactactt aaaaaaaaag gaattaaaat     60
caatttcaac caaattataa gagacttaag atacatttta ttctaggaaa caatattact    120
tctggacttt taaacaagaa acaaaaaata aattaattaa gatcaattga atagttaatt    180
taattatttt taatcaataa tattataaat ttatatttta ttctaaaaat gtttatcaaa    240
ctaagtaaca tctggtttta tatttgttca gagaaaatgc gtagctaact ctatgcatta    300
aacaaaaaaa agaaaatttt cttcaatttt ttcgatttttt ccatttgatt ttattgtttg    360
ggaattattt ttccttaatt cttttccattc tatcaatgaa gaatctataa gaattctcaa    420
ttccatatca tttcattttt aaaatttaaa tcgtaatgga aataagaaag actaatattc    480
ctttggaaat attacccgaa tgatatttct tctcttatag gtaataagta tattattttgt    540
aattcaatag aacaaatttc ttatattgtt attagttcaa taaatatatt tatttacata    600
aaaaataata aaaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactat atctacttac aaagaaaata    780
aaatgagcga cttatatttt ttattagctt taatgattaa tctttataaa aaattactaa    840
aaatatttaa tgatacgtca tttttcaatt atgtttcttt cctttactaa actcgaatca    900
aatacaaaaa taaattgttt gggtgccgaa agtccgaaac ttattatttg acttcaaaat    960
aagttattgt ttttatctta taataatcgt cctataaaaa aaattattct aaatattagc   1020
ttttatttga cttcaaaata agttattgct tttataataa taatgatatg ataaaaaaaa   1080
aaaactaata gataaaaaaa gtacttagaa aacattttt caagaacgtt aaaggtaaag    1140
tttagatgga ggcaattgtg tattttactg taaccaacca aggccgagta ctatcagcgt   1200
gttgcacatt ttggttatct ttagcacagt gttgaagata acgaacgaat agtgccatta   1260
ctgtaaccaa cc                                                      1272

SEQ ID NO: 24          moltype = DNA   length = 1272
FEATURE                Location/Qualifiers
source                 1..1272
                       mol_type = other DNA
                       organism = synthetic construct
SEQUENCE: 24
attaagaagc ttacaaagag attgggaact aaaactactt aaaaaaaaag gaattaaaat     60
caatttcaac caaattataa gagacttaag atacatttta ttctaggaaa caatattact    120
tctggacttt taaacaagaa acaaaaaata aattaattaa gatcaattga atagttaatt    180
taattatttt taatcaataa tattataaat ttatatttta ttctaaaaat gtttatcaaa    240
ctaagtaaca tctggtttta tatttgttca gagaaaatgc gtagctaact ctatgcatta    300
aacaaaaaaa agaaaatttt cttcaatttt ttcgatttttt ccatttgatt ttattgtttg    360
ggaattattt ttccttaatt cttttccattc tatcaatgaa gaatctataa gaattctcaa    420
ttccatatca tttcattttt aaaatttaaa tcgtaatgga aataagaaag actaatattc    480
ctttggaaat attacccgaa tgatatttct tctcttatag gtaataagta tattattttgt    540
aattcaatag aacaaatttc ttatattgtt attagttcaa taaatatatt tatttacata    600
aaaaataata aaaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactat atctacttac aaagaaaata    780
aaatgagcga cttatatttt ttattagctt taatgattaa tctttataaa aaattactaa    840
aaatatttaa tgatacgtca tttttcaatt atgtttcttt cctttactaa actcgaatca    900
aatacaaaaa taaattgttt gagtgccgaa agtccgaaac ttattatttg acttcaaaat    960
aagttattgt ttttatctta taataatcgt cctataaaaa aaattattct aaatattggc   1020
ttttatttga cttcaaaata agttattgct tttataataa taatgatatg ataaaaaaaa   1080
aaaactaata gataaaaaaa gtacttagaa aacattttt caagaacgtt aaaggtaaag    1140
tttagatgga ggcaattgtg tattttactg taaccaacca aggccgagta ctatcagcgt   1200
gttgcacatt ttggttatct ttagcacagt gttgaagata acgaacgaat agtgccatta   1260
ctgtaaccaa cc                                                      1272

SEQ ID NO: 25          moltype = DNA   length = 1272
FEATURE                Location/Qualifiers
source                 1..1272
                       mol_type = other DNA
                       organism = synthetic construct
SEQUENCE: 25
attaagaagc ttacaaagag attgggaact aaaactactt aaaaaaaaag gaattaaaat     60
caatttcaac caaattataa gagacttaag atacatttta ttctaggaaa caatattact    120
tctggacttt taaacaagaa acaaaaaata aattaattaa gatcaattga atagttaatt    180
taattatttt taatcaataa tattataaat ttatatttta ttctaaaaat gtttatcaaa    240
ctaagtaaca tctggtttta tatttgttca gagaaaatgc gtagctaact ctatgcatta    300
aacaaaaaaa agaaaatttt cttcaatttt ttcgatttttt ccatttgatt ttattgtttg    360
```

```
ggaattattt ttccttaatt ctttccattc tatcaatgaa gaatctataa gaattctcaa  420
ttccatatca tttcattttt aaaaatttaa tcgtaatgga aataagaaag actaatattc  480
ctttggaaat attacccgaa tgatatttct tctcttatag gtaataagta tattatttgt  540
aattcaatag aacaaatttc ttatattgtt attagttcaa taaatatatt tatttacata  600
aaaaataata aaaggagatc tatcttaaat tcttgtatat gaaatttgat tctcgtgaat  660
gaaacaaaac ataaaaaaag atcatgagta acttgatgat gctattgcca ttattaatag  720
tttaataatt attccttaaa ataaatagtt caataactat atctacttac aaagaaaata  780
aaatgagcga cttatatttt ttattagctt taatgattaa tctttataaa aaattactaa  840
aaatatttaa tgatacgtca ttttcaatt atgtttcttt cctttactaa actcgaatca   900
aatacaaaaa taaattgttt gagtgccgaa agtccgaaac ttattatttg acttcaaaat  960
aagttattgt ttttatctta taatatcgt cctataaaaa aaattattct aaatattagc  1020
ttttatttga cttcaaaata agttattgct tttataataa taatgatatg ataaaaaaaa  1080
aaaactaata gataaaaaaa gtacttagaa aacattttt caagaacgtt aaaggtaaag  1140
tttagatgga ggcagttgtg tattttactg taaccaacca aggccgagta ctatcagcgt  1200
gttgcacatt ttggttatct ttagcacagt gttgaagata acgaacgaat agtgccatta  1260
ctgtaaccaa cc                                                      1272

SEQ ID NO: 26          moltype = DNA   length = 1272
FEATURE                Location/Qualifiers
source                 1..1272
                       mol_type = other DNA
                       organism = synthetic construct
SEQUENCE: 26
attaagaagc ttacaaagag attgggaact aaaactactt aaaaaaaaag gaattaaaat  60
caatttcaac caaattataa gagacttaag atacatttta ttctaggaaa caatattact  120
tctggactt taaacaagaa tcaaaaaata aattaattaa gatcaattga atagttaatt  180
taattatttt taatcaataa tattataaat ttatattta ttctaaaaat gtttatcaaa   240
ctaagtaaca tctggtttta tatttgttca gagaaaatgc gtagctaact ctatgcatta  300
aacaaaaaaa agaaaatttt ctttcaattt ttcgactttt ccatttgatt ttattgttag  360
ggaattattt ttccttaatt ctttccattc tatcaatgaa gaatctataa gaattctcaa  420
ttccatatca tttcattttt aaaaatttaa tcgtaatgga aataagaaag actaatattc  480
ctttggaaat attacccgaa tgatatttct tctcttatag gtaataagta tattatttgt  540
aattcaatag aacaaatttc ttatattgtt attagttcaa taaatatatt tatttacata  600
aaaaataata aaaggagatc tatcttaaat tcttgtatat gaaatttgat tctcgtgaat  660
gaaacaaaac ataaaaaaag atcatgagta acttgatgat gctattgcca ttattaatag  720
tttaataatt attccttaaa ctaaatagtt caataactat atctacttac aaagaaaata  780
aaatgagcga cttatatttt ttattagctt taaagattaa tctttataaa aaattactaa  840
aaatatttaa tgatacgtca ttttcaatt atgtttcttt cctttactag actcgaatca   900
aatacaaaaa taaattgtat gggtgccgaa agtccgaaac ttattatttg acttcaaaat  960
aagttattgt ttttatctta taatatcgt cctataaaaa aaattattct aaatattggc   1020
ttttatttga cttcaaaata agttattgct tttataataa taatgatatg ataaaaaaaa  1080
aaaactaata gataaaaaaa gtacttagaa aacattttt caagaacgtt aaaggtaaag  1140
tttagatgga ggcagttgtg tattttactg taaccaacca aggccgagta ctatcagcgt  1200
gtcgcacatt tgggttatct ttagcacagt gttgaagata acgaacgaat agtgccatta  1260
ctgtaaccaa cc                                                      1272

SEQ ID NO: 27          moltype = DNA   length = 1273
FEATURE                Location/Qualifiers
source                 1..1273
                       mol_type = other DNA
                       organism = synthetic construct
SEQUENCE: 27
attaagaagc ttacaaagag attgggaact aaaactactt aaaaaaaaag gaattaaaat  60
caatttcaac caaattataa gagacttaag atacatttta ttctaggaaa caatattact  120
tctggacttt taaacaagaa acaaaaaata aattaattaa gatcaatcga atagttaatt  180
taattatttt taatcaataa tattataaat ttatattta ttctaaaaat gtttatcaaa   240
ctaagtaaca tctggtttta tatttgttca gagaaaatgc gtagctaact ctatgcatta  300
aacaaaaaaa agaaaatttt ctttcaattt ttcgattttt ccatttgatt ttattgtttg  360
ggaattattt ttccttaatt ctttccattc tatcaatgaa gaatctataa gaattctcaa  420
ttccatatca tttcattttt aaaaatttaa tcgtaatgga aataagaaag actaatattc  480
ctttggaaat attacccgaa tgatatttct tctcttatag gtaataagta tattatttgt  540
aattcaatag aacaaatttc ttatattgtt attagttcaa taaatatatt tatttacata  600
aaaaataata aaaggagatc tatcttaaat tcttgtatat gaaatttgat tctcgtgaat  660
gaaacaaaac ataaaaaaag atcatgagta acttgatgat gctattgcca ttattaatag  720
tttaataatt attccttaaa ataaatagtt caataactat atctacttac aaagaaaata  780
aaatgagcga cttatatttt ttattagctt taatgattaa tctttataaa aaattactaa  840
aaatatttaa tgatacgtca ttttcaatt atgtttcttt cctttactaa actcgaatca   900
aatacaaaaa taaattgttt gagtgccgaa agtccgaaac ttattatttg acttcaaaat  960
aagttattgt ttttatctta taatatcgt cctataaaaa aaattattct aaatattagc   1020
ttttatttga cttcaaaata agttattgct tttataataa taatgatatg ataaaaaaaa  1080
aaaactaat agataaaaaa agtacttaga aaacattttt tcaagaacgt taaaggtaaa  1140
gtttagatgg aggcaattgt gtattttact gtaaccaacc aaggccgagt actatcagcg  1200
tgttgcacat tttggttatc tttagcacag tgttgaagat aacgaacgaa tagtgccatt  1260
actgtaaccaa acc                                                    1273

SEQ ID NO: 28          moltype = DNA   length = 1272
FEATURE                Location/Qualifiers
source                 1..1272
                       mol_type = other DNA
```

```
                        organism = synthetic construct
SEQUENCE: 28
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattgattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt ctttcaattt ttcgattttt ccatttgatt ttattgtttg   360
ggaattattt ttccttaatt cttttccatt c tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca ttttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc  1020
ttttatttga cttcaaaata agttattgct tttataataa taatgatatg ataaaaaaaa  1080
aaaactaata gataaaaaaa gtacttagaa aacatttttt caagaacgtt aaaggtaaag  1140
tttagatgga ggcaattgtg tatttactg taaccaacca aggccgagta ctatcagcgt  1200
tgttgcacat ttggttatct ttagcacagt gttgaagata acgaacgaat agtgccatta  1260
ctgtaaccaa cc                                                     1272

SEQ ID NO: 29          moltype = DNA  length = 1272
FEATURE                Location/Qualifiers
source                 1..1272
                       mol_type = other DNA
                       organism = synthetic construct
SEQUENCE: 29
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt ctttcaattt ttcgattttt ccatttgatt ttattgtttg   360
ggaattattt ttccttaatt cttttccatt c tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca ttttttcaatt atgtttcttt cctttactaa actcgaatct   900
aatacaaaaa taaattgttt gagtgccgaa agtccgaaac ttattatttg acttcaaaat   960
aagttattgt ttttatctta taataatcgt cctataaaaa aaattattct aaatattagc  1020
ttttatttga cttcaaaata agttattgct tttataataa taatgatatg ataaaaaaaa  1080
aaaactaata gataaaaaaa gtacttagaa aacatttttt caagaacgtt aaaggtaaag  1140
tttagatgga ggcaattgtg tatttactg taaccaacca aggccgagta ctatcagcgt  1200
gttgcacatt tggttatct ttagcacagt gttgaagata acgaacgaat agtgccatta  1260
ctgtaaccaa cc                                                     1272

SEQ ID NO: 30          moltype = DNA  length = 1272
FEATURE                Location/Qualifiers
source                 1..1272
                       mol_type = other DNA
                       organism = synthetic construct
SEQUENCE: 30
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt ctttcaattt ttcgattttt ccatttgatt ttattgtttg   360
ggaattattt ttccttaatt cttttccatt c tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca ttttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataataa aaattattct aaatattagc  1020
ttttatttga cttcaaaata agttattgct tttataataa taatgatatg ataaaaaaaa  1080
aaaactaata gataaaaaaa gtacttagaa aacatttttt caagaacgtt aaaggtaaag  1140
```

```
tttagatgga ggcaattgtg tattttactg taaccaacca aggccgagta ctatcagcgt  1200
gttgcacatt ttggttatct ttagcacagt gttgaagata acgaacgaat agtgccatta  1260
ctgtaaccaa cc                                                      1272

SEQ ID NO: 31           moltype = DNA   length = 1272
FEATURE                 Location/Qualifiers
source                  1..1272
                        mol_type = other DNA
                        organism = synthetic construct
SEQUENCE: 31
attaagaagc ttacaaagag attgggaact aaaactactt aaaaaaaaag gaattaaaat   60
caatttcaac caaattataa gagacttaag atacatttta ttctaggaaa caatattact  120
tctggacttt taaacaagaa acaaaaaata aattaattaa gatcaattga atagttaatt  180
taattatttt taatcaataa tattataaat ttatatttta ttctaaaaat gtttatcaaa  240
ctaagtaaca tctggtttta tatttgttca gagaaaatgc gtagctaact ctatgcatta  300
aacaaaaaaa agaaaatttt cttcaatt ttcgattttt ccatttgatt ttattgtttg    360
ggaattattt ttccttaatt ctttccattc tatcaatgaa gaatctataa gaattctcaa  420
ttccatatca tttcattttt aaaaatttaa tcgtaatgga aataagaaag actaatattc  480
ctttggaaat attcccgaa tgatatttct tctcttatag gtaataagta tattatttgt   540
aattcaatag aacaaatttc ttatattgtt attagttcaa taaatatatt tatttacata  600
aaaaataata aaaggagatc tatcttaaat tcttgtatat gaaatttgat tctcgtgaat  660
gaaacaaaac ataaaaaaag atcatgagta acttgatgat gctattgcca ttattaatag  720
tttaataatt attccttaaa ataaatagtt caataactat atctacttac aaagaaaata  780
aaatgagcga cttatatttt ttattagctt taatgattaa tctttataaa aaattactaa  840
aaatatttaa tgatacgtca tttttcaatt atgtttctt cctttactaa actcgaatca   900
aatacaaaaa taaattgttt gagtgccgaa agtccgaaac ttattattg acttcaaaat   960
aagttattgt ttttatctta taataatcgt cctataaaaa aaattattct aaatattagc 1020
ttttatttga cttcaaaata agttattgct ttttaataa taatgatatg ataaaaaaaa  1080
aaaactaata gataaaaaaa gtacttagaa aacattttt caagaacgtt aaaggtaaag  1140
tttagatgga ggcaattgtg tattttactg taaccaacca aggccgagta ctatcagcgt 1200
gttgcacatt ttggttatct ttagcacagt gttgaagata acgaacgaat agtgccatta 1260
ctgtaaccaa cc                                                     1272

SEQ ID NO: 32           moltype = DNA   length = 1272
FEATURE                 Location/Qualifiers
source                  1..1272
                        mol_type = other DNA
                        organism = synthetic construct
SEQUENCE: 32
attaagaagc ttacaaagag attgggaact aaaactactt aaaaaaaaag gaattaaaat   60
caatttcaac caaattataa gagacttaag atacatttta ttctaggaaa caatattact  120
tctggacttt taaacaagaa acaaaaaata aattaattaa gatcaattga atagttaatt  180
taattatttt taatcaataa tattataaat ttatatttta ttctaaaaat gtttatcaaa  240
ctaagtaaca tctggtttta tatttgttca gagaaaatgc gtagctaact ctatgcatta  300
aacaaaaaaa agaaaatttt cttcaatt ttcgattttt ccatttgatt ttattgtttg    360
ggaattattt ttccttaatt ctttccattc tatcaatgaa gaatctataa gaattctcaa  420
ttccatatca tttcattttt aaaaatttaa tcgtaatgga aataagaaag actaatattc  480
ctttggaaat attcccgaa tgatatttct tctcttatag gtaataagta tattatttgt   540
aattcaatag aacaaatttc ttatattgtt attagttcaa taaatatatt tatttacata  600
aaaaataata aaaggagatc tatcttaaat tcttgtatat gaaatttgat tctcgtgaat  660
gaaacaaaac ataaaaaaag atcatgagta acttgatgat gctattgcca ttattaatag  720
tttaataatt attccttaaa ataaatagtt caataactat atctacttac aaagaaaata  780
aaatgagcga cttatatttt ttattagctt taatgattaa tctttataaa aaattactaa  840
aaatatttaa tgatacgtca tttttcaatt atgtttctt cctttactaa actcgaatca   900
aatacaaaaa taaattgttt gagtgccgaa agtccgaaac ttattattg acttcaaaat   960
aagttattgt ttttatctta taataatcgt cctataaaaa aaattattct aaatattagc 1020
ttttatttga cttcaaaata agttattgct ttttaataa taatgatatg ataaaaaaaa  1080
aaaactaata gataaaaaaa gtacttagaa aacattttt caagaacgtt aaaggtaaag  1140
tttagatgga ggcaattgtg tattttactg taaccaacca aggccgagta ctatcagcgt 1200
gttgcgcatt ttggttatct ttagcacagt gttgaagata acgaacgaat agtgccatta 1260
ctgtaaccaa cc                                                     1272

SEQ ID NO: 33           moltype = DNA   length = 1271
FEATURE                 Location/Qualifiers
source                  1..1271
                        mol_type = other DNA
                        organism = synthetic construct
SEQUENCE: 33
attaagaagc ttacaaagag attgggaact aaaactactt aaaaaaaaag gaattaaaat   60
caatttcaac caaattataa gagacttaag atacatttta ttctaggaaa caatattact  120
tctggacttt taaacaagaa acaaaaaata aattgattaa gatcaattga atagttaatt  180
taattatttt taatcaataa tattataaat ttatatttta ttctaaaaat gtttatcaaa  240
ctaagtaaca tctggtttta tatttgttca gagaaaatgc gtagctaact ctatgcatta  300
aacaaaaaaa agaaaatttt cttcaatt ttcgattttt ccatttgatt ttattgtttg    360
ggaattattt ttccttaatt ctttccattc tatcaatgaa gaatctataa gaattctcaa  420
ttccatatca tttcattttt aaaaatttaa tcgtaatgga aataagaaag actaatattc  480
ctttggaaat attcccgaa tgatatttct tctcttatag gtaataagta tattatttgt   540
aattcaatag aacaaatttc ttatattgtt attagttcaa taaatatatt tatttacata  600
aaaataataa aaggagatct atcttaaatt cttgtatatg aaatttgatt ctcgtgaatg  660
```

```
aaacaaaaca taaaaaaaga tcatgagtaa cttgatgatg ctattgccat tattaatagt    720
ttaataatta ttccttaaaa taaatagttc aataactata tctacttaca aagaaaataa    780
aatgagcgac ttatattttt tattagcttt aatgattaat ctttataaaa aattactaaa    840
aatatttaat gatacgtcat ttttcaatta tgtttctttc ctttactaaa ctcgaatcta    900
atacaaaaat aaattgtttg agtgccgaaa gtccgaaact tattatttga cttcaaaata    960
agttattgtt tttatcttat aataatcgtc ctataataaa aattattcta aatattagct   1020
tttatttgac ttcaaaataa gttattgctt tttaataat aatgatatga taaaaaaaa    1080
aacctaatag ataaaaaaag tacttagaaa acattttttc aagaacgtta aaggtaaagt   1140
ttagatggag gcaattgtgt attttactgt aaccaaccag gccgagtac tatcagcgtg    1200
ttgcgcattt tggttatctt tagcacagtg ttgaagataa cgaacgaata gtgccattac   1260
tgtaaccaac c                                                        1271

SEQ ID NO: 34           moltype = DNA   length = 1272
FEATURE                 Location/Qualifiers
source                  1..1272
                        mol_type = other DNA
                        organism = synthetic construct
SEQUENCE: 34
attaagaagc ttacaaagag attgggaact aaaactactt aaaaaaaaag gaattaaaat     60
caatttcaac caaattataa gagacttaag atacatttta ttctaggaaa caatattact    120
tctggacttt taaacaagaa acaaaaaata aattaattaa gatcaattga gtagttaatt    180
taattatttt taatcaataa tattataaat ttatatttta ttctaaaaat gtttatcaaa    240
ctaagtaaca tctggtttta tatttgttca gagaaaatgc gtagctaact ctatgcatta    300
aacaaaaaaa agaaaatttt cttttcaattt ttcgattttt ccatttgatt ttattgtttg    360
ggaattattt ttccttaatt ctttccattc tatcaatgaa gaatctataa gaattctcaa    420
ttccatatca tttcattttt aaaaattaa tcgtaatgga aataagaaag actaatattc     480
ctttggaaat attcccgaa tgatatttct tctcttatag gtaataagta tattatttgt     540
aattcaatag aacaaattc ttatattgtt attagttcaa taaatatat tatttacata     600
aaaaataata aaaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactaa atctacttac aaagaaaata    780
aaatgagcga cttatatttt ttattagctt taatgattaa tctttataaa aaattactaa    840
aaatatttaa tgatacgtca ttttttcaatt atgtttcttt cctttactaa actcgaatca    900
aatacaaaaa taaattgttt gagtgccgaa agtccgaaac ttattatttg acttcaaaat    960
aagttattgt tttatctta taataatcgt cctataaaaa aattattct aaatattagc    1020
ttttatttga cttcaaaata gttattgct tttaataa taatgatatg ataaaaaaa    1080
aaaactaata gataaaaaaa gtacttagaa acattttttt caagaacgtt aaaggtaaag   1140
tttagatgga ggcaattgtg tattttactg taaccaacca aggccgagta ctatcagcgt   1200
gttgcacatt ttggttatct ttagcacagt gttgaagata acgaacgaat agtgccatta   1260
ctgtaaccaa cc                                                       1272

SEQ ID NO: 35           moltype = DNA   length = 1272
FEATURE                 Location/Qualifiers
source                  1..1272
                        mol_type = other DNA
                        organism = synthetic construct
SEQUENCE: 35
attaagaagc ttacaaagag attgggaact aaaactactt aaaaaaaaag gaattaaaat     60
caatttcaac caaattataa gagacttaag atacatttta ttctaggaaa caatattact    120
tctggacttt taaacaagaa acaaaaaata aattaattaa gatcaattga atagttaatt    180
taattatttt taatcaataa tattataaat ttatatttta ttctaaaaat gtttatcaaa    240
ctaagtaaca tctggtttta tatttgttca gagaaaatgc gtagctaact ctatgcatta    300
aacaaaaaaa agaaaatttt cttttcaattt ttcgattttt ccatttgatt ttattgtttg    360
ggaattattt ttccttaatt ctttccattc tatcaatgaa gaatctataa gaattctcaa    420
ttccatatca tttcattttt aaaaattaa tcgtaatgga aataagaaag actaatattc     480
ctttggaaat attcccgaa tgatatttct tctcttatag gtaataagta tattatttgt     540
aattcaatag aacaaattc ttatattgtt attagttcaa taaatatat tatttacata     600
aaaaataata aaaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactaa atctacttac aaagaaaata    780
aaatgagcga cttatatttt ttattagctt taatgattaa tctttataaa aaattactaa    840
aaatatttaa tgatacgtca ttttttcaatt atgtttcttt cctttactaa actcgaatca    900
aatacaaaaa taaattgttt gagtgccgaa agtccgaaac ttattatttg acttcaaaat    960
aagttattgt tttatctta taataatcgt cctataaaaa aattattct aaatattagc    1020
ttttatttga cttcaaaata gttattgct tttaataa taatgatatg ataaaaaaa    1080
aaaactaata gataaaaaaa gtacttagaa acattttttt caagaacgtt aaaggtaaag   1140
tttagatgga ggcaattgtg tattttactg taaccaacca aggccgagta ctatcagcgt   1200
gttgcacatt ttggttatct ttagcacagt gttgaagata acgaacgaat agtgccatta   1260
ctgtaaccaa cc                                                       1272

SEQ ID NO: 36           moltype = DNA   length = 1272
FEATURE                 Location/Qualifiers
source                  1..1272
                        mol_type = other DNA
                        organism = synthetic construct
SEQUENCE: 36
attaagaagc ttacaaagag attgggaact aaaactactt aaaaaaaaag gaattaaaat     60
caatttcaac caaattataa gagacttaag atacatttta ttctaggaaa caatattact    120
tctggacttt taaacaagaa acaaaaaata aattaattaa gatcaattga gtagttaatt    180
```

```
taattatttt taatcaataa tattataaat ttatatttta ttctaaaaat gtttatcaaa    240
ctaagtaaca tctggtttta tatttgttca gagaaaatgc gtagctaact ctatgcatta    300
aacaaaaaaa agaaaatttt ctttcaattt ttcgattttt ccatttgatt ttattgtttg    360
ggaattattt ttccttaatt ctttccattc tatcaatgaa gaatctataa gaattctcaa    420
ttccatatca tttcattttt aaaaatttaa tcgtaatgga aataagaaag actaatattc    480
ctttggaaat attcccgaa tgatatttct tctcttatag gtaataagta tattatttgt    540
aattcaatag aacaaatttc ttatattgtt attagttcaa taaatatatt tatttacata    600
aaaagtaata aaggagatc tatcttaaat tcttgtatat gaaatttgat tctcgtgaat    660
gaaacaaaac ataaaaaaag atcatgagta acttgatgat gctattgcca ttattaaatag   720
tttaataatt attccttaaa ataaatagtt caataactat atctacttac aaagaaaata    780
aaatgagcga cttatatttt ttattagctt taatgattaa tctttataaa aaattactaa    840
aaatatttaa tgatacgtca ttttttcaatt atgtttcttt cctttactaa actcgaatca    900
aatacaaaaa taaattgttt gagtgccgaa agtccgaaac ttattatttg acttcaaaat    960
aagttattgt ttttatctta taatatcgt cctataaaaa aaattattct aaatattagc   1020
ttttatttga cttcaaaata agttattgct tttataataa taatgatatg ataaaaaaaa   1080
aaaactaata gataaaaaaa gtacttagaa aacatttttt caagaacgtt aaaggtaaag   1140
tttagatgga ggcaattgtg tatttactg taaccaacca aggccgagta ctatcagcgt   1200
gttgcacatt ttggttatct ttagcacagt gttgaagata acgaacgaat agtgccatta   1260
ctgtaaccaa cc                                                      1272

SEQ ID NO: 37         moltype = DNA  length = 1272
FEATURE               Location/Qualifiers
source                1..1272
                      mol_type = other DNA
                      organism = synthetic construct
SEQUENCE: 37
attaagaagc ttacaaagag attgggaact aaaactactt aaaaaaaaag gaattaaaat     60
caatttcaac caaattataa gagacttaag atacatttta ttctaggaaa caatattact    120
tctggacttt taaacaagaa acaaaaaata aattaattaa gatcaattga atagttaatt    180
taattatttt tattcaataa tattataaat ttatatttta ttctaaaaat gtttatcaaa    240
ctaagtaaca tctggtttta tatttgttca gagaaaatgc gtagctaact ctatgcatta    300
aacaaaaaaa agaaaatttt ctttcaattt ttcgattttt ccatttgatt ttattgtttg    360
ggaattattt ttccttaatt ctttccattc tatcaatgaa gaatctataa gaattctcaa    420
ttccatatca tttcattttt aaaaatttaa tcgtaatgga aataagaaag actaatattc    480
ctttggaaat attcccgaa tgatatttct tctcttatag gtaataagta tattatttgt    540
aattcaatag aacaaatttc ttatattgtt attagttcaa taaatatatt tatttacata    600
aaaaataata aaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactat atctacttac aaagaaaata    780
aaatgagcga cttatatttt ttattagctt taatgattaa tctttataaa aaattactaa    840
aaatatttaa tgatacgtca ttttttcaatt atgtttcttt cctttactaa actcgaatca    900
aatacaaaaa taaattgttt gagtgccgaa agtccgaaac ttattatttg acttcaaaat    960
aagttattgt ttttatctta taatatcgt cctataaaaa aaattattct aaatattagc   1020
ttttatttga cttcaaaata agttattgct tttataataa taatgatatg ataaaaaaaa   1080
aaaactaata gataaaaaaa gtacttagaa aacatttttt caagaacgtt aaaggtaaag   1140
tttagatgga ggcaattgtg tatttactg taaccaacca aggccgagta ctatcagcgt   1200
gttgcacatt ttggttatct ttagcacagt gttgaagata acgaacgaat agtgccatta   1260
ctgtaaccaa cc                                                      1272

SEQ ID NO: 38         moltype = DNA  length = 1272
FEATURE               Location/Qualifiers
source                1..1272
                      mol_type = other DNA
                      organism = synthetic construct
SEQUENCE: 38
attaagaagc ttacaaagag attgggaact aaaactactt aaaaaaaaag gaattaaaat     60
caatttcaac caaattataa gagacttaag atacatttta ttctaggaaa caatattact    120
tctggacttt taaacaagaa acaaaaaata aattaattaa gatcaattga atagttaatt    180
taattatttt taatcaataa tattataaat ttatatttta ctctaaaaat gtttatcaaa    240
ctaagtaaca tctggtttta tatttgttca gagaaaatgc gtagctaact ctatgcatta    300
aacaaaaaaa agaaaatttt ctttcaattt ttcgattttt ccatttgatt ttattgtttg    360
ggaattattt ttccttaatt ctttccattc tatcaatgaa gaatctataa gaattctcaa    420
ttccatatca tttcattttt aaaaatttaa tcgtaatgga aataagaaag actaatattc    480
ctttggaaat attcccgaa tgatatttct tctcttatag gtaataagta tattatttgt    540
aattcaatag aacaaatttc ttatattgtt attagttcaa taaatatatt tatttacata    600
aaaaataata aaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactat atctacttac aaagaaaata    780
aaatgagcga cttatatttt ttattagctt taatgattaa tctttataaa aaattactaa    840
aaatatttaa tgatacgtca ttttttcaatt atgtttcttt cctttactaa actcgaatca    900
aatacaaaaa taaattgttt gagtgccgaa agtccgaaac ttattatttg acttcaaaat    960
aagttattgt ttttatctta taatatcgt cctataaaaa aaattattct aaatattagc   1020
ttttatttga cttcaaaata agttattgct tttataataa taatgatatg ataaaaaaaa   1080
aaaactaata gataaaaaaa gtacttagaa aacatttttt caagaacgtt aaaggtaaag   1140
tttagatgga ggcaattgtg tatttactg taaccaacca aggccgagta ctatcagcgt   1200
gttgcacatt ttggttatct ttagcacagt gttgaagata acgaacgaat agtgccatta   1260
ctgtaaccaa cc                                                      1272

SEQ ID NO: 39         moltype = DNA  length = 1272
```

| FEATURE | Location/Qualifiers |
|---|---|
| source | 1..1272 |
| | mol_type = other DNA |
| | organism = synthetic construct |

SEQUENCE: 39

```
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt ctttcaattt ttcgattttt ccatttgatt ttattgtttg   360
ggaattattt ttccttaatt ctttccattc tatcaatgaa gaatctataa gaattctcaa   420
ttccatatca tttcatttt aaaaatttaa tcgtaatgga aataagaaag actaatattc   480
ctttggaaat attacccgaa tgatatttct tctcttatag taataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac acaaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca tttttcaatt atgtttctt cctttactaa actcgaatca   900
aatacaaaaa taaattgttt gagtgccgaa agtccgaaac ttattatttg acttcaaaat   960
aagttattgt ttttatctta taatatcgt cctataaaaa aaattattct aaatattgc   1020
ttttatttga cttcaaaata agttattgct tttataataa taatgatatg ataaaaaaaa  1080
aaaactaata gataaaaaaa gtacttagaa aacattttt caagaacgtt aaaggtaaag  1140
tttagatgga ggcaattgtg tattttactg taaccaacca aggccgagta ctatcagcgt  1200
gttgcacatt ttggttatct ttagcacagt gttgaagata acgaacgaat agtgccatta  1260
ctgtaaccaa cc                                                      1272
```

| SEQ ID NO: 40 | moltype = DNA length = 1272 |
|---|---|
| FEATURE | Location/Qualifiers |
| source | 1..1272 |
| | mol_type = other DNA |
| | organism = synthetic construct |

SEQUENCE: 40

```
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt ctttcaattt ttcgattttt ccatttgatt ttattgtttg   360
ggaattattt ttccttaatt ctttccattc tatcaatgaa gaatctataa gaattctcaa   420
ttccatatca tttcatttt aaaaatttaa tcgtaatgga aataagaaag actaatattc   480
ctttggaaat attacccgaa tgatatttct tctcttatag taataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca tttttcaatt atgtttctt cctttactaa actcgaatca   900
aatacaaaaa taaattgttt gagtgccgaa agtccgaaac ttattatttg acttcaaaat   960
aagttattgt ttttatctta taatatcgt cctataaaaa aaattattct aaatattgc   1020
ttttatttga cttcaaaata agttattgct tttataataa taatgatatg ataaaaaaaa  1080
aaaactaata gataaaaaaa gtacttagaa aacattttt caagaacgtt aaaggtaaag  1140
tttagatgga ggcaattgtg tattttactg taaccaacca aggccgagta ctatcagcgt  1200
gttgcacatt ttggttatct ttagcacagt gttgaagata acgaacgaat agtgccatta  1260
ctgtaaccaa cc                                                      1272
```

| SEQ ID NO: 41 | moltype = DNA length = 1272 |
|---|---|
| FEATURE | Location/Qualifiers |
| source | 1..1272 |
| | mol_type = other DNA |
| | organism = synthetic construct |

SEQUENCE: 41

```
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt ctttcaattt ttcgattttt ccatttgatt ttattgtttg   360
ggaattattt ttccttaatt ctttccattc tatcaatgaa gaatctataa gaattctcaa   420
ttccatatca tttcatttt aaaaatttaa tcgtaatgga aataagaaag actaatattc   480
ctttggaaat attacccgaa tgatatttct tctcttatag taataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca tttttcaatt atgtttctt cctttactaa actcgaatca   900
aatacaaaaa taaattgttt gagtgccgaa agtccgaaac ttattatttg acttcaaaat   960
```

```
aagttattgt ttttatctta taataatcgt cctataaaaa aaattattct aaatattagc   1020
ctttatttga cttcaaaata agttattgct tttataataa taatgatatg ataaaaaaaa   1080
aaaactaata gataaaaaaa gtacttagaa aacatttttt caagaacgtt aaaggtaaag   1140
tttagatgga ggcaattgtg tattttactg taaccaacca aggccgagta ctatcagcgt   1200
gttgcacatt ttggttatct ttagcacagt gttgaagata acgaacgaat agtgccatta   1260
ctgtaaccaa cc                                                      1272

SEQ ID NO: 42          moltype = DNA  length = 1272
FEATURE                Location/Qualifiers
source                 1..1272
                       mol_type = other DNA
                       organism = synthetic construct
SEQUENCE: 42
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttcaatttt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttgaaat attacccgaa tgatatttct tctcttatag gtaataagta tattatttgt    540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactac atctacttac aaagaaaata   780
aaatgagcga cttatatttt ttattagctt taatgattaa tctttataaa aaattactaa   840
aaatatttaa tgatacgtca tttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc  1020
ttttatttga cttcaaaatg agttattgct tttataataa taatgatatg ataaaaaaaa  1080
aaaactaata gataaaaaaa gtacttagaa aacatttttt caagaacgtt aaaggtaaag  1140
tttagatgga ggcaattgtg tattttactg taaccaacca aggccgagta ctatcagcgt  1200
gttgcacatt ttggttatct ttagcacagt gttgaagata acgaacgaat agtgccatta  1260
ctgtaaccaa cc                                                     1272

SEQ ID NO: 43          moltype = DNA  length = 1272
FEATURE                Location/Qualifiers
source                 1..1272
                       mol_type = other DNA
                       organism = synthetic construct
SEQUENCE: 43
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttcaatttt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttgaaat attacccgaa tgatatttct tctcttatag gtaataagta tattatttgt    540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactac atctacttac aaagaaaata   780
aaatgagcga cttatatttt ttattagctt taatgattaa tctttataaa aaattactaa   840
aaatatttaa tgatacgtca tttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc  1020
ttttatttga cttcaaaata gttattgct tttataataa taatggtatg ataaaaaaaa  1080
aaaactaata gataaaaaaa gtacttagaa aacatttttt caagaacgtt aaaggtaaag  1140
tttagatgga ggcaattgtg tattttactg taaccaacca aggccgagta ctatcagcgt  1200
gttgcacatt ttggttatct ttagcacagt gttgaagata acgaacgaat agtgccatta  1260
ctgtaaccaa cc                                                     1272

SEQ ID NO: 44          moltype = DNA  length = 1272
FEATURE                Location/Qualifiers
source                 1..1272
                       mol_type = other DNA
                       organism = synthetic construct
SEQUENCE: 44
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttcaatttt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
```

```
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataaactat atctacttac aaagaaaata   780
aaatgagcga cttatatttt ttattagctt taatgattaa tctttataaa aaattactaa   840
aaatatttaa tgatacgtca ttttcaatt atgtttcttt cctttactaa actcgaatca   900
aatacaaaaa taaattgttt gagtgccgaa agtccgaaac ttattatttg acttcaaaat   960
aagttattgt ttttatctta taatcgt cctataaaaa aaattattct aaatattagc  1020
ttttatttga cttcaaaata agttattgct tttataataa taatgatatg ataaaaaaaa  1080
aaaactaata gataaagaaa gtacttagaa aacattttt caagaacgtt aaaggtaaag  1140
tttagatgga ggcaattgtg tatttttactg taaccaacca aggccgagta ctatcagcgt  1200
gttgcacatt ttggttatct ttagcacagt gttgaagata acgaacgaat agtgccatta  1260
ctgtaaccaa cc                                                      1272

SEQ ID NO: 45          moltype = DNA  length = 1272
FEATURE                Location/Qualifiers
source                 1..1272
                       mol_type = other DNA
                       organism = synthetic construct
SEQUENCE: 45
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtaatgagtc ctatgcatta   300
aacaaaaaaa agaaaatttt cttttcaattt ttcgattttt ccatttgatt ttattgtttg   360
ggaattattt tttccttaatt cttttccattc tatcaatgaa gaatctataa gaattctcaa   420
ttccatatca tttcatttt aaaaatttaa tcgtaatgga aataagaaag actaatattc   480
ctttggaaat attacccgaa tgatatttct tctcttatag tattatttgt              540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataaactat atctacttac aaagaaaata   780
aaatgagcga cttatatttt ttattagctt taatgattaa tctttataaa aaattactaa   840
aaatatttaa tgatacgtca ttttcaatt atgtttcttt cctttactaa actcgaatca   900
aatacaaaaa taaattgttt gagtgccgaa agtccgaaac ttattatttg acttcaaaat   960
aagttattgt ttttatctta taatcgt cctataaaaa aaattattct aaatattagc  1020
ttttatttga cttcaaaata agttattgct tttataataa taatgatatg ataaaaaaaa  1080
aaaactaata gataaagaaa gtacttagaa aacattttt ctagaacgtt aaaggtaaag  1140
tttagatgga ggcaattgtg tatttttactg taaccaacca aggccgagta ctatcagcgt  1200
gttgcacatt ttggttatct ttagcacagt gttgaagata acgaacgaat agtgccatta  1260
ctgtaaccaa cc                                                      1272

SEQ ID NO: 46          moltype = DNA  length = 1272
FEATURE                Location/Qualifiers
source                 1..1272
                       mol_type = other DNA
                       organism = synthetic construct
SEQUENCE: 46
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtaatgagtc ctatgcatta   300
aacaaaaaaa agaaaatttt cttttcaattt ttcgattttt ccatttgatt ttattgtttg   360
ggaattattt tttccttaatt cttttccattc tatcaatgaa gaatctataa gaattctcaa   420
ttccatatca tttcatttt aaaaatttaa tcgtaatgga aataagaaag actaatattc   480
ctttggaaat attacccgaa tgatatttct tctcttatag tattatttgt              540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataaactat atctacttac aaagaaaata   780
aaatgagcga cttatatttt ttattagctt taatgattaa tctttataaa aaattactaa   840
aaatatttaa tgatacgtca ttttcaatt atgtttcttt cctttactaa actcgaatca   900
aatacaaaaa taaattgttt gagtgccgaa agtccgaaac ttattatttg acttcaaaat   960
aagttattgt ttttatctta taatcgt cctataaaaa aaattattct aaatattagc  1020
ttttatttga cttcaaaata agttattgct tttataataa taatgatatg ataaaaaaaa  1080
aaaactaata gataaaaaaa gtacttagaa aacattttt caagaacgtt aaaggtaaag  1140
tttagatgga ggcaattgtg tatttttaccg taaccaacca aggccgagta ctatcagcgt  1200
gttgcacatt ttggttatct ttagcacagt gttgaagata acgaacgaat agtgccatta  1260
ctgtaaccaa cc                                                      1272

SEQ ID NO: 47          moltype = DNA  length = 1272
FEATURE                Location/Qualifiers
source                 1..1272
                       mol_type = other DNA
                       organism = synthetic construct
SEQUENCE: 47
```

```
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt tattcaataa tattataaat ttatatttta ctctaaaaat gtttatcaaa   240
ctaagtaaca tctggtttta tatttgttca gagaaaatgc gtagctaact ctatgcatta   300
aacaaaaaaa agaaaatttt ctttcaattt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac acaaaaaaag atcatgagta acttgatgat gctactgcca ttattaatag   720
tttaataatt attccttaaa ataaatagtt caataactac atctacttac aaagaaaata   780
aaatgagcga cttatatttt ttattagctt taatgattaa tctttataaa aaattactaa   840
aaatatttaa tgatacgtca ttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc  1020
cttatttga cttcaaaatg agttattgct tttataataa taatggtatg ataaaaaaaa  1080
aaaactaatg gataaagaaa gtacttagaa aacatttttt ctagaacgtt aaaggtaaag  1140
tttagatgga ggcaattgtg tatttactg taaccaacca aggccgagta ctatcagcgt  1200
gtcgcacatt ttggttatct ttagcacagt gttgaagata acgaacgaat agtgccatta  1260
ctgtaaccaa cc                                                      1272

SEQ ID NO: 48           moltype = DNA  length = 1272
FEATURE                 Location/Qualifiers
source                  1..1272
                        mol_type = other DNA
                        organism = synthetic construct
SEQUENCE: 48
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt ctttcaattt ttcgattttt ccatttgatt ttattgtttg   360
ggaattattt ttccttaatt cttttccattc tatcaatgaa gaatctatta gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca ttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc  1020
ttttatttga cttcaaaata agttattgct tttataataa taatgtatg ataaaaaaaa  1080
aaaactaata gataaaaaaa gtacttagaa aacatttttt caagaacgtt aaaggtaaag  1140
tttagatgga ggcaattgtg tatttactg taaccaacca aggccgagta ctatcagcgt  1200
gttgcacatt ttggttatct ttagcacagt gttgaagata acgaacgaat agtgccatta  1260
ctgtaaccaa cc                                                      1272

SEQ ID NO: 49           moltype = DNA  length = 1272
FEATURE                 Location/Qualifiers
source                  1..1272
                        mol_type = other DNA
                        organism = synthetic construct
SEQUENCE: 49
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt ctttcaattt tcgattttt ccatttgatt ttattgtttg    360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaagtttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca ttttcaatt atgtttcttt cctttactaa actcgaatca    900
aatacaaaaa taaattgttt gagtgccgaa agtccgaaac ttattatttg acttcaaaat   960
aagttattgt ttttatctta taataatcgt cctataaaaa aaattattct aaatattagc  1020
ttttatttga cttcaaaata agttattgct tttataataa taatgatatg ataaaaaaaa  1080
aaaactaata gataaaaaaa gtacttagaa aacatttttt caagaacgtt aaaggtaaag  1140
tttagatgga ggcaattgtg tatttactg taaccaacca aggccgagta ctatcagcgt   1200
gttgcacatt ttggttatct ttagcacagt gttgaagata acgaacgaat agtgccatta  1260
```

```
ctgtaaccaa cc                                                             1272

SEQ ID NO: 50           moltype = DNA  length = 1272
FEATURE                 Location/Qualifiers
source                  1..1272
                        mol_type = other DNA
                        organism = synthetic construct
SEQUENCE: 50
attaagaagc ttacaaagag attgggaact aaaactactt aaaaaaaaag gaattaaaat          60
caatttcaac caaattataa gagacttaag atacatttta ttctaggaaa caatattact         120
tctggacttt taaacaagaa acaaaaaata aattaattaa gatcaattga atagttaatt         180
taattatttt taatcaataa tattataaat ttatatttta ttctaaaaat gtttatcaaa         240
ctaagtaaca tctggtttta tatttgttca gagaaaatgc gtagctaact ctatgcatta         300
aacaaaaaaa agaaaatttt ctttcaattt ttcgattttt ccatttgatt ttattgtttg         360
ggaattattt ttccttaatt cttccattc tatcaatgaa gaatctataa gaattctcaa         420
ttccatatca tttcattttt aaaaatttaa tcgtaatgga aataagaaag actaatattc         480
ctttggaaat attacccgaa tgatatttct tctcttatag gtaataagta tattatttgt         540
aattcaatag aacaaatttc ttatattgtt attagttcaa taaatatatt tatttacata         600
aaaaataata aaaggagatc tatcttaaat tcttgtatat gaaatttgat tctcgtgaat         660
gaaacaaaac ataaaaaaag atcatgagta acttgatgat gctattgcca ttattaatag         720
tttaataatt attccttaaa ataaatagtt caataactat atctacttac aaagaaaata         780
aaatgggcga cttatatttt ttattagctt taatgcttca tctttataaa aaattactaa         840
aaatatttaa tgatacgtca ttttttcaatt atgtttcttt cctttactaa actcgaatca         900
aatacaaaaa taaattgttt gagtgccgaa agtccgaaac ttattatttg acttcaaaat         960
aagttattgt ttttatctta taataatcgt cctataaaaa aaattattct aaatattagc        1020
ttttatttga cttcaaaata agttattgct tttaataataa taatgatatg ataaaaaaa        1080
aaaactaata gataaaaaaa gtacttagaa aacatttttt caagaacgtt aaaggtaaag        1140
tttagatgga ggcaattgtg tattttactg taaccaacca aggccgagta ctatcagcgt        1200
gttgcacatt ttggttatct ttagcacagt gttgaagata acgaacgaat agtgccatta        1260
ctgtaaccaa cc                                                            1272

SEQ ID NO: 51           moltype = DNA  length = 1272
FEATURE                 Location/Qualifiers
source                  1..1272
                        mol_type = other DNA
                        organism = synthetic construct
SEQUENCE: 51
attaagaagc ttacaaagag attgggaact aaaactactt aaaaaaaaag gaattaaaat          60
caatttcaac caaattataa gagacttaag atacatttta ttctaggaaa caatattact         120
tctggacttt taaacaagaa acaaaaaata aattaattaa gatcaattga atagttaatt         180
taattatttt taatcaataa tattataaat ttatatttta ttctaaaaat gtttatcaaa         240
ctaagtaaca tctggtttta tatttgttca gagaaaatgc gtagctaact ctatgcatta         300
aacaaaaaaa agaaaatttt ctttcaattt ttcgattttt ccatttgatt ttattgtttg         360
ggaattattt ttccttaatt cttccattc tatcaatgaa gaatctataa gaattctcaa         420
ttccatatca tttcattttt aaaaatttaa tcgtaatgga aataagaaag actaatattc         480
ctttggaaat attacccgaa tgatatttct tctcttatag gtaataagta tattatttgt         540
aattcaatag aacaaatttc ttatattgtt attagttcaa taaatatatt tatttacata         600
aaaaataata aaaggagatc tatcttaaat tcttgtatat gaaatttgat tctcgtgaat         660
gaaacaaaac ataaaaaaag atcatgagta acttgatgat gctattgcca ttattaatag         720
tttaataatt attccttaaa ataaatagtt caataactat atctacttac aaagaaaata         780
aaatgagcga cttatatttt ttattagctt taatgcttca tctttataaa aaattactaa         840
aaatatttaa tgatacgtca ttttttcaatt atgtttcttt cctttactaa actcgaatca         900
aatacaaaaa taaattgttt gagtgccgaa agtccgaaac ttattatttg acttcaaaat         960
aagttattgt ttttatctta taataatcgt cctataaaaa aaattattct aaatattagc        1020
ttttatttga cttcaaaata agttattgct tttaataataa taatgatatg ataaaaaaa        1080
aaaactaata gataaaaaaa gtacttagaa aacatttttt caagaacgtt aaaggtaaag        1140
tttagatgga ggcaattgtg tattttactg taaccaacca aggccgagta ctatcagcgt        1200
gttgcacatt ttggttatct ttagcacagt gttgaagata acgaacgaat agtgccatta        1260
ctgtaaccaa cc                                                            1272

SEQ ID NO: 52           moltype = DNA  length = 1272
FEATURE                 Location/Qualifiers
source                  1..1272
                        mol_type = other DNA
                        organism = synthetic construct
SEQUENCE: 52
attaagaagc ttacaaagag attgggaact aaaactactt aaaaaaaaag gaattaaaat          60
caatttcaac caaattataa gagacttaag atacatttta ttctaggaaa caatattact         120
tctggacttt taaacaagaa acaaaaaata aattaattaa gatcaattga atagttaatt         180
taattatttt taatcaataa tattataaat ttatatttta ttctaaaaat gtttatcaaa         240
ctaagtaaca tctggtttta tatttgttca gagaaaatgc gtagctaact ctatgcatta         300
aacaaaaaaa agaaaatttt ctttcaattt ttcgattttt ccatttgatt ttattgtttg         360
ggaattattt ttccttaatt cttccattc tatcaatgaa gaatctataa gaattctcaa         420
ttccatatca tttcattttt aaaaatttaa tcgtaatgga aataagaaag actaatattc         480
ctttggaaat attacccgaa tgatatttct tctcttatag gtaataagta tattatttgt         540
aattcaatag aacaaatttc ttatattgtt attagttcaa taaatatatt tatttacata         600
aaaaataata aaaggagatc tatcttaaat tcttgtatat gaaatttgat tctcgtgaat         660
gaaacaaaac ataaaaaaag atcatgagta acttgatgat gctattgcca ttattaatag         720
tttaataatt attccttaaa ataaatagtt caataactat atctacttac aaagaaaata         780
```

```
aaatgagcga cttatatttt ttattagctt taatgattaa tctttataaa aaattactaa  840
aaatatttaa tgatacgtca tttttcaatt atgtttcttt cctttactaa actcgaatca  900
aatacaaaaa taaattgttt gagtgccgaa agtccgaaac atattatttg acttcaaaat  960
aagttattgt ttttatctta taataatcgt cctataaaaa aaattattct aaatattagc  1020
tttatttga cttcaaaata agttattgct tttataataa taatgatatg ataaaaaaaa  1080
aaaactaata gataaaaaaa gtacttagaa acattttttt caagaacgtt aaaggtaaag  1140
tttagatgga ggcaattgtg tatttttactg taaccaacca aggccgagta ctatcagcgt  1200
gttgcacatt ttggttatct ttagcacagt gttgaagata acgaacgaat agtgccatta  1260
ctgtaaccaa cc                                                      1272

SEQ ID NO: 53          moltype = DNA  length = 1272
FEATURE                Location/Qualifiers
source                 1..1272
                       mol_type = other DNA
                       organism = synthetic construct
SEQUENCE: 53
attaagaagc ttcaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatattttta ttctaaaaat gtttatcaaa   240
ctaagtaaca tctggtttta tatttgttca gagaaaatgc gtagctaact ctatgcatta   300
aacaaaaaaa agaaaatttt cttttcaattt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaaatttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca tttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc   1020
tttatttga cctcaaaata agttattgct tttataataa taatgatatg ataaaaaaaa   1080
aaaactaata gataaaaaaa gtacttagaa acattttttt caagaacgtt aaaggtaaag   1140
tttagatgga ggcaattgtg tatttttactg taaccaacca aggccgagta ctatcagcgt   1200
gttgcacatt ttggttatct ttagcacagt gttgaagata acgaacgaat agtgccatta   1260
ctgtaaccaa cc                                                      1272

SEQ ID NO: 54          moltype = DNA  length = 1271
FEATURE                Location/Qualifiers
source                 1..1271
                       mol_type = other DNA
                       organism = synthetic construct
SEQUENCE: 54
attaagaagc ttcaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatattttta ttctaaaaat gtttatcaaa   240
ctaagtaaca tctggtttta tatttgttca gagaaaatgc gtagctaact ctatgcatta   300
aacaaaaaaa agaaaatttt cttttcaattt ttcgattttt ccatttgatt ttattgtttg   360
ggaattattt ttccttaatt cttttccattc tatcaatgaa gaatctatta gaattctcaa   420
ttccatatca tttcattttt aaaaatttaa tcgtaatgga aataagaaag actaatattc   480
ctttggaaat attacccgaa tgatatttct tctcttatag gtaataagta tattatttgt   540
aattcaatag aacaagtttc ttatattgtt attagttcaa taaatatatt tatttacata   600
aaaaataata aaaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgggcga cttatatttt ttattagctt taatgtttaa tctttataaa aaattactaa   840
aaatatttaa tgatacgtca tttttcaatt atgtttcttt cctttactaa actcgaatca   900
aatacaaaaa taaattgttt gagtgccgaa agtccgaaac atattatttg acttcaaaat   960
aagttattgt ttttatctta taataatcgt cctataaaaa aaattattct aaatattagc   1020
tttatttga cctcaaaata agttattgct tttataataa taatgatatg ataaaaaaaa   1080
aaactaatag ataaaaaaag tacttagaaa acattttttc aagaacgtta aaggtaaagt   1140
ttagatggag gcaattgtgt atttactgt aaccaaccaa ggccgagtac tatcagcgtg   1200
ttgcacattt tggttatctt tagcacagtg ttgaagataa cgaacgaata gtgccattac   1260
tgtaaccaac c                                                       1271

SEQ ID NO: 55          moltype = DNA  length = 1272
FEATURE                Location/Qualifiers
source                 1..1272
                       mol_type = other DNA
                       organism = synthetic construct
SEQUENCE: 55
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatattttta ttctaaaaat gtttatcaaa   240
ctaagtaaca tctggtttta tatttgttca gagaaaatgc gtagctaact ctatgcatta   300
```

```
aacaaaaaaa agaaaatttt cttttcaattt ttcgattttt ccatttgatt ttattgtttg    360
ggaattattt ttccttaatt cttttccattc tatcaatgaa gaatctataa gaattctcaa    420
ttccatatca tttcattttt aaaaatttaa tcgtaatgga aataagaaag actaatattc    480
ctttggaaat attacccgaa tgatatttct tctcttatag gtaataagta tatttatttgt   540
aattcaatag aacaaatttc ttatattgtt attagttcaa taaatatatt tatttacata    600
aaaaataata aaaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactat atctacttac aaagaaaata    780
aaatgagcga cttatatttt ttattagctt taatgattaa tctttataaa aaagtactaa    840
aaatatttaa tgatacgtca tttttcaatt atgtttcttt cctttactaa actcgaatca    900
aatacaaaaa taaattgttt gagtgccgaa agtccgaaac ttattatttg acttcaaaat    960
aagttattgt ttttatctta taataatcgt cctataaaaa aaattattct aaatattagc   1020
ttttatttga cttcaaaata agttattgct tttataataa taatgatatg ataaaaaaaa   1080
aaaactaata gataaaaaaa gtacttagaa aacatttttc caagaacgtt aaaggtaaag   1140
tttagatgga ggcaattgtg tattttactg taaccaacca aggccgagta ctatcagcgt   1200
gttgcacatt ttggttatct ttagcacagt gttgaagata acgaacgaat agtgccatta   1260
ctgtaaccaa cc                                                       1272
```

SEQ ID NO: 56          moltype = DNA   length = 1271
FEATURE                Location/Qualifiers
source                 1..1271
                       mol_type = other DNA
                       organism = synthetic construct SEQUENCE: 56
```
attaagaagc ttacaaagag attgggaact aaaactactt aaaaaaaaag gaattaaaat      60
caatttcaac caaattataa gagacttaag atacatttta ttctaggaaa caatattact    120
tctggacttt taaacaagaa acaaaaaata aattaattaa gatcaattga atagttaatt    180
taattatttt taatcaataa tattataaat ttatattttta ttctaaaaat gtttatcaaa   240
ctaagtaaca tctggtttta tatttgttca gagaaaatgc gtagctaact ctatgcatta    300
aacaaaaaaa agaaaatttt cttttcaattt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc    480
ctttggaaat attacccgaa tgatatttct tctcttatag gtaataagta tatttatttgt   540
aattcaatag aacaaatttc ttatattgtt attagttcaa taaatatatt tatttacata    600
aaaaataata aaaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactat atctacttac aaagaaaata    780
aaatgagcga cttatatttt ttattagctt taatgattaa tctttataaa aaagtactaa    840
aaatatttaa tgatacgtca tttttcaatt atgtttcttt cctttactaa actcgaatca    900
aatacaaaaa taaattgttt gagtgccgaa agtccgaaac ttattatttg acttcaaaat    960
aagttattgt ttttatctta taataatcgt cctataaaaa aaattattct aaatattagc   1020
ttttatttga cttcaaaata agttattgct tttataataa taatgatatg ataaaaaaaa   1080
aaaactaata gataaaaaag tacttagaaa acatttttc aagaacgtta aaggtaaagt    1140
ttagatggag gcaattgtgt attttactgt aaccaaccaa ggccgagtac tatcagcgtg   1200
ttgcacattt tggttatctt tagcacagtg ttgaagataa cgaacgaata gtgccattac   1260
tgtaaccaac c                                                        1271
```

SEQ ID NO: 57          moltype = DNA   length = 1272
FEATURE                Location/Qualifiers
source                 1..1272
                       mol_type = other DNA
                       organism = synthetic construct SEQUENCE: 57
```
attaagaagc ttacaaagag attgggaact aaaactactt aaaaaaaaag gaattaaaat      60
caatttcaac caaattataa gagacttaag atacatttta ttctaggaaa caatattact    120
tctggacttt taaacaagaa acaaaaaata aattaattaa gatcaattga atagttaatt    180
taattatttt taatcaataa tattataaat ttatattttta ttctaaaaat gtttatcaaa   240
ctaagtaaca tctggtttta tatttgttca gagaaaatgc gtagctaact ctatgcatta    300
aacaaaaaaa agaaaatttt cttttcaattt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc    480
ctttggaaat attacccgaa tgatatttct tctcttatag gtaataagta tatttatttgt   540
aattcaatag aacaaatttc ttatattgtt attagttcaa taaatatatt tatttacata    600
aaaaataata aaaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactat atctacttac aaagaaaata    780
aaatgagcga cgtatatttt ttattagctt taatgattaa tctttataaa aaattactaa    840
aaatatttaa tgatacgtca tttttcaatt atgtttcttt cctttactaa actcgaatca    900
aatacaaaaa taaattgttt gagtgccgaa agtccgaaac ttattatttg acttcaaaat    960
aagttattgt ttttatctta taataatcgt cctataaaaa aaattattct aaatattagc   1020
ttttatttga cttcaaaata agttattgct tttataataa taatgatatg ataaaaaaaa   1080
aaaactaata gataaaaaaa gtacttagaa aacatttttc caagaacgtt aaaggtaaag   1140
tttagatgga ggcaattgtg tattttactg taaccaacca aggccgagta ctatcagcgt   1200
gttgcacatt tgggttatct ttagcacagt gttgaagata acgaacgaat agtgccatta   1260
ctgtaaccaa cc                                                       1272
```

SEQ ID NO: 58          moltype = DNA   length = 1272
FEATURE                Location/Qualifiers
source                 1..1272

```
                    mol_type = other DNA
                    organism = synthetic construct
SEQUENCE: 58
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttcaatttt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attcccgaaa tgatatttct tctcttatag gtaataagta tattatttgt   540
aattcaatag aacaaatttc ttatattgtt attagttcaa taaatatatt tatttacata   600
aaaaataata aaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca ttttttcaatt atgtttcttt cctttactaa actcgaatca   900
gatacaaaaa taaattgttt gagtgccgaa agtccgaaac ttattatttg acttcaaaat   960
aagttattgt ttttatctta taataatcgt cctataaaaa aaattattct aaatattagc  1020
ttttatttga cttcaaaata agttattgct tttataataa taatgatatg ataaaaaaaa  1080
aaaactaata gataaaaaaa gtacttagaa aacattttt caagaacgtt aaaggtaaag  1140
tttagatgga ggcaattgtg tattttactg taaccaacca aggccgagta ctatcagcgt  1200
gttgcacatt ttggttatct ttagcacagt gttgaagata acgaacgaat agtgccatta  1260
ctgtaaccaa cc                                                       1272

SEQ ID NO: 59           moltype = DNA  length = 1272
FEATURE                 Location/Qualifiers
source                  1..1272
                        mol_type = other DNA
                        organism = synthetic construct
SEQUENCE: 59
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttcaatttt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attcccgaaa tgatatttct tctcttatag gtaataagta tattatttgt   540
aattcaatag aacaaatttc ttatattgtt attagttcaa taaatatatt tatttacata   600
aaaaataata aaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca ttttttcaatt atgtttcttt cctttactaa actcgaatca   900
aatacaaaaa taaattgttt gagtgccgaa agtccgaaac ttattatttg acttcaaaat   960
aagttcttgt ttttatctta taataatcgt cctataaaaa aaattattct aaatattagc  1020
ttttatttga cttcaaaata agttattgct tttataataa taatgatatg ataaaaaaaa  1080
aaaactaata gataaaaaaa gtacttagaa aacattttt caagaacgtt aaaggtaaag  1140
tttagatgga ggcaattgtg tattttactg taaccaacca aggccgagta ctatcagcgt  1200
gttgcacatt ttggttatct ttagcacagt gttgaagata acgaacgaat agtgccatta  1260
ctgtaaccaa cc                                                       1272

SEQ ID NO: 60           moltype = DNA  length = 1272
FEATURE                 Location/Qualifiers
source                  1..1272
                        mol_type = other DNA
                        organism = synthetic construct
SEQUENCE: 60
attaagaagc ttacaaagag attgggaact aaaactactt aaaaaaaaag gaattaaaat    60
caatttcaac caaattataa gagacttaag atacatttta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttcaatttt ttcgattttt ccatttgatt ttattgtttg   360
ggaattattt ttccttaatt cttttccattc tatcaatgaa gaatctataa gaattctcaa   420
ttccatatca tttcattttt aaaaatttaa tcgtaatgga aataagaaag actaatattc   480
ctttggaaat attcccgaaa tgatatttct tctcttatag gtaataagta tattatttgt   540
aattcaatag aacaaatttc ttatattgtt attagttcaa taaatatatt tatttacata   600
aaaaataata aaggagatc tatcttaaat tcttgtatat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca ttttttcaatt atgtttcttt cctttactaa actcgaatca   900
aatacaaaaa taaattgttt gagtgccgaa agtccgaaac ttattatttg acttcaaaat   960
aagttattgt ttttatctta taataatcgt cctataaaaa aaattattct aaatattagc  1020
ttttatttga cttcaaaata agttattgct tttataataa taatgatatg ataaaaaaaa  1080
```

```
agaactaata gataaaaaaa gtacttagaa aacattttt caagaacgtt aaaggtaaag   1140
tttagatgga ggcaattgtg tattttactg taaccaacca aggccgagta ctatcagcgt   1200
gttgcacatt ttggttatct ttagcacagt gttgaagata acgaacgaat agtgccatta   1260
ctgtaaccaa cc                                                       1272

SEQ ID NO: 61           moltype = DNA   length = 1271
FEATURE                 Location/Qualifiers
source                  1..1271
                        mol_type = other DNA
                        organism = synthetic construct
SEQUENCE: 61
attaagaagc ttacaaagag attgggaact aaaactactt aaaaaaaaag gaattaaaat   60
caatttcaac caaattataa gagacttaag atacattta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttcaatt ttcgattttt ccatttgatt ttattgtttg   360
ggaattattt ttccttaatt ctttccattc tatcaatgaa gaatctataa gaattctcaa   420
ttccatatca tttcatttt aaaaatttaa tcgtaatgga aataagaaag actaatattc   480
ctttggaaat attcccgaa tgatattct tctcttatag gtaataagta tattatttgt   540
aattcaatag aacaaatttc ttatattgtt attagttcaa taaatatatt tatttacata   600
aaaaatata aaggagatc tatcttaaat tcttgtaat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca ttttcaatt atgtttcttt cctttactaa actcgaatca   900
gatacaaaaa taaattgttt gagtgccgaa agtccgaaac ttattattg acttcaaaat   960
aagttcttgt ttttatctta taataatcgt cctataaaaa aaattattct aaatatttagc  1020
ttttatttga cttcaaaata agttattgct tttataataa taatgatatg ataaaaaaaa  1080
agactaatag ataaaaaaag tacttagaaa acatttttc aagaacgtta aaggtaaagt  1140
ttagatggag gcaattgtgt atttactgt aaccaaccaa ggccgagtac tatcagcgtg  1200
ttgcacattt tggttatctt tagcacagtg gttgaagataa cgaacgaata gtgccattac  1260
tgtaaccaac c                                                        1271

SEQ ID NO: 62           moltype = DNA   length = 1272
FEATURE                 Location/Qualifiers
source                  1..1272
                        mol_type = other DNA
                        organism = synthetic construct
SEQUENCE: 62
attaagaagc ttacaaagag attgggaact aaaactactt aaaaaaaaag gaattaaaat   60
caatttcaac caaattataa gagacttaag atacattta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttcaatt ttcgattttt ccatttgatt ttattgtttg   360
ggaattattt ttccttaatt ctttccattc tatcaatgaa gaatctataa gaattctcaa   420
ttccatatca tttcatttt aaaaatttaa tcgtaatgga aataagaaag actaatattc   480
ctttggaaat attcccgaa tgatattct tctcttatag gtaataagta tattatttgt   540
aattcaatag aacaaatttc ttatattgtt attagttcaa taaatatatt tatttacata   600
aaaaatata aaggagatc tatcttaaat tcttgtaat gaaatttgat tctcgtgaat   660
gaaacaaaac ataaaaaaag atcatgagta acttgatgat gctattgcca ttattaatag   720
tttaataatt attccttaaa ataaatagtt caataactat atctacttac aaagaaaata   780
aaatgagcga cttatatttt ttattagctt taatgattaa tctttataaa aaattactaa   840
aaatatttaa tgatacgtca ttttcaatt atgtttcttt cctttactaa actcgaatca   900
aatacaaaaa taaattgttt gagtgccgaa agtccgaaac ttattattg acttcaaaat   960
aagttattgt ttttatctta taataatcgt cctataaaaa aaattattct aaatatttagc  1020
ttttatttga cttcaaaata agttattgct tttataataa taatgatatg ataaaaaaaa  1080
aaaactaata gataaaaaaa gtacttagaa aacattttt caagaacgtt aaaggtaaag   1140
tttagatgga ggcaattgtg tattttactg taaccaacca aggccgagta ctatcagcgt   1200
gttgcacatt ttggttatct ttagcacagt gttgaagata acgaacgaat agtgccatta   1260
ctgtaaccaa cc                                                       1272

SEQ ID NO: 63           moltype = DNA   length = 1271
FEATURE                 Location/Qualifiers
source                  1..1271
                        mol_type = other DNA
                        organism = synthetic construct
SEQUENCE: 63
attaagaagc ttacaaagag attgggaact aaaactactt aaaaaaaaag gaattaaaat   60
caatttcaac caaattataa gagacttaag atacattta ttctaggaaa caatattact   120
tctggacttt taaacaagaa acaaaaaata aattaattaa gatcaattga atagttaatt   180
taattatttt taatcaataa tattataaat ttatatttta ttctaaaaat gtttatcaaa   240
ctaagtaaca tctggtttta tatttgttca gagaaaatgc gtagctaact ctatgcatta   300
aacaaaaaaa agaaaatttt cttcaatt ttcgattttt ccatttgatt ttattgtttg   360
ggaattattt ttccttaatt ctttccattc tatcaatgaa gaatctataa gaattctcaa   420
ttccatatca tttcatttt aaaaatttaa tcgtaatgga aataagaaag actaatattc   480
ctttggaaat attcccgaa tgatattct tctcttatag gtaataagta tattatttgt   540
aattcaatag aacaaatttc ttatattgtt attagttcaa taaatatatt tatttacata   600
```

-continued

```
aaaaataata taaggagatc tatcttaaat tcttgtatat gaaatttgat tctcgtgaat    660
gaaacaaaac ataaaaaaag atcatgagta acttgatgat gctattgcca ttattaatag    720
tttaataatt attccttaaa ataaatagtt caataactat atctacttac aaagaaaata    780
aaatgagcga cttatatttt ttattagctt taatgattaa tctttataaa aaattactaa    840
aaatatttaa tgatacgtca tttttcaatt atgtttcttt cctttactaa actcgaatca    900
aatacaaaaa taaattgttt gagtgccgaa agtccgaaac ttattatttg acttcaaaat    960
aagttattgt ttttatctta taataatcgt cctataaaaa aaattattct aaatattagc   1020
ttttatttga cttcaaaata agttattgct tttataataa taatgatatg ataaaaaaaa   1080
aaactaatag ataaaaaaag tacttagaaa acattttttc aagaacgtta aaggtaaagt   1140
ttagatggag gcaattgtgt attttactgt aaccaaccaa ggccgagtac tatcagcgtg   1200
ttgcacattt tggttatctt tagcacagtg ttgaagataa cgaacgaata gtgccattac   1260
tgtaaccaac c                                                        1271
```